(12) United States Patent
Rajagopal et al.

(10) Patent No.: US 10,273,450 B2
(45) Date of Patent: Apr. 30, 2019

(54) ISOLATED HUMAN LUNG PROGENITOR CELLS AND USES THEREOF

(71) Applicant: THE GENERAL HOSPITAL CORPORATION, Boston, MA (US)

(72) Inventors: Jayaraj Rajagopal, Lincoln, MA (US); Hongmei Mou, Medford, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 15/635,975

(22) Filed: Jun. 28, 2017

(65) Prior Publication Data

US 2017/0369839 A1    Dec. 28, 2017

Related U.S. Application Data

(62) Division of application No. 14/371,627, filed as application No. PCT/US2013/021186 on Jan. 11, 2013, now Pat. No. 9,828,583.

(Continued)

(51) Int. Cl.
   *C12N 5/074*    (2010.01)
   *A61K 35/42*   (2015.01)
   (Continued)

(52) U.S. Cl.
   CPC ............ *C12N 5/0607* (2013.01); *A61K 35/42* (2013.01); *A61L 27/3834* (2013.01); *A61L 27/3882* (2013.01); *A61L 27/56* (2013.01); *A61L 27/58* (2013.01); *C12N 5/068* (2013.01); *C12N 5/0678* (2013.01); *C12N 5/0688* (2013.01);

(Continued)

(58) Field of Classification Search
None
See application file for complete search history.

(56) References Cited

U.S. PATENT DOCUMENTS 7,541,185 B2   6/2009   D'Amour et al.
7,695,963 B2   4/2010   Agulnick et al.
(Continued)

FOREIGN PATENT DOCUMENTS

CA    2645541 A1    9/2007
WO    2000/055300 A1    9/2000
(Continued)

OTHER PUBLICATIONS

Ameri et al. "FGF2 specifies hESC-derived definitive endoderm into foregut/midgut cell lineages in a concentration-dependent manner." Stem Cells 28(1):45-56 (2010).
(Continued)

*Primary Examiner* — David W Berke-Schlessel
(74) *Attorney, Agent, or Firm* — Nixon Peabody LLP; David S. Resnick; Mark J. FitzGerald

(57) ABSTRACT

Provided herein are methods and compositions relating, in part, to the generation of human progenitor cells committed to the lung lineage and uses of such cells for treatment of lung diseases/disorders or injury to the lung. Whether an adult stem cell can be isolated from human adult lung remains controversial in the art and at present, methods for isolating and using adult lung stem cells from humans lack reproducibility. Thus, the methods and compositions described herein are advantageous over the present state of knowledge in the art and permit the generation of human lung progenitor cells for treatment, tissue engineering, and screening assays.

3 Claims, 12 Drawing Sheets
Specification includes a Sequence Listing.

Related U.S. Application Data

(60) Provisional application No. 61/619,568, filed on Apr. 3, 2012, provisional application No. 61/586,551, filed on Jan. 13, 2012.

(51) Int. Cl.

| | |
|---|---|
| *A61L 27/38* | (2006.01) |
| *A61L 27/56* | (2006.01) |
| *A61L 27/58* | (2006.01) |
| *G01N 33/68* | (2006.01) |
| *C12N 5/071* | (2010.01) |
| *A61K 9/00* | (2006.01) |

(52) U.S. Cl.
CPC ....... *C12N 5/0689* (2013.01); *G01N 33/6884* (2013.01); *A61K 9/0073* (2013.01); *A61L 2430/22* (2013.01); *C12N 2501/115* (2013.01); *C12N 2501/117* (2013.01); *C12N 2501/15* (2013.01); *C12N 2501/155* (2013.01); *C12N 2501/16* (2013.01); *C12N 2501/385* (2013.01); *C12N 2501/415* (2013.01); *C12N 2501/727* (2013.01); *C12N 2506/02* (2013.01); *C12N 2506/45* (2013.01); *C12N 2533/90* (2013.01)

(56) References Cited

U.S. PATENT DOCUMENTS

| | | | |
|---|---|---|---|
| 7,993,916 | B2 | 8/2011 | Agulnick et al. |
| 8,034,613 | B2 | 10/2011 | Slukvin et al. |
| 2007/0160976 | A1 | 7/2007 | Okihana |
| 2007/0259423 | A1 | 11/2007 | Odorico et al. |
| 2008/0292677 | A1 | 11/2008 | Cortiella et al. |
| 2009/0298178 | A1 | 12/2009 | D'Amour |
| 2010/0266552 | A1 | 10/2010 | Jenkin et al. |
| 2010/0272695 | A1 | 10/2010 | Agulnick et al. |

FOREIGN PATENT DOCUMENTS

| | | |
|---|---|---|
| WO | 2001/010478 A1 | 2/2001 |
| WO | 2003/046141 A1 | 6/2003 |
| WO | 2004/028583 A2 | 4/2004 |
| WO | 2007/025233 A1 | 3/2007 |
| WO | 2007/056578 A1 | 5/2007 |
| WO | 2007/115018 A2 | 10/2007 |
| WO | 2008/144820 A1 | 12/2008 |
| WO | 2010/136583 A2 | 12/2010 |
| WO | 2011/003422 A1 | 1/2011 |
| WO | 2011/031875 A2 | 3/2011 |
| WO | 2010/136583 A3 | 6/2011 |
| WO | 2011/139628 A1 | 11/2011 |
| WO | 2011/157029 A1 | 12/2011 |

OTHER PUBLICATIONS

Beers et al., "The three R's of lung health and disease: repair, remodeling and regeneration", Journal of Clinical Investigation 121(6):2065-2073 (2011).
Christodoulou et al. "Mouse ES and iPS cells can form similar definitive endoerm despite differences in imprinted genes." JCI 121(6):2313-2325 (2011).
Coraux et al. "Embryonic stem cells generate airway epithelia tissue." Am J Resp Cell Molec Biol 32:87-92 (2005).
D'Amour, et al. "Efficient differentiation of human embryonic stem cells to definitive endoderm." Nature Biotechnology 23(12)1534-1541 (2005).
Domyan et al., "Signaling through BMP receptors promotes respiratory identity in the foregut via repression of Sox2." Development, 138(5):971-981 (2011).
Evans et al. "Cellular and molecular characteristics of basal cells in airway epithelium." Experimental Lung Research I 27:401-415 (2001).
Gontan et al., "Sox2 is important for two crucial processes in lung development: branching morphogenesis and epithelial cell differentiation", Developmental Biology 317:296-309 (2008).
Goss et al. "Wnt signaling and specification of the respiratory endoderm." Cell Cycle 9:1-10 (2010).
Goss et al. "Wnt2/2b and beta-catenin signaling are necessary and sufficient to specify lung progenitors in the foregut." Developmental Cell (2009) 17(2):290-298.
Green et al. "Generation of anterior foregut endoderm from human embryonic and induced pluripotent stem cells." Nature Biotechnology 29(3):267-272 (2011).
Kim et al. "Differentiation of Mouse Embryonic Stem Cells into Endoderm without Embryoid Body Formation" PLoS One (2010) 5(11):e14146.
Kingham et al., J Cell Science 122:2311-2321 (2009). "Distinct roles for isoforms of the catalytic subunit of class—IA PI3K in the regulation of behaviour of murine embryonic stem cells."
Lazzaro et al. "The transcription factor TTF-1 is expressed at the onset of thyroid and lung morphogenesis and in restricted regions of the foetal brain" Development Cell 113:1093-1104 (1991).
Lebeche et al. "Fibroblast growth factor interactions in the developing lung." Mechanisms of Development 86:125-136 (1999).
Livigni et al. "Differentiation of Embryonic Stem Cells into Anterior Definitive Endoderm" Current Protocols in Stem Cell Biology10:G:1G.3:1G.3.1-1G.3.10 (2009).
Longmire et al., "Efficient Derivation of Purified Lung and Thyroid Progenitors from Embriyonic Stem Cells", Cell Stem Cell, 10(4):398-411 (2012).
Malpel et al. "Regulation of retinoic acid signaling during lung morphogenesis." Development (Cambridge, England) 127:3057-3067 (2000).
Minoo et al. "Defects in tracheoesophageal and lung morphogenesis in Nkx2.1(1/1) mouse embryos." Developmental Biology 209:60-71 (1999).
Morrisey et al., Developmental Cell 18:8-23 (2010). "Preparing for the first breath: genetic and cellular mechanisms in lung development."
Morrison et al. "Anterior definitive endoderm from ESCs reveals a role for FGF signaling." Cell Stem Cell (2008) 3:355-356.
Mou et al. "Generation of multipotent lung and airway progenitors from mouse ESCs and patient-specific cystic fibrosis iPSCs." Cell Stem Cell 10(4):385-97 (2012).
Okubo et al. "Hyperactive Wnt signaling changes the developmental potential of embryonic lung endoderm" Journal of biology 3(3):11 (2004).
Pacheco-Pinedo et al. "Wnt/b-catenin signaling accelerates mouse lung tumorigenesis by imposing an embryonic distal progenitor phenotype on lung epithelium." J Clin Invest 121(5):1935-1945 (2011).
Perl et al. "Normal lung development and function after Sox9 inactivation in the respiratory epithelium." Genesis 41:23-32 (2005).
Peterson et al., "Tissue-Engineered Lungs for in Vivo Implantation", Science 329:538-541 (2010).
Pilquil et al. "The generation and isolation of NKX2.1 expressing populations from human pluripotent stem cells, and their ability to produce lung epithelium." International Society for Stem Cell Research Jun. 15-18, 2011, abstract No. 3372.
Que et al. "Morphogenesis of the trachea and esophagus: current players and new roles for noggin and Bmps." Differentiation; Research in Biolgoical Diversity 74:422-437 (2006).
Que et al. "Multiple roles for Sox2 in the developing and adult mouse trachea." Development (Cambridge England) 136:1899-1907 (2009).
Que et al., "Multiple dose-dependent roles for Sox2 in the patterning and differentiation of anterior foregut endoderm", Development 134:2521-2531 (2007).
Rawlins et al. "The Id2+ distal tip lung epithelium contains individual multipotent embryonic progenitor cells." Development (Cambridge, England) 136:3741-3745 (2009).
Rock et al. "Airway basal stem cells: a perspective on their roles in epithelial homeostasis and remodeling." Diseae Models & Mechanisms 3(9-10):545-556 (2010).

(56) References Cited

OTHER PUBLICATIONS

Rock et al. "Basal cells as stem cells of the mouse trachea and human airway epithelium" PNAS 106 (31):12771-12775 (2009).

Roszell et al. "Efficient derivation of alveolar type II cells from embryonic stem cells for in vivo application." Tisse Eng Part A 15(11):3351-3365 (2009).

Samadikuchaksaraei et al. "Derivation of distal airway epithelium from human embryonic stem cells." Tissue Engineering12(4):867-875 (2006).

Serls et al. "Different thresholds of fibroblast growth factors pattern the ventral foregut into liver and lung." Development (Cambridge, England) 132(1):35-47 (2005).

Sherwood et al. "Wnt signaling specifies and patterns intestinal endoderm." Mech Dev. 128(7-10):387-400 (2011).

Shu et al. "Wnt/beta-catenin signaling acts upstream of N-myc, BMP4, and FGF signaling to regulate proximal-distal patterning in the lung." Developmental Biology 283:226-239 (2005).

Spence et al. "Directed differentiation of human pluripotent stem cells into intestinal tissue in vitro." Nature 470 (7332)105-109 (2011).

Tsaniras et al., J of Endochronology 206:13-26 (2010). "Generating pancreatic beta=cells from embryonic stem cells by manipulating signaling pathways."

Tsentr mediko-biologischeskikh technologiy. Kletochnaya terapiya bolexney legkikh, Aug. 2, 2006, pp. 1-14 [retrieved on Sep. 4, 2013]/ Retrieved from the Internet: http://www.cmbt.su/eng/science81.html [English Abstract].

Turovets et al. "Human parthenogenetic stem cells produce enriched populations of definitive endoderm cells after trichostatin A pretreatment." Differentiation (2011) 81(5):292-298.

Van Haute et al. "Generation of lung epithelial-like tissue from human embryonic stem cells." Respiratory Research 10:105 (1-13) (2009).

Van Vranken et al. "Coculture of embryonic stem cells with pulmonary mesenchyme: a microenvironment that promotes differentiation of pulmonary epithelium." Tissue Engineering 11(78):1177-1187 (2005).

Wang et al. "A pure population of lung alveolar epithelial type II cells derived from human embryonic stem cells." PNAS104(11):4449-4454 (2007).

Warren et al. "Highly efficient reprogramming to pluripotency and directed differentiation of human cells with synthetic modified mRNA." Cell Stem Cell 7:618-630 (2010).

Watanabe et al. "Directed differentiation of telencephalic precursors from embryonic stem cells." Nature Neuroscience 8:288-296 (2005).

Weaver et al. "Bmp signaling regulates proximal-distal differentiation of endoderm in mouse lung development." Development (Cambridge, England) 126:4005-4025 (1999).

Yabut et al., Aging 3(5):494-508 (2011). "The promise of human embryonic stem cells in aging-associated diseases."

Yaguchi et al., J National Cancer Institute 98(8):545-556 (2006). "Antitumor activity of ZSTK474, a new phophatidylinositol 3-kinase inhibitor."

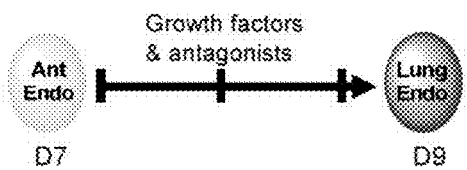
FIG. 3A
| | Growth factors & antagonists | Concentrations |
|---|---|---|
| 1 | Medium | N/A |
| 2 | BMP4 | 10 ng/ml |
| 3 | BMP4 | 20 ng/ml |
| 4 | BMP4 | 100 ng/ml |
| 5 | BMP4 + Dorsomorphin | 10 ng/ml + 5 µM |
| 6 | BMP4 + PD98059 | 10 ng/ml + 1 µM |
| 7 | FGF2 | 20 ng/ml |
| 8 | FGF2 | 100 ng/ml |
| 9 | BMP4 + FGF2 | 10 ng/ml + 20 ng/ml |
| 10 | BMP4 + FGF2 | 10 ng/ml + 100 ng/ml |
| 11 | BMP4 + FGF2 + PD173074 | 10 ng/ml + 20 ng/ml + 1 µM |
| 12 | BMP4 + GSK3XV | 10 ng/ml + 10 nM |
| 13 | BMP4 + GSK3XV | 10 ng/ml + 500 nM |
| 14 | BMP4 + IWR-1 | 10 ng/ml + 1 µM |
| 15 | BMP4 + FGF2 + GSK3XV | 10 ng/ml + 20 ng/ml + 10 nM |
| 16 | BMP4 + FGF2 + GSK3XV | 20 ng/ml + 100 ng/ml + 10 nM |
FIG. 3B
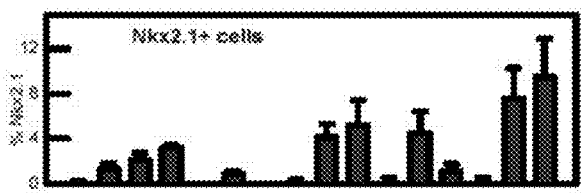
FIG. 3C Nkx2.1+, Tuj1-, Pax8-
↓
Nkx2.1+, Sox9+
↓
Nkx2.1+, Sox2+
↓
Nkx2.1+, p63+

FIG. 11A

Nkx2.1+, Tuj1-, Pax8-
↓          ↘
Nkx2.1+, Sox9+    Nkx2.1+, Sox2+
                      ⋮
                      ↓
                  Nkx2.1+, p63+

FIG. 11B

| Compound Name | % Nkx2.1 of total cells | Category |
| --- | --- | --- |
| Control | 10~25% | |
| GF-109203X | Up to 45% | PKC antagonist |
| Ro 31-8220 | Up to 70% | |
| Pp242 | Up to 45% | PI3K antagonist |
| PIK 75 | Up to 85% | |
| ZSTK474 | Up to 55% | |
| PMA etc | Up to 80% | MEK1/2 agonists |
| Carvedilol | Up to 50% | FDA Clinical drugs |
| Corticosterone | Up to 50% | |
| Triclabendazole | Up to 80% | |
| Benproperine Phosphate | Up to 85% | |
| Phenothiazine | Up to 85% | |
| Methotrexate | Up to 85% | |

FIG. 14B

ISOLATED HUMAN LUNG PROGENITOR CELLS AND USES THEREOF

CROSS-REFERENCE TO RELATED APPLICATIONS

This application is a Divisional Application of U.S. application Ser. No. 14/371,627, filed on Jul. 10, 2014, which is a 35 U.S.C. § 371 National Stage Application of International Application No. PCT/US2013/021186, filed on Jan. 11, 2013, which designates the United States, and which claims benefit under 35 U.S.C. § 119(e) of U.S. Provisional Application No. 61/619,568, filed on Apr. 3, 2012, and U.S. Provisional Application No. 61/586,551, filed on Jan. 13, 2012, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Sep. 13, 2017, is named 030258-072937-US-DIV_SL.txt and is 630 bytes bytes in size.

FIELD OF THE INVENTION

The field of the invention relates to isolated human lung progenitor cells, methods of making such isolated human lung progenitor cells and uses thereof.

BACKGROUND

Lung diseases, including respiratory diseases, are a major cause of mortality and morbidity worldwide. Current treatments are directed to reducing symptoms of lung disease and offer little to no prospect of cure or complete disease reversal.

Transplantation of pulmonary progenitor cells derived from stem cells is one approach that can be used to regenerate endogenous lung cells destroyed by injury and disease. Considerable interest has developed in the potential use of stem cells to repair lung epithelium destroyed by injury and disease.

Stem cells represent unique cell populations that have the ability to undergo both self-renewal and differentiation. It is beneficial to be able to isolate and purify precursor cells from a subject that can be manipulated before being reintroduced into the subject for treatment purposes. The use of a subject's own cells would obviate the need to employ adjunct immunosuppressive therapy, thereby maintaining the competency of the subject's immune system. For example, the directed differentiation of induced pluripotent stem cells generated from a subject's somatic cell sample provides advantages in providing populations of cells for autologous regenerative cell therapy.

SUMMARY

Cellular differentiation is a complex process typically occurring through many cell divisions. A partially or fully differentiated cell can be derived from a multipotent cell which itself is derived from a multipotent cell, and so on. While each of these multipotent cells can be considered stem cells, the range of cell types each can give rise to can vary considerably. Some differentiated cells also have the capacity to give rise to cells of greater developmental potential (e.g., reprogramming). Such capacity can be natural or can be induced artificially upon treatment with various factors. In many biological instances, stem cells are also "multipotent" because they can produce progeny of more than one distinct cell type, but this is not required for "stem-ness."

In addition to the capacity to differentiate to a more specific developmental phenotype, self-renewal is another classical part of the stem cell definition. In theory, self-renewal can occur by either of two major mechanisms. Stem cells may divide asymmetrically, with one daughter retaining the stem state and the other daughter expressing some distinct other specific function and phenotype. Alternatively some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation" by persons of ordinary skill in the art. Reversal of the differentiation phenotype in this manner generally requires artificial manipulation of the cell, for example, by expressing stem cell specific mRNA or proteins (e.g., c-Myc, Klf4, Oct4, Sox2, among others) or by contacting a cell with a de-differentiation medium.

The methods and compositions provided herein relate, in part, to the generation of human progenitor cells committed to the lung lineage and uses of such cells for treatment of lung diseases/disorders or injury to the lung. Whether an adult stem cell can be isolated from human adult lung remains controversial in the art and at present, methods for isolating and using adult lung stem cells from humans lack reproducibility. Thus, the methods and compositions described herein are advantageous over the present state of knowledge in the art and permit the generation of human lung progenitor cells for treatment, tissue engineering, and screening assays.

One aspect disclosed herein relates to an isolated human Nkx2.1 positive, Sox2 positive proximal airway multipotent progenitor cell, or an enriched population of human Nkx2.1 positive, Sox2 positive proximal airway multipotent progenitor cells.

In one embodiment of this aspect, the cell is Tuj1 negative and Pax8 negative.

In another embodiment of this aspect, the cell is proliferative and differentiates into an airway basal stem cell, a ciliated cell, a Clara cell, a neuroendocrine cell, or a squamous epithelial cell under chosen differentiation conditions.

Also provided herein in another aspect is an isolated human Nkx2.1 positive, Sox9 positive, distal multipotent lung progenitor cell.

In one embodiment of this aspect, the cell is FoxP2 positive and/or ID2 positive. In another embodiment, the cell is ETV4/5 positive.

In another embodiment of this aspect, the cell is proliferative and differentiates into any epithelial lung cell when placed under chosen differentiation conditions.

In another embodiment of this aspect, the cell differentiates into an airway basal stem cell, a ciliated cell, a Clara cell, a mucin secreting goblet cell, a type I pneumocyte, a type II pneumocyte, a squamous epithelial cell, a bronchioalveolar stem cell, a bronchioalveolar duct junction stem cell, a migratory CK14+ cell, or a neuroendocrine cell when placed under chosen differentiation conditions.

Another aspect described herein relates to an isolated human Nkx2.1 positive, p63 positive multipotent airway basal stem cell, or an enriched population of isolated human Nkx2.1 positive, p63 positive multipotent airway basal stem cells.

In another embodiment of this aspect, the cell is proliferative and differentiates into a ciliated cell, a Clara cell, a mucin secreting goblet cell, or a basal cell when placed under chosen differentiation conditions.

In another embodiment of this aspect, the multipotent airway basal stem cell does not express a Clara cell marker, a ciliated cell marker, a neuroendocrine cell marker, or a squamous cell marker.

In another embodiment of this aspect, the cell is Sox2 positive.

In another embodiment of this aspect, the cell is CK5 positive and/or NGFR positive.

In another embodiment of this aspect and all other aspects described herein, the cell is a disease-specific cell.

Another aspect provided herein relates to a composition comprising an isolated human Nkx2.1 positive, Sox2 positive proximal airway multipotent progenitor cell and a scaffold.

In another embodiment of this aspect, the scaffold is implantable in a subject.

In another embodiment of this aspect, the cell is autologous to the subject into which the composition is being implanted.

In another embodiment of this aspect, the scaffold is biodegradable.

In another embodiment of this aspect, the scaffold comprises a natural fiber, a synthetic fiber, decellularized lung tissue, or a combination thereof.

In another embodiment of this aspect, the natural fiber is selected from the group consisting of collagen, fibrin, silk, thrombin, chitosan, chitin, alginic acid, hyaluronic acid, and gelatin.

In another embodiment of this aspect, the synthetic fiber is selected from the group consisting of: representative bio-degradable aliphatic polyesters such as polylactic acid (PLA), polyglycolic acid (PGA), poly(D,L-lactide-co-glycolide) (PLGA), poly(caprolactone), diol/diacid aliphatic polyester, polyester-amide/polyester-urethane, poly(valerolactone), poly(hydroxyl butyrate), polybutylene terephthalate (PBT), polyhydroxyhexanoate (PHH), polybutylene succinate (PBS), and poly(hydroxyl valerate).

In another embodiment of this aspect, the proximal airway multipotent progenitor cell is Tuj1 negative and/or Pax8 negative.

Another aspect described herein relates to a composition comprising an isolated human Nkx2.1 positive, Sox9 positive, distal multipotent lung progenitor cell and a scaffold.

In one embodiment of this aspect, the multipotent lung progenitor cell is FoxP2 positive and/or ID2 positive. In another embodiment, the cell is ETV4/5 positive.

In another embodiment of this aspect, the scaffold is implantable in a subject.

In another embodiment of this aspect, the cell is autologous to the subject into which the composition is being implanted.

In another embodiment of this aspect, the scaffold is biodegradable.

In another embodiment of this aspect, the scaffold comprises a natural fiber, a synthetic fiber, decellularized lung, or a combination thereof.

In another embodiment of this aspect, the natural fiber is selected from the group consisting of collagen, fibrin, silk, thrombin, chitosan, chitin, alginic acid, hyaluronic acid, and gelatin.

In another embodiment of this aspect, the synthetic fiber is selected from the group consisting of: representative bio-degradable aliphatic polyesters such as polylactic acid (PLA), polyglycolic acid (PGA), poly(D,L-lactide-co-glycolide) (PLGA), poly(caprolactone), diol/diacid aliphatic polyester, polyester-amide/polyester-urethane, poly(valerolactone), poly(hydroxyl butyrate), polybutylene terephthalate (PBT), polyhydroxyhexanoate (PHH), polybutylene succinate (PBS), and poly(hydroxyl valerate).

Another aspect described herein relates to a composition comprising an isolated human Nkx2.1 positive, p63 positive multipotent airway basal stem cell and a scaffold.

In one embodiment of this aspect, the airway basal stem cell is CK5 positive and/or NGFR positive.

In another embodiment of this aspect, the scaffold is implantable in a subject.

In another embodiment of this aspect, the cell is autologous to the subject into which the composition is being implanted.

In another embodiment of this aspect, the scaffold is biodegradable.

In another embodiment of this aspect, the scaffold comprises a natural fiber, a synthetic fiber, decellularized lung tissue, or a combination thereof.

In another embodiment of this aspect, the natural fiber is selected from the group consisting of collagen, fibrin, silk, thrombin, chitosan, chitin, alginic acid, hyaluronic acid, and gelatin.

In another embodiment of this aspect, the synthetic fiber is selected from the group consisting of: representative bio-degradable aliphatic polyesters such as polylactic acid (PLA), polyglycolic acid (PGA), poly(D,L-lactide-co-glycolide) (PLGA), poly(caprolactone), diol/diacid aliphatic polyester, polyester-amide/polyester-urethane, poly(valerolactone), poly(hydroxyl butyrate), polybutylene terephthalate (PBT), polyhydroxyhexanoate (PHH), polybutylene succinate (PBS), and poly(hydroxyl valerate).

In another embodiment of this aspect and all other aspects described herein, the cell is a disease-specific cell.

Also provided herein in another aspect are methods of generating a human lung progenitor cell or population of human lung progenitor cells that is Nkx2.1 positive, Tuj1 negative and Pax8 negative, the method comprising contacting a human foregut endoderm cell with FGF2, WNT and BMP4, each for a time and at a concentration sufficient to permit differentiation of said human foregut endoderm cell to an Nkx2.1 positive, Tuj1 negative, Pax8 negative lung progenitor cell.

In one embodiment of this aspect, the contacting step is performed for at least 2 days.

In another embodiment of this aspect, the method further comprises contacting the Nkx2.1 positive, Tuj1 negative, Pax8 negative lung progenitor cell with BMP7, FGF7, a WNT antagonist, and a MAPKK/ERK antagonist, each for a time and at a concentration sufficient to permit differentiation of the Nkx2.1 positive, Tuj1 negative, Pax8 negative lung progenitor cell to a Nkx2.1 positive, Sox2 positive proximal airway multipotent progenitor cell.

In another embodiment of this aspect, the Wnt antagonist comprises IWR-1.

In another embodiment of this aspect, the MAPKK/ERK antagonist comprises PD98059.

In another embodiment of this aspect, the contacting step is performed for at least 4 days.

In another embodiment of this aspect, the method further comprises contacting the Nkx2.1 positive, Tuj1 negative, Pax8 negative lung progenitor cell with BMP7, FGF7, a WNT antagonist, and a MAPKK/ERK antagonist each for a time and at a concentration sufficient to permit differentiation of the Nkx2.1 positive, Tuj1 negative, Pax8 negative lung progenitor cell to an Nkx2.1 positive, Sox9 positive distal multipotent lung progenitor cell.

In another embodiment of this aspect, the Wnt antagonist comprises IWR-1.

In another embodiment of this aspect, the MAPKK/ERK antagonist comprises PD98059.

In another embodiment of this aspect, the contacting step is performed for at least 4 days.

In another embodiment of this aspect, the culture of foregut endoderm cells are derived from embryonic stem (ES) cells or induced pluripotent stem cells (iPSCs).

In another embodiment of this aspect, the method further comprises contacting a culture of Nkx2.1 positive, Tuj1 negative, Pax8 negative cells with B27, BMP7, FGF7, and a WNT antagonist, each for a time and at a concentration sufficient to permit differentiation of said Nkx2.1 positive, Tuj1 negative, Pax8 negative lung progenitor cell to an Nkx2.1 positive, p63 positive multipotent airway basal stem cell.

In another embodiment of this aspect, the method further comprises contacting the culture of Nkx2.1 positive, Tuj1 negative, Pax8 negative cells with Noggin.

In another embodiment of this aspect, the contacting step is performed for at least 10 days.

Also provided herein in another aspect, are methods for treating a lung disease or disorder, or lung injury in a subject, the method comprising: administering a composition comprising an isolated human lung progenitor cell and a pharmaceutically acceptable carrier to a subject having a lung disease or disorder, or lung injury.

In one embodiment of this aspect, the isolated human lung progenitor cell is selected from the group consisting of: an Nkx2.1 positive, Sox2 positive proximal airway multipotent progenitor cell; an Nkx2.1 positive, Sox9 positive distal multipotent lung progenitor cell, an Nkx2.1 positive, p63 positive multipotent airway basal stem cell, or a differentiated cell thereof.

In another embodiment of this aspect, the proximal airway multipotent progenitor cell is Tuj1 negative and/or Pax8 negative.

In another embodiment of this aspect, the distal multipotent lung progenitor cell is FoxP2 and/or ID2 positive. In another embodiment, the cell is ETV4/5 positive.

In another embodiment of this aspect, the airway basal stem cell is CK5 positive and/or NGFR positive.

In another embodiment of this aspect, the composition is administered to the lung.

In another embodiment of this aspect, the isolated human lung progenitor cell is autologous to the subject to which the composition is being administered.

In another embodiment of this aspect, the composition further comprises a scaffold.

In another embodiment of this aspect, the scaffold is implantable in a subject.

In another embodiment of this aspect, the scaffold is biodegradable.

In another embodiment of this aspect, the scaffold comprises a natural fiber, a synthetic fiber, decellularized lung tissue, or a combination thereof.

In another embodiment of this aspect, the scaffold comprises an agent that promotes differentiation of the isolated human lung progenitor cell.

In another embodiment of this aspect, the composition is formulated for aerosol delivery.

Another aspect provided herein relates to methods of screening for an agent to treat a lung disease or disorder, the method comprising: (a) culturing a population of human disease-specific airway cells produced by in vitro differentiation of a human disease specific lung progenitor cell in the presence and absence of a candidate agent for treating a lung disease or disorder, (b) comparing the expression or activity of at least one marker that is upregulated in the disease or comparing the expression or activity of at least one marker that is downregulated in the disease in the presence and absence of the candidate agent, wherein a decrease in the expression or activity of at least one upregulated disease marker or an increase in the expression or activity of at least one downregulated disease marker identifies the candidate agent as a candidate for the treatment of the lung disease or disorder in a subject.

In one embodiment of this aspect, the method further comprises steps before step (a) of differentiating a population of isolated human disease-specific lung progenitor cells to a culture of human disease-specific airway cells.

In another embodiment of this aspect, the method further comprises steps before step (a) of differentiating a population of induced pluripotent stem cells derived from a subject having a lung disease or disorder to a population of isolated human disease-specific lung progenitor cells.

In another embodiment of this aspect, the candidate agent comprises a small molecule, a protein, a polypeptide, an antibody or an antigen binding fragment thereof, or a nucleic acid.

In another embodiment of this aspect, the human lung progenitor cell is selected from the group consisting of: a human Nkx2.1 positive, Sox2 positive proximal airway multipotent progenitor cell, a human Nkx2.1 positive, Sox9 positive distal multipotent lung progenitor cell, and a human Nkx2.1 positive, p63 positive multipotent airway basal stem cell.

In another embodiment of this aspect, the human Nkx2.1 positive, Sox2 positive proximal airway multipotent progenitor cell, and the human Nkx2.1 positive, Sox9 positive distal multipotent lung progenitor cell are made by a method comprising contacting an Nkx2.1 positive, Tuj1 negative, Pax8 negative lung progenitor cell with BMP7, FGF7, a WNT antagonist, and a MAPKK/ERK antagonist each for a time and at a concentration sufficient to permit the Nkx2.1 positive, Tuj1 negative, Pax8 negative lung progenitor cell to differentiate to an Nkx2.1 positive, Sox9 positive proximal airway multipotent progenitor cell, or to an Nkx2.1 positive, Sox9 positive distal multipotent lung progenitor cell.

In another embodiment of this aspect, the contacting step is performed for at least 4 days.

In another embodiment of this aspect, the human Nkx2.1 positive, p63 positive multipotent airway basal stem cell is made by a method comprising contacting an Nkx2.1 positive, Tuj1 negative, Pax8 negative cell with B27, BMP7, FGF7, and a WNT antagonist, each for a time and at a concentration sufficient to permit differentiation of said Nkx2.1 positive, Tuj1 negative, Pax8 negative lung progenitor cell to an Nkx2.1 positive, p63 positive multipotent airway basal stem cell.

In another embodiment of this aspect, the method further comprises contacting the Nkx2.1 positive, Tuj1 negative, Pax8 negative cell with Noggin.

In another embodiment of this aspect, the contacting step is performed for at least 10 days.

Another aspect provided herein relates to methods of screening for an agent to induce differentiation of a human lung progenitor cell, the method comprising: (a) culturing an Nkx2.1 positive, Tuj1 negative, Pax8 negative human lung progenitor cell in the presence and absence of a candidate differentiation agent, (b) comparing the expression or activity of at least one marker that is upregulated during differentiation of the lung progenitor cell to a more differentiated state or comparing the expression or activity of at least one marker that is downregulated during differentiation of the lung progenitor cell to a more differentiated state in the presence and absence of the candidate agent, wherein a decrease in the expression or activity of at least one upregulated differentiation marker or an increase in the expression or activity of at least one downregulated differentiation marker is indicative that the candidate agent can be used to induce differentiation of an isolated human lung progenitor cell in a subject.

In one embodiment of this aspect, the method further comprises steps before step (a) of differentiating an embryonic stem cell or induced pluripotent stem cell to a human lung progenitor cell.

In another embodiment of this aspect, the candidate agent comprises a small molecule, a protein, a polypeptide, an antibody, or a nucleic acid.

In another embodiment of this aspect, the human lung progenitor cell is selected from the group consisting of: a human Nkx2.1 positive, Sox2 positive proximal airway multipotent progenitor cell, a human Nkx2.1 positive, Sox9 positive distal multipotent lung progenitor cell, and a human Nkx2.1 positive, p63 positive multipotent airway basal stem cell.

In another embodiment of this aspect, the human Nkx2.1 positive, Sox2 positive proximal airway multipotent progenitor cell, and the human Nkx2.1 positive, Sox9 positive distal multipotent lung progenitor cell are made by a method comprising contacting an Nkx2.1 positive, Tuj1 negative, Pax8 negative human lung progenitor cell with BMP7, FGF7, a WNT antagonist, and a MAPKK/ERK antagonist each for a time and at a concentration sufficient to permit the Nkx2.1 positive, Tuj1 negative, Pax8 negative lung progenitor cell to differentiate to an Nkx2.1 positive, Sox9 positive proximal airway multipotent progenitor cell, or to an Nkx2.1 positive, Sox9 positive distal multipotent lung progenitor cell.

In another embodiment of this aspect, the contacting step is performed for at least 4 days.

In another embodiment of this aspect, the human Nkx2.1 positive, p63 positive multipotent airway basal stem cell is made by a method comprising contacting an Nkx2.1 positive, Tuj1 negative, Pax8 negative cell with B27, BMP7, FGF7, and a Wnt antagonist, each for a time and at a concentration sufficient to permit differentiation of the Nkx2.1 positive, Tuj1 negative, Pax8 negative lung progenitor cell to an Nkx2.1 positive, p63 positive multipotent airway basal stem cell.

In another embodiment of this aspect, further comprising contacting the Nkx2.1 positive, Tuj1 negative, Pax8 negative cell with Noggin.

In another embodiment of this aspect, the contacting step is performed for at least 10 days.

Another aspect provided herein relates to kits for treating a lung disease or disorder, the kit comprising: a cell of claim 1, 5, or 9, a pharmaceutically acceptable carrier, and instructions for treating a lung disease or disorder.

In one embodiment of this aspect, the kit further comprises a scaffold.

Also provided herein, in another aspect, is a kit for screening a candidate agent, the kit comprising: a cell of claim 1, 5, or 8, one or more agents for detecting lung specific cell surface markers, and instructions therefore.

In one embodiment of this aspect, the kit further comprises a cell culture medium, a growth factor, and/or a differentiation agent.

Another aspect provided herein relates to a kit(s) for differentiating a human stem cell to a human lung progenitor cell, the kit comprising: (i) two or more of BMP4, FGF2, WNT, BMP7, FGF7, a WNT antagonist, Noggin, B27, and retinoic acid, optionally provided in unit doses; (ii) optionally, a cell culture medium; (iii) one or more agents for detecting a lung cell-specific surface marker; and (iii) instructions therefore.

Also provided herein is a cell or tissue culture medium for generating definitive endoderm from an iPSC or ESC, comprising: B27, Activin A, and ZSTK474. In one embodiment, the medium comprises B27 in a concentration of 1%-5% (e.g., 2%). In another embodiment, the medium comprises Activin A in a concentration of 10-40 ng/mL (e.g., 20 ng/mL). In another embodiment, the medium comprises ZSTK474 in a concentration of 0.2-0.5 µM. In another embodiment, the base of the medium comprises the components of RPMI medium.

Also provided herein is a cell or tissue culture medium for generating an Nkx2.1 positive lung progenitor cell, comprising: CHIR9902, PIK-75, Dorsomorphin, and FGF2. In one embodiment, the medium comprises CHIR9902 in a concentration of 0.1-1 µM. In another embodiment, the medium comprises PIK-75 in a concentration of 0.01-0.1 µM. In another embodiment, the medium comprises dorsomorphin in concentration of 1-5 µM. In another embodiment, the medium comprises, FGF2 in a concentration of 10-100 ng/mL. In another embodiment, the medium further comprises a drug selected from the group consisting of: GF-109203X, Ro31-8220, Pp242, PIK-75, ZSTK474, PMA, carvedilol, corticosterone, triclabendazole, benproperine phosphate, phenothiazine, and methotrexate.

Also provided herein is a method of generating a human lung progenitor cell or population of human lung progenitor cells that is Nkx2.1 positive, Tuj1 negative, and Pax8 negative, the method comprising contacting a human foregut endoderm cell with a Wnt agonist, a PIK3 kinase inhibitor, a BMP antagonist, and a drug selected from the group consisting of GF-109203X, Ro31-8220, Pp242, PIK-75, ZSTK474, PMA, carvedilol, corticosterone, triclabendazole, benproperine phosphate, phenothiazine, and methotrexate, each for a time and at a concentration sufficient to permit differentiation of said human foregut endoderm cell to an Nkx2.1 positive, Tuj1 negative, Pax8 negative lung progenitor cell.

In one embodiment, the contacting step is performed for at least 2 days.

In another embodiment, the Wnt agonist comprises CHIR9902. In another embodiment, the concentration of CHIR9902 is in the range of 0.1-1 µM.

In another embodiment, the PI3 kinase inhibitor comprises PIK-75. In another embodiment, the concentration of PIK-75 comprises 0.01-0.1 µM.

In another embodiment, the BMP antagonist comprises Dorsomorphin. In another embodiment, the concentration of dorsomorphin comprises 1-5 µM.

In another embodiment, the growth factor comprises FGF2. In another embodiment, the concentration of FGF2 comprises 10-100 ng/mL.

Also provided herein in another aspect is a method for generating a definitive endoderm cell or population of definitive endoderm cells, the method comprising contacting an iPSC or ESC with B27, Activin A, and ZSTK474, each for a time and at a concentration sufficient to permit differentiation of the iPSC or ESC to a definitive endoderm cell.

In one embodiment, generation of a definitive endoderm cell is determined by FOXA2/SOX17 co-staining or by FACS analysis with cKit/CXCR4 and/or cKit/EpCAM combination.

In another embodiment, the concentration of B27 comprises 1%-5% (e.g., 2%).

In another embodiment, the concentration of Activin A is 10-40 ng/mL (e.g., 20 ng·mL In another embodiment, the concentration of ZSTK474 is 0.2-0.5 µM.

BRIEF DESCRIPTION OF THE FIGURES

FIG. 2A shows administration of 20 ng/ml BMP4, 20 ng/ml FGF2 and 5 nM GSK3iXV to definitive endoderm resulted in hindgut differentiation with CDX2 expression, and minimal NKX2.1 induction. Scale bar, 50 µm. FIG. 2B shows the treatment of definitive endoderm with different combinations of BMP4/TGFβ agonists and antagonists as listed in the table for 2 days. The Foxa2+/Sox2+ cells were quantified as a percentage of positive cells out of the total number of Foxa2+ cells. The cells were further treated with 20 ng/ml BMP4, 20 ng/ml FGF2 and 5 nM GSK3iXV to induce NKX2.1 expression. The percentage of Nkx2.1+ cells was quantified as a percentage of the total cells present. All data were averaged from 3 independent experiments.

FIG. 3A, FIG. 3B, and FIG. 3C show that BMP4, FGF2 and WNT signaling are necessary for lung specification from foregut endoderm cells. FIG. 3A is a schematic depicting the strategy and time frame to generate Nkx2.1+ cells from foregut endoderm cells. FIG. 3B is a list of various combinations of BMP4, FGF2, WNT and their antagonists for Nkx2.1+ induction. FIG. 3C shows the NKX2.1 percentage as scored by the number of Nkx2.1+ cells out of the total cell number in an average of 3 independent experiments.

FIG. 4 shows that signaling of BMPs through SMAD-dependent pathways is required for lung Nkx2.1+ differentiation. In contrast, signaling through the MAP kinase pathway is not required for Nkx2.1 expression. Dorsomorphin inhibits BMP signaling through the SMAD pathway while PD98059 inhibits MAPK signaling.

FIG. 5A is a schematic depicting a strategy and time line to generate embryonic airway progenitors from multipotent lung endoderm cells. FIG. 5B is a summary of signaling switches that are distinct in the proximal airway and the distal lung bud tip during the pseudoglandular stage of lung development. Immunofluorescence staining of NKX2.1 and SOX2 was performed after treatment of Nkx2.1+ lung endoderm cells at D9 with medium containing RA-supplemented B27, 20 ng/ml BMP7, 20 ng/ml FGF7, 100 nM IWR-1 (WNT antagonist), and 100 ng/ml Noggin for 2 days (data not shown). In addition, immunofluorescence staining of NKX2.1 and SOX2 was performed after treatment of Nkx2.1+ lung endoderm cells at D9 with medium containing RA-supplemented B27, 20 ng/ml BMP7, 20 ng/ml FGF7, 100 nM IWR-1 (WNT antagonist), and 1 µM PD98059 for 2 day. Scale bar, 50 µm (data not shown). Data from the immunofluorescence staining indicated the presence of a subpopulation of Nkx2.1+ cells positive for P63 (data not shown).

FIG. 11A and FIG. 11B is a schematic depicting differentiation possibilities for Nkx2.1+, Tuj1−, Pax8− cells. Without wishing to be bound by theory, FIG. 11A and FIG. 11B show two possible mechanisms by which downstream human lung progenitors can be differentiated from Nkx2.1+, Tuj1−, Pax8− cells.

FIG. 14A and FIG. 14B show unbiased chemical screening to enhance lung differentiation from anterior endoderm. FIG. 14A shows a schematic diagram depicting the chemical screening platform. FIG. 14B is a table showing the lead compounds that facilitated the production of Nkx2.1+ lung progenitor cells.

DETAILED DESCRIPTION

Figure 1:
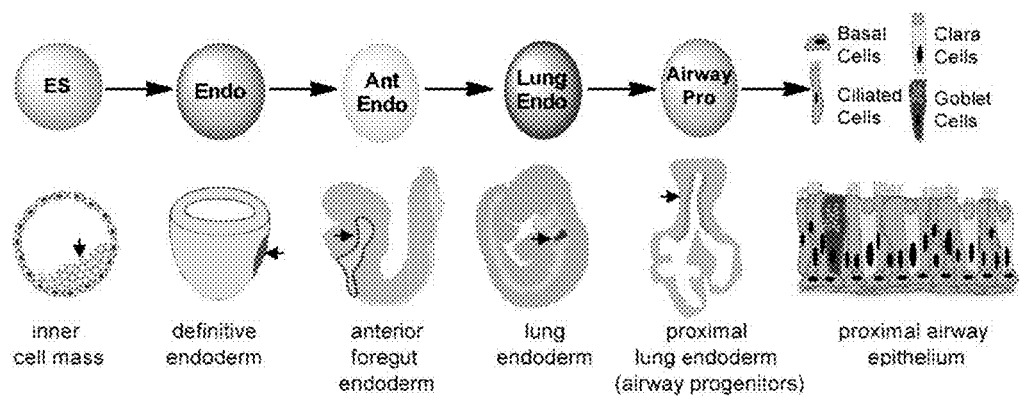
FIG. 1 is a schematic depicting an overall strategy for the step-wise differentiation of airway progenitors from mouse ESCs. The schematic shows the approach to develop an efficient and reproducible protocol to produce embryonic airway epithelial progenitors from mouse ESCs. The signaling network promotes the differentiation of ESCs into definitive endoderm, the anteriorization of endoderm into foregut endoderm, the induction of the earliest lung endoderm from foregut endoderm, and the generation of embryonic airway progenitor cells.

The compositions and methods described herein are related, in part, to the discovery of a method for making isolated human lung progenitor cells from embryonic stem (ES) cells or induced pluripotent stem cells (iPSCs). The presence and isolation of adult progenitor cells from lung tissue is controversial and has achieved only limited success, therefore the methods and compositions described herein have the advantage that isolated human lung progenitor cells can be produced in quantities useful for screening assays or treatment of lung diseases/disorders or lung injury. Further, the cell compositions provided herein have not been previously isolated and/or cultured from human lung tissue.

Definitions

As used herein the term "human stem cell" refers to a human cell that can self-renew and differentiate to at least one cell type. The term "human stem cell" encompasses human stem cell lines, human-derived iPS cells, human embryonic stem cells, human pluripotent cells, human multipotent stem cells or human adult stem cells.

As used herein, the term "multipotent" refers to the ability of a cell to differentiate into a plurality of different phenotypes. Multipotent cells can generally only differentiate into cells of a single germ layer lineage. This is in contrast to pluripotent cells which can, by definition, differentiate into cells of all three germ layers. Pluripotent cells are characterized primarily by their ability to differentiate into all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. A pluripotent cell typically has the potential to divide in vitro for a long period of time, e.g., greater than one year or more than 30 passages.

As used herein, the term "human lung progenitor cell" is a general term that refers to any progenitor cell that is committed to the pulmonary lineage and also retains the ability to self-renew. One of the first steps in commitment to the lung lineage is the appearance of the stem cell marker Nkx2.1, however the Nkx2.1 marker can also be detected in cells of the thyroid and brain lineage. Therefore, for the purposes of this description, the first progenitor cells committed to the lung lineage and encompassed by the term "human lung progenitor cell" are those cells that express Nkx2.1, but lack Tuj1 and Pax8 cell surface markers. Any progenitor cell that can be differentiated from the Nkx2.1 positive, Tuj1 negative, Pax8 negative cell and that retains the ability to self-renew is also encompassed by the term "human lung progenitor cell." Other examples of human lung progenitor cells described herein include, but are not limited to, Nkx2.1 positive, Sox2 positive proximal multipotent airway progenitor cells; Nkx2.1 positive, Sox9 positive distal multipotent lung progenitor cells; and Nkx2.1 positive, p63 positive basal airway stem cells. In some embodiments, the human lung progenitor cells are differentiated into an airway basal stem cell, a ciliated cell, a Clara cell, a mucin secreting goblet cell, a type I pneumocyte, a type II pneumocyte or a neuroendocrine cell when placed under selected differentiation conditions. A human lung progenitor cell is not a tumor cell or a cancer cell. In one aspect, a human lung progenitor cell is not derived from an embryo or from an embryonic stem cell or other cell derived in culture from an embryo. In some embodiments, the human lung progenitor cells are differentiated from an autologous cell or from a non-autologous cell. In one embodiment, the human lung progenitor cell is not genetically modified or derived from a genetically modified cell.

As used herein, the term "distal multipotent lung progenitor cell" refers to an Nkx2.1 positive, Sox9 positive cell that can differentiate into all types of epithelial cells of the lung including, but not limited to, an airway basal stem cell, a ciliated cell, a Clara cell, a neuroendocrine cell, a squamous epithelial cell, a type I pneumocyte, a type II pneumocyte, a bronchioalveolar stem cell (BASC), lung progenitors located in the bronchioalveolar duct junction (BADJ) within the terminal bronchioles, progenitor cells for type I and type II pneumocytes, and/or a migratory CK14+ cell for both airway epithelial cells and alveolar cells that respond to lung injury (e.g., flu infection).

As used herein, the term "proximal airway multipotent progenitor" refers to an Nkx2.1 positive, Sox2 positive cell that can differentiate into an airway basal stem cell, a ciliated cell, a Clara cell, a neuroendocrine cell, a squamous epithelial cell, or a migratory CK14+ cell that moves to a bronchioalveolar location for alveolar cell differentiation after a lung injury.

By the term "differentiated cell" is meant any primary cell that is not, in its native form, pluripotent as that term is defined herein. Those of ordinary skill in the art recognize that there is a spectrum of differentiation from totipotent or pluripotent cells at one end to fully differentiated cells that do not have the normal capacity to naturally differentiate to any other phenotype. Thus, a pluripotent cell is differentiated relative to a totipotent cell, and a multipotent cell is differentiated relative to a pluripotent cell. In some embodiments, the term "differentiated cell" also refers to a cell of a more specialized cell type derived from a cell of a less specialized cell type (e.g., from an undifferentiated cell or a reprogrammed cell) where the cell has undergone a cellular differentiation process.

As used herein, the term "positive for" when referring to a cell positive for a marker (e.g., Nkx2.1 positive) means that a cell surface marker is detectable above background levels on the cell using immunofluorescence microscopy or flow cytometry methods, such as fluorescence activated cell sorting (FACS). Alternatively, the terms "positive for" or "expresses a marker" means that expression of mRNA encoding a cell surface or intracellular marker is detectable above background levels using RT-PCR. The expression level of a cell surface marker or intracellular marker can be compared to the expression level obtained from a negative control (i.e., cells known to lack the marker) or by isotype controls (i.e., a control antibody that has no relevant specificity and only binds non-specifically to cell proteins, lipids or carbohydrates). Thus, a cell that "expresses" a marker (or is "positive for a marker") has an expression level detectable above the expression level determined for the negative control for that marker.

As used herein, the term "negative for" when referring to a cell negative for a marker (or the term "does not express") means that a cell surface marker cannot be detected above background levels on the cell using immunofluorescence microscopy or flow cytometry methods, such as fluorescence activated cell sorting (FACS). Alternatively, the terms "negative" or "does not express" means that expression of the mRNA for an intracellular marker or cell surface marker cannot be detected above background levels using RT-PCR. The expression level of a cell surface marker or intracellular marker can be compared to the expression level obtained from a negative control (i.e., cells known to lack the marker) or by isotype controls (i.e., a control antibody that has no relevant specificity and only binds non-specifically to cell proteins, lipids or carbohydrates). Thus, a cell that "does not express" a marker appears similar to the negative control for that marker.

As used herein, the phrase "cell is proliferative" refers to the ability of a stem cell to self-renew. Self-renewal can occur by either of two major mechanisms. Stem cells can divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only.

As used herein, the term "capacity to differentiate" refers to the ability of a stem cell, progenitor cell, pluripotent cell, or multipotent cell to differentiate into a subset of more differentiated cells. The term "capacity to differentiate" does not encompass moving backwards along the differentiation spectrum such that a cell is produced that comprises a greater differentiation capacity than the parent cell. That is, the term "capacity to differentiate" does not encompass re-programming methods to shift cells to a less differentiated state.

In the context of cell ontogeny, the term "differentiate", or "differentiating" is a relative term that indicates a "differentiated cell" is a cell that has progressed further down the developmental pathway than its precursor cell. Thus in some embodiments, a reprogrammed cell as this term is defined herein, can differentiate to lineage-restricted precursor cells (such as a human lung progenitor cell), which in turn can differentiate into other types of precursor cells further down the pathway (such as a tissue specific precursor, for example, a proximal airway multipotent progenitor cell), and then to an end-stage differentiated cell, which plays a characteristic role in a certain tissue type, and may or may not retain the capacity to proliferate further.

As used herein, the terms "dedifferentiation" or "reprogramming" or "retrodifferentiation" refer to the process that generates a cell that re-expresses a more stem cell phenotype or a less differentiated phenotype than the cell from which it is derived. For example, a multipotent cell can be dedifferentiated to a pluripotent cell. That is, dedifferentiation shifts a cell backward along the differentiation spectrum of totipotent cells to fully differentiated cells. Typically, reversal of the differentiation phenotype of a cell requires artificial manipulation of the cell, for example, by expressing stem cell-specific mRNA and/or proteins. Reprogramming is not typically observed under native conditions in vivo or in vitro.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cells forming the body of an organism, as opposed to germline cells. Every cell type in the mammalian body—apart from the sperm and ova, the cells from which they are made (gametocytes) and undifferentiated stem cells—is a somatic cell: internal organs, skin, bones, blood, and connective tissue are all substantially made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for reprogramming a differentiated cell (e.g., to generate an iPSC) can be performed both in vivo and in vitro (where in vivo is practiced when a differentiated cell is present within a subject, and where in vitro is practiced using an isolated differentiated cell maintained in culture).

As used herein, the term "adult cell" refers to a cell found throughout the body after embryonic development.

The term "isolated cell" as used herein refers to a cell that has been removed from an organism in which it was originally found, or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched. In some embodiments, the isolated population is an isolated population of human lung progenitor cells, e.g., a substantially pure population of human lung progenitor cells as compared to a heterogeneous population of cells comprising human lung progenitor cells and cells from which the human lung progenitor cells were derived.

The term "substantially pure," with respect to a particular cell population, refers to a population of cells that is at least about 75%, preferably at least about 85%, more preferably at least about 90%, and most preferably at least about 95% pure, with respect to the cells making up a total cell population. That is, the terms "substantially pure" or "essentially purified," with regard to a population of lung progenitor cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not lung progenitor cells as defined by the terms herein.

The terms "enriching" or "enriched" are used interchangeably herein and mean that the yield (fraction) of cells of one type, such as human lung progenitor cell compositions and cells for use in the methods described herein, is increased by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, or by at least 75%, over the fraction of cells of that type in the starting biological sample, culture, or preparation.

As used herein, "proliferating" and "proliferation" refer to an increase in the number of cells in a population (growth) by means of cell division. Cell proliferation is generally understood to result from the coordinated activation of multiple signal transduction pathways in response to the environment, including growth factors and other mitogens. Cell proliferation can also be promoted by release from the actions of intra- or extracellular signals and mechanisms that block or negatively affect cell proliferation.

The terms "renewal" or "self-renewal" or "proliferation" are used interchangeably herein, and refers to a process of a cell making more copies of itself (e.g. duplication) of the cell. In some embodiments, lung progenitor cells are capable of renewal of themselves by dividing into the same undifferentiated cells (e.g. as determined by measuring the presence of absence of one or more cell surface markers) over long periods, and/or many months to years. In some instances, proliferation refers to the expansion of lung progenitor cells by the repeated division of single cells into two identical daughter cells.

The term "separation" or "selection" as used herein refers to isolating different cell types into one or more populations and collecting the isolated population as a target cell population which is enriched in a specific target stem cell population. Selection can be performed using positive selection, whereby a target enriched cell population is retained, or negative selection, whereby non-target cell types are discarded (thereby enriching for desired target cell types in the remaining cell population).

The term "positive selection" as used herein refers to selection of a desired cell type by retaining the cells of interest. In some embodiments, positive selection involves the use of an agent to assist in retaining the cells of interest, e.g., use of a positive selection agent such as an antibody which has specific binding affinity for a surface antigen on the desired or target cell. In some embodiments, positive selection can occur in the absence of a positive selection agent, e.g., in a "touch-free" or closed system, for example, where positive selection of a target cell type is based on any of cell size, density and/or morphology of the target cell type.

The term "negative selection" as used herein refers to selection of undesired or non-target stem cells for depletion or discarding, thereby retaining (and thus enriching) the desired target cell type. In some embodiments, negative selection involves the use of an agent to assist in selecting undesirable cells for discarding, e.g., use of a negative selection agent such as a monoclonal antibody which has specific binding affinity for a surface antigen on unwanted or non-target cells. In some embodiments, negative selection does not involve a negative selection agent. In some embodiments, negative selection can occur in the absence of a negative selection agent, e.g., in a "touch-free" or closed system, for example, where negative selection of an undesired (non-target) cell type to be discarded is based on any of cell size, density and/or morphology of the undesired (non-target) cell type.

The term "marker" as used herein is used to describe the characteristics and/or phenotype of a cell. Markers can be used for selection of cells comprising characteristics of interest and can vary with specific cells. Markers are characteristics, whether morphological, functional or biochemical (enzymatic) characteristics of the cell of a particular cell type, or molecules expressed by the cell type. In one aspect, such markers are proteins. Such proteins can possess an epitope for antibodies or other binding molecules available in the art. However, a marker can consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method available to one of skill in the art. Markers can also be the absence of a morphological characteristic or absence of proteins, lipids etc. Markers can be a combination of a panel of unique characteristics of the presence and/or absence of polypeptides and other morphological characteristics. In one embodiment, the marker is a cell surface marker. Exemplary cell surface markers expressed on lung progenitor cells include, but are not limited to, Sox2, Sox9, p63, FoxP2, ETV4/5, FoxA2, Nkx2.1, Gata6, ID2, CK5, NGFR, FoxJ1, CCSP, Scgb3a2, Muc5ac, T1a, Spc, and Scgn. In some embodiments, the absence of a cell surface marker can be used to distinguish a lung progenitor cell from a cell of another lineage (e.g., a thyroid or brain lineage). Exemplary cell surface markers that are absent on lung progenitor cells or differentiated lung cells include, but are not limited to, Tuj1, and Pax8. One of skill in the art will recognize that a cell surface marker can be present at a particular point in development or in a particular lung progenitor cell type. For example, Sox2 is expressed in progenitor cells of the anterior endoderm, is not expressed in more differentiated lung progenitors, such as distal multipotent lung progenitors, and then is reactivated in cells such as airway progenitors as differentiation of the progenitors progresses. Thus, a cell surface marker can be used in combination with a positive selection strategy for certain lung progenitors and also used as in combination with a negative selection strategy for other lung progenitors, depending on the particular differentiation stage of the desired lung progenitor to be selected.

As used herein, the term "scaffold" refers to a structure, comprising a biocompatible material, that provides a surface suitable for adherence and proliferation of cells. A scaffold can further provide mechanical stability and support. A scaffold can be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used herein, the term "implantable in a subject" refers to any non-living (e.g., acellular) implantable structure that upon implantation does not generate an appreciable immune response in the host organism. Thus, an implantable structure should not for example, be or contain an irritant, or contain LPS etc.

As used herein, the term "biodegradable" refers to the ability of a scaffold to degrade under physiological conditions, for example under conditions that do not adversely affect cell viability of the delivered cells or cells in vivo. Such biodegradable scaffolds will preferably not be or contain an irritant or an allergen that can cause a systemic reaction in the subject to which the composition has been implanted. In some embodiments, biodegradable means that the scaffold can be metabolized and the metabolites cleared from the subject by physiological excretion mechanisms (e.g., urine, feces, liver detoxification etc.).

As used herein, the term "treating" includes reducing or alleviating at least one adverse effect or symptom of a condition, disease or disorder. For example, the term "treating" and "treatment" refers to administering to a subject an effective amount of a composition, e.g., an effective amount of a composition comprising a population of lung progenitor cells so that the subject has a reduction in at least one symptom of the disease or an improvement in the disease, for example, beneficial or desired clinical results. For purposes of this disclosure, beneficial or desired clinical results include, but are not limited to, alleviation of one or more symptoms, diminishment of extent of disease, disease stabilization (e.g., not worsening), delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition, but may not be a complete cure for the disease. In some embodiments, treatment can include prophylaxis. However, in alternative embodiments, treatment does not include prophylaxis.

"Treatment" of a lung disorder, a lung disease, or a lung injury (e.g., acute lung injury) as referred to herein refers to therapeutic intervention that stabilizes or improves the function of the lung or the airway. That is, "treatment" is oriented to the function of the respiratory tract. A therapeutic approach that stabilizes or improves the function of the lung or the airway by at least 10%, and preferably by at least 20%, 30%, 40%, 50%, 75%, 90%, 100% or more, e.g., 2-fold, 5-fold, 10-fold or more, up to and including full function, relative to such function prior to such therapy is considered effective treatment. Effective treatment need not cure or directly impact the underlying cause of the lung disease or disorder to be considered effective treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used with the methods described herein that will be effective in the treatment of a particular disorder or condition will depend on the nature of the disorder or condition, and can be determined by standard clinical techniques.

As used herein, "prevention" or "preventing," when used in reference to a disease, disorder or symptoms thereof, refers to a reduction in the likelihood that an individual will develop a disease or disorder, e.g., a lung disorder. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 10% on a clinically accepted scale for that disease or disorder) or delayed (e.g., by days, weeks, months or years) symptoms is considered effective prevention.

As used herein, the term "induced to differentiate" refers to a chemical/biological treatment, a physical environment or a genetic modification that is conducive to the formation of more differentiated cells (e.g., human lung progenitor cells or cells having an airway phenotype) from pluripotent or multipotent stem cells (e.g., anterior foregut endoderm cells). Differentiation can be assessed by the appearance of distinct cell-type specific markers or by the loss of stem cell specific markers, or both.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Embryonic Stem Cells

Stem cells are cells that retain the ability to renew themselves through mitotic cell division and can differentiate into a diverse range of specialized cell types. Three broad types of mammalian stem cells include: embryonic stem (ES) cells that are found in blastocysts, induced pluripotent stem cells (iPSCs) that are reprogrammed from somatic cells, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues. Pluripotent stem cells can differentiate into cells derived from any of the three germ layers.

Stem cells are classified by their developmental potential as: (1) totipotent, which is able to give rise to all embryonic and extraembryonic cell types; (2) pluripotent, which is able to give rise to all embryonic cell types, i.e., endoderm, mesoderm, and ectoderm; (3) multipotent, which is able to give rise to a subset of cell lineages, but all within a particular tissue, organ, or physiological system (for example, multipotent distal lung progenitor cells can produce progeny that include multipotent distal lung progenitor cells (self-renewal) and the cell types and elements (e.g., basal cells, ciliated cells, Clara cells and goblet cells) that are normal components of the airway); (4) oligopotent, which is able to give rise to a more restricted subset of cell lineages than multipotent stem cells; and (5) unipotent, which is able to give rise to a single cell lineage (e.g., spermatogenic stem cells).

Provided herein are methods of generating human lung progenitor cells from both embryonic stem cells and induced pluripotent stem cells. In one embodiment, the methods provided herein relate to generation of human lung progenitor cells from embryonic stem cells. Alternatively, in some embodiments, the methods provided herein do not encompass generation of human lung progenitor cells from embryonic stem cells or any other cells of human embryonic origin.

Embryonic stem cells and methods of their retrieval are well known in the art and are described, for example, in Trounson A O (Reprod Fertil Dev (2001) 13: 523), Roach M L (Methods Mol Biol (2002) 185: 1), and Smith A G (Annu Rev Cell Dev Biol (2001) 17:435). The term "embryonic stem cell" is used to refer to the pluripotent stem cells of the inner cell mass of the embryonic blastocyst (see e.g., U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235,970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

Cells derived from embryonic sources can include embryonic stem cells or stem cell lines obtained from a stem cell bank or other recognized depository institution. Other means of producing stem cell lines include methods comprising the use of a blastomere cell from an early stage embryo prior to formation of the blastocyst (at around the 8-cell stage). Such techniques correspond to the pre-implantation genetic diagnosis technique routinely practiced in assisted reproduction clinics. The single blastomere cell is co-cultured with established ES-cell lines and then separated from them to form fully competent ES cell lines.

Embryonic stem cells are considered to be undifferentiated when they have not committed to a specific differentiation lineage. Such cells display morphological characteristics that distinguish them from differentiated cells of embryo or adult origin. Undifferentiated embryonic stem (ES) cells are easily recognized by those skilled in the art, and typically appear in the two dimensions of a microscopic view in colonies of cells with high nuclear/cytoplasmic ratios and prominent nucleoli. In some embodiments, the human lung progenitor cells described herein are not derived from embryonic stem cells or any other cells of embryonic origin.

Adult stem cells are stem cells, which are derived from tissues of a post-natal or post-neonatal organism or from an adult organism are also known in the art. An adult stem cell is structurally distinct from an embryonic stem cell not only in markers it does or does not express relative to an embryonic stem cell, but also by the presence of epigenetic differences, e.g. differences in DNA methylation patterns.

Induced Pluripotent Stem Cells (iPSCs)

In some embodiments, the human lung progenitor cells described herein are derived from isolated pluripotent stem cells. An advantage of using iPSCs is that the cells can be derived from the same subject to which the human lung progenitor cells are to be administered. That is, a somatic cell can be obtained from a subject, reprogrammed to an induced pluripotent stem cell, and then re-differentiated into a human lung progenitor cell to be administered to the subject (e.g., autologous cells). Since the lung progenitors are essentially derived from an autologous source, the risk of engraftment rejection or allergic responses is reduced compared to the use of cells from another subject or group of subjects. In some embodiments, the lung progenitors are derived from non-autologous sources. In addition, the use of iPSCs negates the need for cells obtained from an embryonic source. Thus, in one embodiment, the stem cells used in the disclosed methods are not embryonic stem cells.

Although differentiation is generally irreversible under physiological contexts, several methods have been recently developed to reprogram somatic cells to induced pluripotent stem cells. Exemplary methods are known to those of skill in the art and are described briefly herein below.

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods described herein can also be of use for such purposes, in some embodiments.

The specific approach or method used to generate pluripotent stem cells from somatic cells (broadly referred to as "reprogramming") is not critical to the claimed invention. Thus, any method that re-programs a somatic cell to the pluripotent phenotype would be appropriate for use in the methods described herein.

Reprogramming methodologies for generating pluripotent cells using defined combinations of transcription factors have been described induced pluripotent stem cells. Yamanaka and Takahashi converted mouse somatic cells to ES cell-like cells with expanded developmental potential by the direct transduction of Oct4, Sox2, Klf4, and c-Myc (Takahashi and Yamanaka, 2006). iPSCs resemble ES cells as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission (Maherali and Hochedlinger, 2008), and tetraploid complementation (Woltjen et al., 2009).

Subsequent studies have shown that human iPS cells can be obtained using similar transduction methods (Lowry et al., 2008; Park et al., 2008; Takahashi et al., 2007; Yu et al., 2007b), and the transcription factor trio, OCT4, SOX2, and NANOG, has been established as the core set of transcription factors that govern pluripotency (Jaenisch and Young, 2008). The production of iPS cells can be achieved by the introduction of nucleic acid sequences encoding stem cell-associated genes into an adult, somatic cell, historically using viral vectors.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30). Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell. In one embodiment, the methods and compositions described herein further comprise introducing one or more of each of Oct 4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors.

The efficiency of reprogramming (i.e., the number of reprogrammed cells) derived from a population of starting cells can be enhanced by the addition of various small molecules as shown by Shi, Y., et al (2008) *Cell-Stem Cell* 2:525-528, Huangfu, D., et al (2008) *Nature Biotechnology* 26(7):795-797, and Marson, A., et al (2008) *Cell-Stem Cell* 3:132-135. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Somatic Cells for Reprogramming:

Somatic cells, as that term is used herein, refer to any cells forming the body of an organism, excluding germline cells. Every cell type in the mammalian body—apart from the sperm and ova, the cells from which they are made (gametocytes) and undifferentiated stem cells—is a differentiated somatic cell. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, an hepatocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. In some embodiments, a somatic cell can be a primary cell isolated from any somatic tissue including, but not limited to brain, liver, lung, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of human lung progenitor cells to be used in the therapeutic treatment of disease, it is desirable, but not required, to use somatic cells isolated from the patient being treated. For example, somatic cells involved in diseases, and somatic cells participating in therapeutic treatment of diseases and the like can be used. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; β-III-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; β-catenin, and Bmi1. Such cells can also be characterized by the down-regulation of markers characteristic of the somatic cell from which the induced pluripotent stem cell is derived.

Generation of Definitive Endoderm and Anterior Foregut Endoderm

The methods for generating human lung progenitor cells as described herein begin by first generating definitive endoderm from embryonic stem cells or induced pluripotent stem cells. "Definitive endoderm" comprises a multipotent cell committed to the endoderm lineage and that can give rise to cells of the gut tube or organs derived from the gut tube. The definitive endoderm is the germ layer that gives rise to gastrointestinal organs (e.g., esophagus, stomach, liver, gall bladder, small intestines, pancreas, colon, etc.), respiratory organs (e.g., alveoli, trachea, bronchi), endocrine glands and organs (e.g., parathyroid gland, thyroid gland, thymus), auditory system (e.g., auditory tube, and tympanic cavity), and the urinary system (e.g., urinary bladder and portions of the urethra). See e.g., Grapin-Botton and Melton, 2000; Kimelman and Griffin, 2000; Tremblay et al., 2000; Wells and Melton, 1999; Wells and Melton, 2000. The term "definitive endoderm" does not encompass the separate lineage of cells termed primitive endoderm, which is responsible for formation of extra-embryonic tissues.

Formation of definitive endoderm and endoderm cells derived therefrom is an important step for the derivation of cells which make up terminally differentiated tissues and/or organs derived from the definitive endoderm lineage, such as the human lung progenitor cells as described herein.

Methods for deriving definitive endoderm from embryonic stem cells or induced pluripotent stem cells are known in the art (e.g., U.S. Pat. Nos. 7,993,916; 7,695,963; 7,541,185; US2009/0298178; US2010/0272695; Sherwood et al., *Mechanisms of Development* (2011) 128:387-400; D'Amour K. et al., *Nature Biotechnology* (2005) 23:1534-1541; Turovets, N. et al., *Differentiation* (2011) 81(5):292-298; Kim, P T. et al., *PLoS One* (2010) 5(11):e14146). In one embodiment, definitive endoderm is produced by contacting an IPSC or ESC with a definitive endoderm medium including e.g., B27, Activin A and ZSTK474. In one embodiment, the definitive endoderm medium comprises 1-5% B27 (e.g., 2%), 10-40 ng/mL Activin A (e.g., 20 ng/mL), and 0.2-0.5 µM ZSTK474 and is useful for generating definitive endoderm in cell lines that have been tested to have low efficiency of definitive endoderm generation or are suspected of having a low efficiency of definitive endoderm generation.

Differentiation of embryonic stem cells or induced pluripotent stem cells to definitive endoderm can be monitored by determining the expression of cell surface markers characteristic of definitive endoderm. In some embodiments, the expression of definitive endoderm markers is determined by detecting the presence or absence of the marker. Alternatively, the expression of certain markers can be determined by measuring the level at which the marker is present in the cells of the cell culture or cell population. Such measurements of marker expression can be either qualitative or quantitative.

In one embodiment, quantitative PCR (Q-PCR) is used to quantify the expression of markers on the definitive endoderm. Methods of performing Q-PCR are well known in the art. In alternative embodiments, expression of a marker gene product is detected using antibodies specific for the cell marker. In certain embodiments, the expression of marker genes characteristic of definitive endoderm as well as the lack of significant expression of marker genes characteristic of the cells from which they are derived (e.g., ES cells or iPSCs) and other cell types is determined.

In one embodiment, a marker of definitive endoderm is the SOX17 gene. Other markers of definitive endoderm include, but are not limited to, MIXL1, GATA4, HNF3b, GSC, FGF17, VWF, CALCR, FOXQ1, CMKOR1 and CRIP1. In some embodiments, the expression of both SOX17 and SOX7 is monitored. In other embodiments, expression of the SOX17 marker gene and the OCT4 marker gene, which is characteristic of ES cells, is monitored. Additionally, because definitive endoderm cells express the SOX17 marker gene at a level higher than that of the AFP, SPARC or Thrombomodulin marker genes, the expression of these genes can also be monitored. Another marker of definitive endoderm is the CXCR4 gene, which encodes a cell surface chemokine receptor whose ligand is the chemoattractant SDF-1. In one embodiment, the efficiency of definitive endoderm production can be determined by costaining for FOXA2/SOX17 or by FACS analysis with cKit/CXCR4 or cKit/EpCAM combination.

Once generation of definitive endoderm has been achieved, the next step is to differentiate the definitive endoderm cells to anterior foregut endoderm cells, which is the region that comprises the cells destined to become lung and thyroid cells. This process is also referred to herein as "anteriorization" of definitive endoderm. As used herein, "foregut endoderm" refers to cells of the anterior portion of the gut tube and encompasses cells of the foregut/midgut junction. It will be recognized by one of skill in the art that ESCs or iPSCs can also be differentiated directly to anterior foregut endoderm cells without requiring an intermediate step of generating definitive endoderm. The differentiation methods described herein for generating lung progenitor cells begin from anterior foregut endoderm cells, and thus the method of making such anterior foregut endoderm cells is not critical and is not limited to the methods for generating anterior foregut endoderm that are described herein; any method that provides anterior foregut endoderm can be used to provide the starting material for preparation of lung progenitor cells, as disclosed herein.

Methods for generating anterior foregut endoderm from definitive endoderm are known in the art (see e.g., WO2010/136583, WO2011/139628; Green, M D et al., *Nature Biotechnology* (2011) 29:267-27; Morrison et al, (2008), *Cell Stem Cell*, 3: 355-356; Goss A M et al., *Developmental Cell* (2009) 17(2):290-298; Livigni A et al., *Current Protocols in Stem Cell Biology* (2009) 10:1G.3.1-1G.3.10).

In one embodiment, the production of anterior foregut endoderm is confirmed by the activation of an anterior foregut endoderm specific marker, such as the marker Hex. Hex is a homeobox-containing transcriptional repressor that is one of the earliest markers of anterior foregut endoderm, and has been shown to suppress posterior characteristics (see e.g., Brickman J M et al., *Development* (2000) 127:2303-2315; Thomas P Q et al., *Development* (1998) 125:85-94; Zamparini A L et al., *Development* (2006) 133:3709-3722). The detection of Hex can be used in combination with other anterior foregut endoderm markers, such as Cxcr4 (Morrison, G M et al., *Cell Stem Cell* (2008) 3:402-412). Other exemplary markers include, but are not limited to, FoxA2 and Sox2, among others. In one embodiment, the definitive endoderm undergoes an anteriorization step comprising treatment with a TGFβ agonist (e.g., Activin).

Signaling Pathways for Differentiation

TGF-β signaling pathway modulation: In some embodiments, one or more TGF-β agonists are used to promote a particular differentiation step of a pluripotent cell (e.g., during generation of anterior foregut endoderm). In such embodiments, an activating agent specific for TGF-β signaling can be a TGF-β polypeptide or an active fragment thereof, a fusion protein comprising a TGF-β polypeptide or an active fragment thereof, an agonist antibody to a TGF-β receptor, or a small molecule agonist of a TGF-β receptor.

In other embodiments, one or more TGF-β antagonists can be used to permit differentiation of a pluripotent cell (e.g., for inducing Nkx2.1 expression, the first step towards commitment to lung lineage). In such embodiments, an antagonist for TGF-β signaling can be a polypeptide inhibitor or a fragment thereof, a dominant negative fusion protein, an antagonist antibody to a TGF-β receptor or a small molecule antagonist of a TGF-β receptor.

The Transforming growth factor beta (TGF-β) signaling pathway is involved in many cellular processes in both the adult organism and the developing embryo including cell growth, cell differentiation, apoptosis, cellular homeostasis and other cellular functions. TGF-β superfamily ligands bind to a type II receptor, which recruits and phosphorylates a type I receptor. The type I receptor then phosphorylates receptor-regulated SMADs (R-SMADs) which then bind the coSMAD SMAD4. R-SMAD/coSMAD complexes accumulate in the nucleus where they act as transcription factors and participate in the regulation of target gene expression.

TGF-β1 is a prototypic member of a family of cytokines including the TGF-βs, activins, inhibins, bone morphogenetic proteins and Mullerian-inhibiting substance. Smad proteins are exemplary downstream signal transduction factors in the TGF-beta pathway and therefore, in some embodiments, can be activated directly to effect differentiation to a human lung cell progenitor phenotype (e.g., by treating a cell with an activator of a Smad protein). Exemplary Smad activators include, but are not limited to, Smad proteins or functional peptides or fragments thereof (e.g., Smad1, Smad5, Smad8), BMP2, BMP4, and Mullerian inhibiting substance (MIS). Activin ligands transduce signals in a manner similar to TGF-β ligands. Activins bind to and activate ALK receptors, which in turn phosphorylate Smad proteins such as Smad2 and Smad3. The consequent formation of a hetero-Smad complex with Smad4 results in the activin-induced regulation of gene transcription.

Some non-limiting examples of small molecule inhibitors of TGF-β receptors include 2-(3-(6-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole, which can be purchased from Calbiochem (San Diego, Calif.). Other small molecule inhibitors include, but are not limited to, SB-431542 (see e.g., Halder et al., 2005; Neoplasia 7(5): 509-521), SM16 (see e.g., Fu, K et al., 2008; Arteriosclerosis, Thrombosis and Vascular Biology 28(4):665), and SB-505124 (see e.g., Dacosta Byfield, S., et al., 2004; Molecular Pharmacology 65:744-52), among others. Additional TGF-β receptor antagonists are known in the art.

In some embodiments, the dosage range useful for a TGF-β antagonist (e.g., A8301) is between 0.1 and 10 µM, for example between 0.1 and 1 µM, between 0.1 and 0.5 µM, between 0.1 and 2 µM, between 0.1 and 3 µM, between 0.1 and 4 µM, between 0.1 and 5 µM, between 0.1 and 6 µM, between 0.1 and 7 µM, between 0.1 and 8 µM, between 0.1 and 9 µM, between 0.5 and 2 µM, between 0.5 and 5 µM, between 1 and 3 µM, between 2 and 4 µM, between 2 and 6 µM, between 2 and 7 µM, between 5 and 10 µM, between 6 and 10 µM, between 7 and 10 µM, between 8 and 10 µM, between 9 and 10 µM. In some embodiments the TGF-β antagonist is used at a dose of e.g., at least 0.1 µM, at least 0.2 µM, at least 0.3 µM, at least 0.4 µM, at least 0.5 µM, at least 0.6 µM, at least 0.7 µM, at least 0.8 µM, at least 0.9 µM, at least 1 µM, at least 1.2 µM, at least 1.3 µM, at least 1.4 µM, at least 1.5 µM, at least 1.6 µM, at least 1.7 µM, at least 1.8 µM, at least 1.9 µM, at least 2 µM, at least 2.5 µM, at least 3 µM, at least 3.5 µM, at least 4 µM, at least 4.5 µM, at least 5 µM, at least 5.5 µM, at least 6 µM, at least 6.5 µM, at least 7 µM, at least 7.5 µM, at least 8 µM, at least 8.5 µM, at least 9 µM, at least 9.5 µM, at least 10 µM or more.

BMP Receptor Signaling Pathway Modulation

BMP2 and BMP4 both signal through the type I receptor (ALK3), while BMP7 binds to a separate type I receptor (ALK2). See e.g., von Bubnoff A et al., Developmental Biology (2001) 239:1-14; Chen D. et al., Growth Factors (2004) 22(4):233-241; Sieber C. et al., Cytokine and Growth Factor Rev. (2009) 20:343-355; and Miyazono K et al., Journal of Biochemistry (2010) 147(1):35-51.

Typically, BMP2 and BMP4 bind to a BMP receptor I/II complex, leading to phosphorylation of Smads 1/5/8, followed by formation of heterotrimeric complexes with Smad4. These complexes translocate to the nucleus and activate expression of target genes (von Bubnoff A et al., Developmental Biology (2001) 239:1-14; Chen D. et al., Growth Factors (2004) 22(4):233-241; Sieber C. et al., Cytokine and Growth Factor Rev. (2009) 20:343-355; and Miyazono K et al., Journal of Biochemistry (2010) 147(1): 35-51). Besides Smad1/5/8-mediated transcription, BMP-induced receptor complexes can activate the mitogen-activated protein kinase (MAPK) pathway via ERK, JNK, or p38 (Kozawa O et al., Journal of Cellular Biochemistry 84:583-589).

BMP receptor pathway activation: In some embodiments, a BMP agonist is used with the methods described herein for differentiation of a human lung progenitor cell. In one embodiment, the BMP receptor is a receptor that signals through the SMAD pathway (e.g., ALK3). In other embodiments, the BMPs used with the methods described herein are BMP2 and/or BMP4.

In one embodiment, one or more BMP agonists are used to promote a particular differentiation step of a pluripotent cell. In such embodiments, an activating agent specific for BMP signaling can be a BMP polypeptide or an active fragment thereof, a fusion protein comprising a BMP polypeptide or an active fragment thereof, an agonist antibody to a BMP receptor, or a small molecule agonist of a BMP receptor.

In some embodiments, the dosage range useful for BMP4 is between 1 and 500 nM, for example between 1 and 400 nM, between 1 and 300 nM, between 1 and 200 nM, between 1 and 100 nM, between 1 and 50 nM, between 1 and 25 nM, between 1 and 10 nM, between 1 and 5 nM, between 1 and 2 nM, between 10 and 300 nM, between 15 and 250 nM, between 20 and 250 nM, between 20 and 200 nM, between 30 and 200 nM, between 40 and 200 nM, between 50 and 200 nM, between 60 and 200 nM, between 70 and 200 nM, between 80 and 200 nM, between 90 and 200 nM, between 100 and 200 nM, between 150 and 200 nM, between 150 nM and 300 nM, between 175 and 300 nM, between 200 nM and 300 nM, between 200 nM and 400 nM, between 200 nM and 500 nM.

In some embodiments the dose of BMP4 is e.g., at least 1 nM, at least 2 nM, at least 5 nM, at least 10 nM, at least 20 nM, at least 30 nM, at least 40 nM, at least 50 nM, at least 60 nM, at least 70 nM, at least 80 nM, at least 90 nM, at least 100 nM, at least 110 nM, at least 120 nM, at least 130 nM, at least 140 nM, at least 150 nM, at least 160 nM, at least 170 nM, at least 180 nM, at least 190 nM, at least 200 nM, at least 225 nM, at least 250 nM, at least 275 nM, at least 300 nM, at least 400 nM, at least 500 nM or more.

In some embodiments, the dosage range useful for BMP7 is between 1 and 200 ng/mL, for example between 1 and 100 ng/mL, between 1 and 50 ng/mL, between 1 and 25 ng/mL, between 1 and 10 ng/mL, between 1 and 5 ng/mL, between 1 and 2 ng/mL, between 10 and 200 ng/mL, between 15 and 200 ng/mL, between 20 and 200 ng/mL, between 30 and 200 ng/mL, between 40 and 200 ng/mL, between 50 and 200 ng/mL, between 60 and 200 ng/mL, between 70 and 200 ng/mL, between 80 and 200 ng/mL, between 90 and 200 ng/mL, between 100 and 200 ng/mL, or between 150 and 200 ng/mL.

In some embodiments the dose of BMP7 is e.g., at least 1 ng/mL, at least 2 ng/mL, at least 5 ng/mL, at least 10 ng/mL, at least 20 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 110 ng/mL, at least 120 ng/mL, at least 130 ng/mL, at least 140 ng/mL, at least 150 ng/mL, at least 160 ng/mL, at least 170 ng/mL, at least 180 ng/mL, at least 190 ng/mL, at least 200 ng/mL, or more.

BMP receptor pathway inhibition: In some embodiments, a BMP antagonist is used with the methods described herein for differentiation of a human foregut endoderm cell to a lung progenitor cell. In one embodiment, the BMP antagonist is dorsomorphin.

In one embodiment, one or more BMP receptor pathway antagonists are used to promote a particular differentiation step of a pluripotent cell. In such embodiments, an inhibitor specific for BMP signaling can be a polypeptide or fragment thereof, an shRNA or siRNA directed against a BMP receptor, an antagonist antibody to a BMP receptor, or a small molecule antagonist of a BMP receptor.

In some embodiments, the dosage range useful for a BMP pathway inhibitor is between 1 and 500 nM, for example between 1 and 400 nM, between 1 and 300 nM, between 1 and 200 nM, between 1 and 100 nM, between 1 and 50 nM, between 1 and 25 nM, between 1 and 10 nM, between 1 and 5 nM, between 1 and 2 nM, between 10 and 300 nM, between 15 and 250 nM, between 20 and 250 nM, between 20 and 200 nM, between 30 and 200 nM, between 40 and 200 nM, between 50 and 200 nM, between 60 and 200 nM, between 70 and 200 nM, between 80 and 200 nM, between 90 and 200 nM, between 100 and 200 nM, between 150 and 200 nM, between 150 nM and 300 nM, between 175 and 300 nM, between 200 nM and 300 nM, between 200 nM and 400 nM, between 200 nM and 500 nM.

In some embodiments the dose of the BMP pathway antagonist is e.g., at least 1 nM, at least 2 nM, at least 5 nM, at least 10 nM, at least 20 nM, at least 30 nM, at least 40 nM, at least 50 nM, at least 60 nM, at least 70 nM, at least 80 nM, at least 90 nM, at least 100 nM, at least 110 nM, at least 120 nM, at least 130 nM, at least 140 nM, at least 150 nM, at least 160 nM, at least 170 nM, at least 180 nM, at least 190 nM, at least 200 nM, at least 225 nM, at least 250 nM, at least 275 nM, at least 300 nM, at least 400 nM, at least 500 nM or more.

MAPKK/ERK inhibitors: Provided herein are methods for differentiating a human lung progenitor cell to a Nkx2.1+, Sox2+ proximal multipotent airway progenitor cell or to an Nkx2.1+, Sox9 distal multipotent progenitor cell, wherein the methods comprise treatment with a MAPKK/ERK inhibitor.

Mitogen activated protein kinase (MAPK) signaling pathways are involved in cellular events such as growth, differentiation and stress responses (J. Biol. Chem. (1993) 268, 14553-14556). Four parallel MAPK pathways have been identified to date: ERK1/ERK2, JNK, p38 and ERK5. These pathways are linear kinase cascades in that MAPKKK phosphorylates and activates MAPKK, and MAPKK phosphorylates and activates MAPK. To date, seven MAPKK homologs (MEK1, MEK2, MKK3, MKK4/SEK, MEK5, MKK6, and MKK7) and four MAPK families (ERK1/2, JNK, p38, and ERK5) have been identified. Activation of these pathways regulates the activity of a number of substrates through phosphorylation. These substrates include: transcription factors such as TCF, c-myc, ATF2 and the AP-1 components, fos and Jun; cell surface components EGF-R; cytosolic components including PHAS-T, $p90^{rsk}$, $cPLA_2$ and c-Raf-1; and cytoskeleton components such as tau and MAP2. MAPK signaling cascades are involved in controlling cellular processes including proliferation, differentiation, apoptosis, and stress responses.

MEK occupies a strategic downstream position in the Mek/Erk pathway catalyzing the phosphorylation of its MAPK substrates, ERK1 and ERK2. Anderson et al. *Nature* 1990, v. 343, pp. 651-653. In the ERK pathway, MAPKK corresponds with MEK (MAP kinase ERK Kinase) and the MAPK corresponds with ERK (Extracellular Regulated Kinase).

Some non-limiting examples of MAPK and/or ERK pathway inhibitors include SL327, U0126, SP600125, PD98059, SB203580, and CAY10561. Additional MAPK and/or ERK pathway inhibitors that can be used with the methods described herein are known to those of skill in the art.

In some embodiments, the dosage range useful for a MAPKK/ERK antagonist (e.g., PD98059) is between 0.1 and 5 µM, for example, between 0.1 and 4 µM, between 0.1 and 3 µM, between 0.1 and 2 µM, between 0.1 and 1 µM, between 0.1 and 0.5 µM, between 0.5 and 3 µM, between 0.5 and 2 µM, between 0.5 and 1 µM, between 1 and 2 µM, between 1.5 and 2 µM, between 1 and 1.5 µM, between 2 and 5 µM, between 3 and 5 µM, between 4 and 5 µM.

In some embodiments, the dose of a MAPKK/ERK antagonist is e.g., at least 0.1 µM, at least 0.5 µM, at least 1 µM, at least 1.1 µM, at least 1.2 µM, at least 1.3 µM, at least 1.4 µM, at least 1.5 µM, at least 1.6 µM, at least 1.7 µM, at least 1.8 µM, at least 1.9 µM, at least 2 µM, at least 2.5 µM, at least 3 µM, at least 4 µM, at least 5 µM or more.

FGF activation: Fibroblast growth factors, or FGFs, are a family of growth factors that play a role in angiogenesis, wound healing, and embryonic development. FGFs and functional fragments or analogs thereof are useful for differentiating human lung progenitor cells to e.g., proximal multipotent airway progenitor cells, distal multipotent lung progenitor cells, and multipotent airway basal stem cells, as described herein.

FGFs are heparin-binding proteins, which interact with cell-surface-associated heparan sulfate proteoglycans to effect FGF signaling. At least 22 different members of the FGF family have been identified. FGF1, FGF2, FGF3, FGF4, FGF5, FGF6, FGF7, FGF8, FGF9, and FGF10 bind and effect signaling through fibroblast growth receptors (FGFR).

FGFs induce mitosis in a variety of cell types and also have regulatory, morphological, and endocrine effects. FGFs function throughout embryonic development and aid in mesoderm induction, antero-posterior patterning, limb development, neural induction and neural development. In one embodiment, a preferred FGF for use with the methods described herein is FGF7, which is also known in the art as Keratinocyte Growth Factor (KGF).

In some embodiments, the dosage range useful for FGF7 or FGF2 is between 10 and 200 ng/mL, for example between 10 and 100 ng/mL, between 10 and 50 ng/mL, between 15 and 200 ng/mL, between 20 and 200 ng/mL, between 30 and 200 ng/mL, between 40 and 200 ng/mL, between 50 and 200 ng/mL, between 60 and 200 ng/mL, between 70 and 200 ng/mL, between 80 and 200 ng/mL, between 90 and 200 ng/mL, between 100 and 200 ng/mL, or between 150 and 200 ng/mL.

In some embodiments the dose of FGF7 or FGF2 is e.g., at least 10 ng/mL, at least 20 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 110 ng/mL, at least 120 ng/mL, at least 130 ng/mL, at least 140 ng/mL, at least 150 ng/mL, at least 160 ng/mL, at least 170 ng/mL, at least 180 ng/mL, at least 190 ng/mL, at least 200 ng/mL, at least 225 ng/mL, at least 250 ng/mL or more.

Wnt pathway modulation: Without wishing to be bound by theory, Wnt proteins and their cognate receptors signal through at least two distinct intracellular pathways. The "canonical" Wnt signaling pathway, (referred to herein as the Wnt/β-catenin pathway) involves Wnt signaling via β-catenin to activate transcription through TCF-related proteins (van de Wetering et al. (2002) Cell 109 Suppl: S13-9; Moon et al. (2002) Science 296(5573): 1644-6). A non-canonical alternative pathway exists, in which Wnt activates protein kinase C (PKC), calcium/calmodulin-dependent kinase II (CaMKII), JNK and Rho-GTPases (Veeman et al. (2003) Dev Cell 5(3): 367-77), and is often involved in the control of cell polarity.

Wnt Antagonists: Provided herein are methods for differentiating human lung progenitor cells to a more differentiated stem cell phenotype, e.g., to an Nkx2.1+, Sox2+ proximal multipotent airway progenitor cell or to an Nkx2.1+, Sox9+ distal multipotent lung progenitor cell, or to an Nkx2.1+, p63+ multipotent airway basal stem cell by contacting a cell with a Wnt antagonist.

As used herein, the term "Wnt antagonist" or "Wnt inhibitor" refers to any agent that inhibits the Wnt/β-catenin pathway, or enhances the activity and/or expression of inhibitors of Wnt/β-catenin signaling, for example activators or enhancers of GSK-3β activity. A Wnt inhibitory agent as used herein can suppress the Wnt/β-catenin pathway at any point along the pathway, for example, but not limited to decreasing the expression and/or activity of Wnt, or β-catenin or Wnt dependent genes and/or proteins, and increasing the expression and/or activity of endogenous inhibitors of Wnt and/or β-catenin or increasing the expression and/or activity of endogenous inhibitors of components of the Wnt/β-catenin pathway, for example increasing the expression of GSK-3β.

Some non-limiting examples of Wnt antagonists include Wnt pathway inhibitor V (also known as (E)-4-(2,6-Difluorostyryl)-N,N-dimethylaniline), IWR-1 endo, IWP-2, CCT036477, and a peptide comprising the sequence t-Boc-NH-Met-Asp-Gly-Cys-Glu-Leu-CO2H (SEQ ID NO: 1).

In some embodiments, the dosage range useful for a Wnt antagonist (e.g. IWR-1) is between 20 and 200 ng/mL, between 30 and 200 ng/mL, between 40 and 200 ng/mL, between 50 and 200 ng/mL, between 60 and 200 ng/mL, between 70 and 200 ng/mL, between 80 and 200 ng/mL, between 90 and 200 ng/mL, between 100 and 200 ng/mL, or between 150 and 200 ng/mL.

In some embodiments the dose of a Wnt antagonist is e.g., at least 20 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 110 ng/mL, at least 120 ng/mL, at least 130 ng/mL, at least 140 ng/mL, at least 150 ng/mL, at least 160 ng/mL, at least 170 ng/mL, at least 180 ng/mL, at least 190 ng/mL, at least 200 ng/mL, or more.

Wnt agonists: Provided herein are methods for differentiating a human foregut endoderm cell to a more differentiated cell type, e.g., to an Nkx2.1+, Tuj negative, Pax8 negative lung progenitor cell by contacting a cell with a Wnt agonist.

As used herein, the term "Wnt agonist" refers to any agent that activates the Wnt/β-catenin pathway, or inhibits the activity and/or expression of inhibitors of Wnt/β-catenin signaling, for example antagonists or inhibitors of GSK-3β activity. A Wnt activating agent as used herein can enhance signaling through the Wnt/β-catenin pathway at any point along the pathway, for example, but not limited to increasing the expression and/or activity of Wnt, or β-catenin or Wnt dependent genes and/or proteins, and decreasing the expression and/or activity of endogenous inhibitors of Wnt and/or β-catenin or decreasing the expression and/or activity of endogenous inhibitors of components of the Wnt/β-catenin pathway, for example decreasing the expression of GSK-3β.

Some non-limiting examples of Wnt pathway agonists include CHIR9902, 2-amino-4-[3,4-(methylenedioxy)benzyl-amino]-6-(3-methoxyphenyl)pyrimidine, BIO, (2'Z, 3'E)-6-Bromoindirubin-3'-oxime, 5-(Furan-2-yl)-N-(3-(1H-imidazol-1-yl)propyl)-1,2-oxazole-3-carboxamide, and SKL2001.

In some embodiments, the dosage range useful for a Wnt agonist (e.g. CHIR9902) is between 20 and 200 ng/mL, between 30 and 200 ng/mL, between 40 and 200 ng/mL, between 50 and 200 ng/mL, between 60 and 200 ng/mL, between 70 and 200 ng/mL, between 80 and 200 ng/mL, between 90 and 200 ng/mL, between 100 and 200 ng/mL, or between 150 and 200 ng/mL.

In some embodiments the dose of a Wnt agonist is e.g., at least 20 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 110 ng/mL, at least 120 ng/mL, at least 130 ng/mL, at least 140 ng/mL, at least 150 ng/mL, at least 160 ng/mL, at least 170 ng/mL, at least 180 ng/mL, at least 190 ng/mL, at least 200 ng/mL, or more.

In some embodiments, the dosage range useful for a Wnt agonist (e.g., CHIR9902) is between 0.1 and 5 μM, for example, between 0.1 and 4 μM, between 0.1 and 3 μM, between 0.1 and 2 μM, between 0.1 and 1 μM, between 0.1 and 0.5 μM, between 0.5 and 3 μM, between 0.5 and 2 μM, between 0.5 and 1 μM, between 1 and 2 μM, between 1.5 and 2 μM, between 1 and 1.5 μM, between 2 and 5 μM, between 3 and 5 μM, between 4 and 5 μM.

In some embodiments, the dose of a Wnt agonist (e.g., CHIR9902) is e.g., at least 0.1 μM, at least 0.5 μM, at least 1 μM, at least 1.1 μM, at least 1.2 μM, at least 1.3 μM, at least 1.4 μM, at least 1.5 μM, at least 1.6 μM, at least 1.7 μM, at least 1.8 μM, at least 1.9 μM, at least 2 μM, at least 2.5 μM, at least 3 μM, at least 4 μM, at least 5 μM or more.

PI3 Kinase Inhibitors:

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

As used herein, the term "PI3 kinase inhibitor" or "PI3 kinase antagonist" refers to any agent that inhibits the activity of PI3 kinase. Some non-limiting examples of a PI3 kinase inhibitor useful with the methods described herein include LY294002, wortmannin, PIK-75, ZSTK474, and Pp242.

In some embodiments, the dosage range useful for a PI3 kinase inhibitor (e.g., ZSTK474, or PIK-75) is between 0.1 and 5 µM, for example, between 0.1 and 4 µM, between 0.1 and 3 µM, between 0.1 and 2 µM, between 0.1 and 1 µM, between 0.1 and 0.5 µM, between 0.5 and 3 µM, between 0.5 and 2 µM, between 0.5 and 1 µM, between 1 and 2 µM, between 1.5 and 2 µM, between 1 and 1.5 µM, between 2 and 5 µM, between 3 and 5 µM, between 4 and 5 µM.

In some embodiments, the dose of a PI3 kinase inhibitor (e.g., ZSTK474, or PIK-75) is e.g., at least 0.1 µM, at least 0.5 µM, at least 1 µM, at least 1.1 µM, at least 1.2 µM, at least 1.3 µM, at least 1.4 µM, at least 1.5 µM, at least 1.6 µM, at least 1.7 µM, at least 1.8 µM, at least 1.9 µM, at least 2 µM, at least 2.5 µM, at least 3 µM, at least 4 µM, at least 5 µM or more.

Monitoring Differentiation of Human Lung Progenitors

Provided herein are methods for differentiating or redifferentiating a pluripotent stem cell (e.g., an anterior foregut endoderm cell, a definitive endoderm cell, an ES cell or an iPSC) to a human lung progenitor cell, and optionally further differentiating such human lung progenitor cells to lung airway cells, such as basal cells, Clara cells, ciliated cells and/or goblet cells. These aspects are based on the novel discovery of a method for differentiation of pluripotent stem cells to a stem cell or progenitor cell committed to the lung and/or airway lineage. Such methods are exemplified in the Examples section herein. Also provided herein are compositions of human lung progenitor cells having particular characteristics, such as the presence of one or more cell surface or other markers that are lung cell specific. Alternatively, or in addition, the human lung progenitor cell compositions described herein lack markers of embryonic stem cells or induced pluripotent stem cells. In one embodiment of the methods described herein, one or more cell surface markers are used to determine the degree of differentiation along the spectrum of embryonic stem cells or iPSCs to fully differentiated lung cells.

Cell surface markers, particularly stem cell surface markers, are useful with the methods and compositions described herein to identify the differentiation or dedifferentiation state of a cell. For example, during reprogramming of a somatic cell to an induced pluripotent stem cell the activation of stem cell markers can be used to confirm that the somatic cell has been dedifferentiated (either partially or completely). Alternatively, during differentiation of an ES cell or an iPSC to a human lung progenitor cell, the activation of lung-specific markers can be used to confirm the degree of differentiation that the stem cell has undergone. In addition, the activation or deactivation of particular lung-specific markers can be used to determine the degree of multipotency of a human lung progenitor cell. This can be achieved by comparing the lung-specific markers present on, or expressed by the cell with the marker profile of lung cells during development and inferring the degree of multipotency of the differentiated cell based on the known degree of multipotency of the corresponding lung cell during embryonic development.

Marker-specific agents can be used to recognize stem cell markers, for instance labeled antibodies that recognize and bind to cell-surface markers or antigens on desired stem cells. Antibodies or similar agents specific for a given marker, or set of markers, can be used to separate and isolate the desired stem cells using fluorescent activated cell sorting (FACS), panning methods, magnetic particle selection, particle sorter selection and other methods known to persons skilled in the art, including density separation (Xu et al. (2002) Circ. Res. 91:501; U.S.S.N. 20030022367) and separation based on other physical properties (Doevendans et al. (2000) J. Mol. Cell. Cardiol. 32:839-851).

Alternatively, genetic selection methods can be used, where a progenitor or stem cell can be genetically engineered to express a reporter protein operatively linked to a tissue-specific promoter and/or a specific gene promoter; therefore the expression of the reporter can be used for positive selection methods to isolate and enrich the desired stem cell. For example, a fluorescent reporter protein can be expressed in the desired stem cell by genetic engineering methods to operatively link the marker protein to a promoter active in a desired stem cell (Klug et al. (1996) J. Clin. Invest. 98:216-224; U.S. Pat. No. 6,737,054). In some embodiments, cells from which the human lung progenitor cells are derived are not modified using genetic means. Other approaches for positive selection include drug selection, for instance as described by Klug et al., supra, involving enrichment of desired cells by density gradient centrifugation. Negative selection can be performed, selecting and removing cells with undesired markers or characteristics, for example fibroblast markers, epithelial cell markers etc.

Undifferentiated ES cells express genes that can be used as markers to detect the presence of undifferentiated cells. The polypeptide products of such genes can be used as markers for negative selection. For example, see U.S.S.N. 2003/0224411 A1; Bhattacharya (2004) Blood 103(8):2956-64; and Thomson (1998), supra., each herein incorporated by reference. Human ES cell lines express cell surface markers that characterize undifferentiated nonhuman primate ES and human EC cells, including, but not limited to, stage-specific embryonic antigen (SSEA)-3, SSEA-4, TRA-1-60, TRA-1-81, and alkaline phosphatase. The globo-series glycolipid GL7, which carries the SSEA-4 epitope, is formed by the addition of sialic acid to the globo-series glycolipid Gb5, which carries the SSEA-3 epitope. Thus, GL7 reacts with antibodies to both SSEA-3 and SSEA-4. Undifferentiated human ES cell lines do not stain for SSEA-1, but differentiated cells stain strongly for SSEA-1. Methods for proliferating hES cells in the undifferentiated form are described in WO 99/20741, WO 01/51616, and WO 03/020920, the contents of which are herein incorporated by reference in their entireties.

Exemplary cell surface markers expressed on lung progenitor cells include, but are not limited to, Sox2, Sox9, p63, FoxP2, ETV4/5, FoxA2, Nkx2.1, Gata6, ID2, CK5, NGFR, FoxJ1, CCSP, Scgb3a2, Muc5ac, T1a, Spc, and Scgn. Particular cell compositions with combinations of such cell surface markers are exemplified herein in the Examples section.

In some embodiments, the human lung progenitor cells are an enriched population of cells; that is, the percentage of human lung progenitor cells (e.g., percent of cells) in a population of cells is at least 10% of the total number of cells in the population. For example, an enriched population comprises at least 15% human lung progenitor cells, at least 20%, at least 30%, at least 40%, at least 50%, at least 60%, at least 70%, at least 80%, at least 90%, at least 95%, at least 99% or even 100% of the population comprises human lung progenitor cells. In some embodiments, a population of cells comprises at least 100 cells, at least 500 cells, at least 1000 cells, at least $1\times10^4$ cells, at least $1\times10^5$ cells, at least $1\times10^6$ cells, at least $1\times10^7$ cells, at least $1\times10^8$ cells, at least $1\times10^9$ cells, at least $1\times10^{10}$ cells, at least $1\times10^{11}$ cells, at least $1\times10^{12}$ cells, at least $1\times10^{13}$ cells, at least $1\times10^{14}$ cells, at least $1\times10^{15}$ cells, or more.

In one embodiment, the human lung progenitor cells described herein are not tumor cells or cancer cells. In such embodiments, the human lung progenitor cell can be distinguished from a tumor cell or cancer cell using e.g., a cell marker profile.

Scaffold Compositions

Biocompatible synthetic, natural, as well as semi-synthetic polymers, can be used for synthesizing polymeric particles that can be used as a scaffold material. In general, for the practice of the methods described herein, it is preferable that a scaffold biodegrades such that the lung progenitor cells can be isolated from the polymer prior to implantation or such that the scaffold degrades over time in a subject and does not require removal. Thus, in one embodiment, the scaffold provides a temporary structure for growth and/or delivery of human lung progenitor cells to a subject in need thereof. In some embodiments, the scaffold permits human cell progenitors to be grown in a shape suitable for transplantation or administration into a subject in need thereof, thereby permitting removal of the scaffold prior to implantation and reducing the risk of rejection or allergic response initiated by the scaffold itself.

Examples of polymers which can be used include natural and synthetic polymers, although synthetic polymers are preferred for reproducibility and controlled release kinetics. Synthetic polymers that can be used include biodegradable polymers such as poly(lactide) (PLA), poly(glycolic acid) (PGA), poly(lactide-co-glycolide) (PLGA), and other polyhydroxyacids, poly(caprolactone), polycarbonates, polyamides, polyanhydrides, polyphosphazene, polyamino acids, polyortho esters, polyacetals, polycyanoacrylates and biodegradable polyurethanes; non-biodegradable polymers such as polyacrylates, ethylene-vinyl acetate polymers and other acyl-substituted cellulose acetates and derivatives thereof; polyurethanes, polystyrenes, polyvinyl chloride, polyvinyl fluoride, poly(vinyl imidazole), chlorosulphonated polyolefins, and polyethylene oxide. Examples of biodegradable natural polymers include proteins such as albumin, collagen, fibrin, silk, synthetic polyamino acids and prolamines; polysaccharides such as alginate, heparin; and other naturally occurring biodegradable polymers of sugar units. Alternately, combinations of the aforementioned polymers can be used.

PLA, PGA and PLA/PGA copolymers are particularly useful for forming biodegradable scaffolds. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136; 3,531,561 to Trehu.

PGA is a homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture", Chemistry and Industry, 905 (1970).

Fibers can be formed by melt-spinning, extrusion, casting, or other techniques well known in the polymer processing area. Preferred solvents, if used to remove a scaffold prior to implantation, are those which are completely removed by the processing or which are biocompatible in the amounts remaining after processing.

Polymers for use in the matrix should meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy.

Scaffolds can be of any desired shape and can comprise a wide range of geometries that are useful for the methods described herein. A non-limiting list of shapes includes, for example, hollow particles, tubes, sheets, cylinders, spheres, and fibers, among others. The shape or size of the scaffold should not substantially impede cell growth, cell differentiation, cell proliferation or any other cellular process, nor should the scaffold induce cell death via e.g., apoptosis or necrosis. In addition, care should be taken to ensure that the scaffold shape permits appropriate surface area for delivery of nutrients from the surrounding medium to cells in the population, such that cell viability is not impaired. The scaffold porosity can also be varied as desired by one of skill in the art.

In some embodiments, attachment of the cells to a polymer is enhanced by coating the polymers with compounds such as basement membrane components, agar, agarose, gelatin, gum arabic, collagens types I, II, III, IV, and V, fibronectin, laminin, glycosaminoglycans, polyvinyl alcohol, mixtures thereof, and other hydrophilic and peptide attachment materials known to those skilled in the art of cell culture or tissue engineering. Examples of a material for coating a polymeric scaffold include polyvinyl alcohol and collagen.

In some embodiments, the scaffold can include decellularized lung tissue. Methods for producing decellularized lung tissue are known in the art, see e.g., WO2011/005306. Briefly, the process of decellularization involves chemically stripping lung tissue of its cells and removing the cellular debris, which leaves behind the structure of the extracellular matrix. The extracellular matrix can then be repopulated with human lung progenitor cells as described herein, and optionally with other bioactive agents. Such decellularized scaffolds can be prepared from a portion of the subject's own lung and therefore the risk of rejection or allergic reaction in response to the repopulated and administered scaffold can be minimized.

In some embodiments it can be desirable to add bioactive molecules to the scaffold. A variety of bioactive molecules can be delivered using the matrices described herein. These are referred to generically herein as "factors" or "bioactive factors".

In one embodiment, the bioactive factors include growth factors. Examples of growth factors include platelet derived growth factor (PDGF), transforming growth factor alpha or beta (TGFβ), bone morphogenic protein 4 (BMP4), fibroblastic growth factor 7 (FGF7), fibroblast growth factor 10 (FGF10), epidermal growth factor (EGF/TGFα), vascular endothelium growth factor (VEGF), some of which are also angiogenic factors.

These factors are known to those skilled in the art and are available commercially or described in the literature. Bioactive molecules can be incorporated into the matrix and released over time by diffusion and/or degradation of the matrix, or they can be suspended with the cell suspension.

Treatment of Lung Disease/Disorders and Lung Injury

The methods and compositions provided herein relate to the generation and use of human lung progenitor cells. Accordingly, provided herein are methods for the treatment and prevention of a lung injury or a lung disease or disorder in a subject in need thereof. The methods described herein can be used to treat, ameliorate, prevent or slow the progression of a number of lung diseases or their symptoms, such as those resulting in pathological damage to lung or airway architecture and/or alveolar damage. The terms "respiratory disorder," "respiratory disease," "lung disease," "lung disorder," "pulmonary disease," and "pulmonary disorder," are used interchangeably herein and refer to any condition and/or disorder relating to respiration and/or the respiratory system, including the lungs, pleural cavity, bronchial tubes, trachea, upper respiratory tract, airways, or other components or structures of the airway system.

Such lung diseases include, but are not limited to, bronchopulmonary dysplasia (BPD), chronic obstructive pulmonary disease (COPD), cystic fibrosis, bronchiectasis, cor pulmonale, pneumonia, lung abcess, acute bronchitis, chronic bronchitis, emphysema, pneumonitis (e.g., hypersensitivity pneumonitis or pneumonitis associated with radiation exposure), alveolar lung diseases and interstitial lung diseases, environmental lung disease (e.g., associated with asbestos, fumes or gas exposure), aspiration pneumonia, pulmonary hemorrhage syndromes, amyloidosis, connective tissue diseases, systemic sclerosis, ankylosing spondylitis, pulmonary actinomycosis, pulmonary alveolar proteinosis, pulmonary anthrax, pulmonary edema, pulmonary embolus, pulmonary inflammation, pulmonary histiocytosis X, pulmonary hypertension, surfactant deficiencies, pulmonary hypoplasia, pulmonary neoplasia, pulmonary nocardiosis, pulmonary tuberculosis, pulmonary veno-occlusive disease, rheumatoid lung disease, sarcoidosis, postpneumonectomy, Wegener's granulomatosis, allergic granulomatosis, granulomatous vasculitides, eosinophilia, asthma and airway hyperreactivity (AHR) (e.g., mild intermittent asthma, mild persistent asthma, moderate persistent asthma, severe persistent asthma, acute asthma, chronic asthma, atopic asthma, allergic asthma or idiosyncratic asthma), allergic bronchopulmonary aspergillosis, chronic sinusitis, pancreatic insufficiency, lung or vascular inflammation, bacterial or viral infection, e.g., *Haemophilus influenzae, S. aureus, Pseudomonas aeruginosa* or respiratory syncytial virus (RSV) infection or an acute or chronic adult or pediatric respiratory distress syndrome (RDS) such as grade I, II, III or IV RDS or an RDS associated with, e.g., sepsis, pneumonia, reperfusion, atelectasis or chest trauma.

Chronic obstructive pulmonary diseases (COPDs) include those conditions where airflow obstruction is located at upper airways, intermediate-sized airways, bronchioles or parenchyma, which can be manifested as, or associated with, tracheal stenosis, tracheal right ventricular hypertrophy pulmonary hypertension, polychondritis, bronchiectasis, bronchiolitis, e.g., idiopathic bronchiolitis, ciliary dyskinesia, asthma, emphysema, connective tissue disease, bronchiolitis of chronic bronchitis or lung transplantation.

The methods described herein can also be used to treat or ameliorate acute or chronic lung diseases/disorders or their symptoms or complications, including airway epithelium injury, airway smooth muscle spasm or airway hyperresponsiveness, airway mucosa edema, increased mucus secretion, excessive T cell activation, or desquamation, atelectasis, cor pulmonale, pneumothorax, subcutaneous emphysema, dyspnea, coughing, wheezing, shortness of breath, tachypnea, fatigue, decreased forced expiratory volume in the 1st second ($FEV_1$), arterial hypoxemia, respiratory acidosis, inflammation including unwanted elevated levels of mediators such as IL-4, IL-5, IgE, histamine, substance P, neurokinin A, calcitonin gene-related peptide or arachidonic acid metabolites such as thromboxane or leukotrienes ($LTD_4$ or $LTC_4$), and cellular airway wall infiltration, e.g., by eosinophils, lymphocytes, macrophages or granulocytes.

Any of these and other respiratory or pulmonary conditions or symptoms are known in the art. See e.g., The Merck Manual, 17th edition, M. H. Beers and R. Berkow editors, 1999, Merck Research Laboratories, Whitehouse Station, N.J., ISBN 0911910-10-7, or in other references cited herein.

As used herein, the terms "administering," "introducing" and "transplanting" are used interchangeably in the context of the placement of cells, e.g. lung progenitor cells, as described herein into a subject, by a method or route which results in at least partial localization of the introduced cells at a desired site, such as a site of injury or repair, such that a desired effect(s) is produced. The cells e.g. lung progenitor cells, or their differentiated progeny (e.g. airway progenitor cells, basal cells, Clara cells, ciliated cells or goblet cells) can be implanted directly to the respiratory airways, or alternatively be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years, i.e., long-term engraftment. For example, in some embodiments of the aspects described herein, an effective amount of lung progenitor cells is administered directly to the lungs of an infant suffering from bronchopulmonary dysplasia by intratracheal administration. In other embodiments, lung progenitor cells can be administered via an indirect systemic route of administration, such as an intraperitoneal or intravenous route.

When provided prophylactically, lung progenitor cells described herein can be administered to a subject in advance of any symptom of a lung disorder, e.g., an asthma attack or to a premature infant. Accordingly, the prophylactic administration of a lung progenitor cell population serves to prevent a lung disorder, as disclosed herein.

When provided therapeutically, lung progenitor cells are provided at (or after) the onset of a symptom or indication of a lung disorder, e.g., upon the onset of COPD.

In some embodiments of the aspects described herein, the lung progenitor cell population being administered according to the methods described herein comprises allogeneic lung progenitor cells obtained from one or more donors. As used herein, "allogeneic" refers to a lung progenitor cell or biological samples comprising lung progenitor cells obtained from one or more different donors of the same species, where the genes at one or more loci are not identical. For example, a lung progenitor cell population being administered to a subject can be derived from umbilical cord blood obtained from one more unrelated donor subjects, or from one or more non-identical siblings. In some embodiments, syngeneic lung progenitor cell populations can be used, such as those obtained from genetically identical animals, or from identical twins. In other embodiments of this aspect, the lung progenitor cells are autologous cells; that is, the lung progenitor cells are obtained or isolated from a subject and administered to the same subject, i.e., the donor and recipient are the same.

Depending on the disease/disorder or injury to be treated, as well as the location of the lung injury, either an undifferentiated human lung progenitor cell, or a differentiated cell thereof can be administered to the subject.

Pharmaceutically Acceptable Carriers

The methods of administering human lung progenitors to a subject as described herein involve the use of therapeutic compositions comprising lung progenitor cells. Therapeutic compositions contain a physiologically tolerable carrier together with the cell composition and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset, transplant rejection, allergic reaction, and the like. A pharmaceutically acceptable carrier will not promote the raising of an immune response to an agent with which it is admixed, unless so desired. The preparation of a composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared.

In general, the human lung progenitor cells described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the human lung progenitor cells as described herein using routine experimentation.

A cell composition can also be emulsified or presented as a liposome composition, provided that the emulsification procedure does not adversely affect cell viability. The cells and any other active ingredient can be mixed with excipients which are pharmaceutically acceptable and compatible with the active ingredient and in amounts suitable for use in the therapeutic methods described herein.

Additional agents included in a cell composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

Administration and Efficacy

Provided herein are methods for treating a lung disease, a lung disorder, or a lung injury comprising administering human lung progenitor cells or differentiated progeny thereof to a subject in need thereof.

Measured or measurable parameters include clinically detectable markers of disease, for example, elevated or depressed levels of a clinical or biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated.

The term "effective amount" as used herein refers to the amount of a population of human lung progenitor cells or their progeny needed to alleviate at least one or more symptom of the lung injury or the lung disease or disorder, and relates to a sufficient amount of a composition to provide the desired effect, e.g., treat a subject having smoking induced-injury or cystic fibrosis. The term "therapeutically effective amount" therefore refers to an amount of human lung progenitor cells or a composition comprising human lung progenitor cells that is sufficient to promote a particular effect when administered to a typical subject, such as one who has or is at risk for a lung disease or disorder. An effective amount as used herein would also include an amount sufficient to prevent or delay the development of a symptom of the disease, alter the course of a symptom disease (for example but not limited to, slow the progression of a symptom of the disease), or reverse a symptom of the disease. It is understood that for any given case, an appropriate "effective amount" can be determined by one of ordinary skill in the art using routine experimentation.

In some embodiments, the subject is first diagnosed as having a disease or disorder affecting the lung tissue prior to administering the cells according to the methods described herein. In some embodiments, the subject is first diagnosed as being at risk of developing lung disease or disorder prior to administering the cells. For example, a premature infant can be at a significant risk of developing a lung disease or disorder.

For use in the various aspects described herein, an effective amount of human lung progenitor cells, comprises at least $10^2$ lung progenitor cells, at least $5 \times 10^2$ lung progenitor cells, at least $10^3$ lung progenitor cells, at least $5 \times 10^3$ lung progenitor cells, at least $10^4$ lung progenitor cells, at least $5 \times 10^4$ lung progenitor cells, at least $10^5$ lung progenitor cells, at least $2 \times 10^5$ lung progenitor cells, at least $3 \times 10^5$ lung progenitor cells, at least $4 \times 10^5$ lung progenitor cells, at least $5 \times 10^5$ lung progenitor cells, at least $6 \times 10^5$ lung progenitor cells, at least $7 \times 10^5$ lung progenitor cells, at least $8 \times 10^5$ lung progenitor cells, at least $9 \times 10^5$ lung progenitor cells, at least $1 \times 10^6$ lung progenitor cells, at least $2 \times 10^6$ lung progenitor cells, at least $3 \times 10^6$ lung progenitor cells, at least $4 \times 10^6$ lung progenitor cells, at least $5 \times 10^6$ lung progenitor cells, at least $6 \times 10^6$ lung progenitor cells, at least $7 \times 10^6$ lung progenitor cells, at least $8 \times 10^6$ lung progenitor cells, at least $9 \times 10^6$ lung progenitor cells, or multiples thereof. The lung progenitor cells can be derived from one or more donors, or can be obtained from an autologous source. In some embodiments of the aspects described herein, the lung progenitor cells are expanded in culture prior to administration to a subject in need thereof.

Exemplary modes of administration for use in the methods described herein include, but are not limited to, injection, intrapulmonary (including intranasal and intratracheal) infusion, inhalation as an aerosol (including intranasal), and implantation (with or without a scaffold material). "Injection" includes, without limitation, intravenous, intramuscular, intraarterial, intradermal, intraperitoneal, transtracheal and subcutaneous. The phrases "parenteral administration" and "administered parenterally" as used herein, refer to modes of administration other than enteral and topical administration, usually by injection, and includes, without limitation, intravenous, intraperitoneal, intramuscular, intraarterial, intradermal, transtracheal, and subcutaneous administration.

In some embodiments, a therapeutically effective amount of lung progenitor cells is administered using intrapulmonary administration, such as an intranasal or intratracheal route. In some aspects of these methods, a therapeutically effective amount of lung progenitor cells are administered using a systemic, such as an intraperitoneal or intravenous route. In other aspects of these methods, a therapeutically effective amount of lung progenitor cells is administered using both intrapulmonary and intraperitoneal administration. These methods are particularly aimed at therapeutic and prophylactic treatments of human subjects having, or at risk of having, a lung disease or disorder. The human lung progenitor cells described herein can be administered to a subject having any lung disease or disorder by any appropriate route which results in an effective treatment in the subject. In some embodiments of the aspects described herein, a subject having a lung disorder is first selected prior to administration of the cells.

In some embodiments, an effective amount of lung progenitor cells are administered to a subject by intrapulmonary administration or delivery. As defined herein, "intrapulmonary" administration or delivery refers to all routes of administration whereby a population of lung progenitor cells, such as Nkx2.1+, Sox2+ lung progenitor cells, is administered in a way that results in direct contact of these cells with the airways of a subject, including, but not limited to, transtracheal, intratracheal, and intranasal administration.

In some such embodiments, the cells are injected into the nasal passages or trachea. In some embodiments, the cells are directly inhaled by a subject. In some embodiments, intrapulmonary delivery of cells includes administration methods whereby cells are administered, for example as a cell suspension, to an intubated subject via a tube placed in the trachea or "tracheal intubation."

As used herein, "tracheal intubation" refers to the placement of a flexible tube, such as a plastic tube, into the trachea. The most common tracheal intubation, termed herein as "orotracheal intubation" is where, with the assistance of a laryngoscope, an endotracheal tube is passed through the mouth, larynx, and vocal cords, into the trachea. A bulb is then inflated near the distal tip of the tube to help secure it in place and protect the airway from blood, vomit, and secretions. In some embodiments, cells are administered to a subject having "nasotracheal intubation," which is defined as a tracheal intubation where a tube is passed through the nose, larynx, vocal cords, and trachea.

In some embodiments, an effective amount of lung progenitor cells is administered to a subject by systemic administration, such as intravenous administration.

The phrases "systemic administration," "administered systemically", "peripheral administration" and "administered peripherally" as used herein refer to the administration of a population of lung progenitor cells other than directly into a target site, tissue, or organ, such as the lung, such that it enters, instead, the subject's circulatory system and, thus, is subject to metabolism and other like processes.

In some embodiments of the aspects described herein, one or more routes of administration are used in a subject to achieve distinct effects. For example, lung progenitor cells can be administered to a subject by both intratracheal and intraperitoneal administration routes for treating or repairing lung epithelium and for pulmonary vascular repair and regeneration respectively. In such embodiments, different effective amounts of the isolated or enriched lung progenitor cells can be used for each administration route.

Where aerosol administration is to be used, nebulizer devices require formulations suitable for dispensing the particular composition. The choice of formulation will depend upon the specific composition used and the number of lung progenitors to be administered; such formulations can be adjusted by the skilled practitioner. However, as an example, where the composition is lung progenitor cells in a pharmaceutically acceptable carrier, the composition can be a suspension of the cells in an appropriate buffer (e.g., saline buffer) at an effective concentration of cells per mL of solution. The formulation can also include cell nutrients, a simple sugar (e.g., for osmotic pressure regulation) or other components to maintain the viability of the cells.

Typically, each formulation for aerosol delivery via a nebulizer is specific to the type of device employed and can involve the use of an appropriate propellant material, in addition to the usual diluents, adjuvants and/or carriers useful in therapy.

In some embodiments, additional agents to aid in treatment of the subject can be administered before or following treatment with the lung progenitor cells described herein. Such additional agents can be used to prepare the lung tissue for administration of the progenitor cells. Alternatively the additional agents can be administered after the lung progenitor cells to support the engraftment and growth of the administered cell in the damaged lung. Such additional agents can be formulated for use with a metered-dose inhaler device, which generally comprises a finely divided powder containing a protein or small molecule suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid can also be useful as a surfactant.

Formulations for dispensing from a powder inhaler device can comprise a finely divided dry powder containing proteins or small molecules and can also include a bulking agent, such as lactose, sorbitol, sucrose, or mannitol in amounts which facilitate dispersal of the powder from the device, e.g., 50 to 90% by weight of the formulation. Protein agents should most advantageously be prepared in particulate form with an average particle size of less than 10 µm (or microns), most preferably 0.5 to 5 µm, for most effective delivery to the distal lung.

Nasal delivery of protein or other agents in addition to the lung progenitor cells or progeny thereof is also contemplated. Nasal delivery allows the passage of the protein or other agent to the blood stream directly after administering the therapeutic product to the nose, without the necessity for deposition of the product in the lung. Formulations for nasal delivery include those with dextran or cyclodextran.

The efficacy of treatment can be determined by the skilled clinician. However, a treatment is considered "effective treatment," as the term is used herein, if any one or all of the symptoms, or other clinically accepted symptoms or markers of lung disease, lung injury and/or a lung disorder are reduced, e.g., by at least 10% following treatment with a composition comprising human lung progenitor cells as described herein. Methods of measuring these indicators are known to those of skill in the art and/or described herein.

Indicators of lung disease or lung disorder, or lung injury include functional indicators, e.g., measurement of lung capacity and function, and oxygen saturation (e.g., tissue oxygen saturation or systemic arterial oxygen saturation), as well as biochemical indicators.

For idiopathic pulmonary fibrosis, for example, improved symptoms include an increase of at least 10% of predicted forced vital capacity (FVC) relative to values prior to treatment. FVC is the total volume of air expired after a full inspiration. Patients with obstructive lung disease usually have a normal or only slightly decreased vital capacity. Patients with restrictive lung disease have a decreased vital capacity.

Another measure is FEV1 (Forced Expiratory Volume in 1 Second). This is the volume of air expired in the first second during maximal expiratory effort. The FEV1 is reduced in both obstructive and restrictive lung disease. The FEV1 is reduced in obstructive lung disease because of increased airway resistance. It is reduced in restrictive lung disease because of the low vital capacity.

A related measure is FEV1/FVC. This is the percentage of the vital capacity which is expired in the first second of maximal expiration. In healthy patients the FEV1/FVC is usually around 70%. In patients with obstructive lung disease FEV1/FVC decreases and can be as low as 20-30% in severe obstructive airway disease. Restrictive disorders have a near normal FEV1/FVC.

Where necessary or desired, animal models of lung injury or lung disease can be used to gauge the effectiveness of a particular composition as described herein. As one example, the bleomycin-induced lung injury model of acute lung injury (ALI) can be used. Animal models of lung function are useful for monitoring bronchoconstriction, allergic response, late airway hyperresponsiveness in response to inhaled allergens, among other endpoints and can include, for example, head-out plethysmography or body-plethysmography models (see e.g., Hoymann, H G et al., *J Pharmacol Toxicol Methods* (2007) 55(1):16-26). Exemplary animal models for asthma, including models of allergic asthma (e.g., acute and chronic allergic asthma), are known in the art. See e.g., Nials and Uddin. (2008) *Dis Model Mech* 1:213-220; Zosky and Sly (2007) *Clin Exp Allergy* 37(7): 973-88; and Kumar and Foster. (2002) *Am J Respir Cell Mol Biol* 27(3):267-72. Animal models of pneumonia are reviewed by Mizgerd and Skerrett (2008) *Am J Physiol Lung Cell Mol Physiol* 294:L387-L398. In addition, small animal imaging can be applied to lung pathophysiologies (Brown R H, et al., *Proc Am Thorac Soc* (2008) 5:591-600).

Screening Assays

The compositions described herein are useful to screen for agents for inducing differentiation of human lung progenitor cells or for the treatment of a lung disease or disorder.

In some embodiments, the isolated human lung progenitor cells or isolated human disease-specific lung cells derived from such human lung progenitor cells can be used in methods, assays, systems and kits to develop specific in vitro assays. Such assays for drug screening and toxicology studies have an advantage over existing assays because they are of human origin, and do not require immortalization of cell lines, nor do they require tissue from cadavers, which poorly reflect the physiology of normal human cells. For example, the methods, assays, systems, and kits described herein can be used to identify and/or test agents that can promote differentiation along the lung lineage. In addition to, or alternatively, the methods, assays, systems, and kits can be used to identify and/or test for agents useful in treating a lung disease or disorder, or for preventing/treating a lung injury.

Accordingly, provided herein are methods for screening a test compound for biological activity, the method comprising (a) contacting an isolated human lung progenitor cell as described herein, or its progeny, with a test compound and (b) determining any effect of the compound on the cell. In one embodiment, the screening method further comprises generating a human lung progenitor cell or a human lung disease-specific cell as disclosed herein. In one embodiment, the lung progenitor cell is first differentiated to a desired lung cell phenotype. The effect on the cell can be one that is observable directly or indirectly by use of reporter molecules.

As used herein, the term "biological activity" or "bioactivity" refers to the ability of a test compound to affect a biological sample. Biological activity can include, without limitation, elicitation of a stimulatory, inhibitory, regulatory, toxic or lethal response in a biological assay. For example, a biological activity can refer to the ability of a compound to modulate the effect of an enzyme, block a receptor, stimulate a receptor, modulate the expression level of one or more genes, modulate cell proliferation, modulate cell division, modulate cell metabolism, modulate differentiation, modulate cell morphology, or a combination thereof. In some instances, a biological activity can refer to the ability of a test compound to produce a toxic effect in a biological sample.

As discussed above, the specific lineage can be a lineage which is phenotypic and/or genotypic of a disease (e.g., a lung disease). Alternatively, the specific lineage can be a lineage which is phenotypic and/or genotypic of an organ and/or tissue or a part thereof (e.g., lung).

As used herein, the term "test compound" or "candidate agent" refers to an agent or collection of agents (e.g., compounds) that are to be screened for their ability to have an effect on the cell. Test compounds can include a wide variety of different compounds, including chemical compounds, mixtures of chemical compounds, e.g., polysaccharides, small organic or inorganic molecules (e.g. molecules having a molecular weight less than 2000 Daltons, less than 1000 Daltons, less than 1500 Dalton, less than 1000 Daltons, or less than 500 Daltons), biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

Depending upon the particular embodiment being practiced, the test compounds can be provided free in solution, or can be attached to a carrier, or a solid support, e.g., beads. A number of suitable solid supports can be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group.

A number of small molecule libraries are known in the art and commercially available. These small molecule libraries can be screened using the screening methods described herein. A chemical library or compound library is a collection of stored chemicals that can be used in conjunction with the methods described herein to screen candidate agents for a particular effect. A chemical library comprises information regarding the chemical structure, purity, quantity, and physiochemical characteristics of each compound. Compound libraries can be obtained commercially, for example, from Enzo Life Sciences™, Aurora Fine Chemicals™ Exclusive Chemistry Ltd.™, ChemDiv, ChemBridge™, TimTec Inc.™, AsisChem™, and Princeton Biomolecular Research™, among others.

Without limitation, the compounds can be tested at any concentration that can exert an effect on the cells relative to a control over an appropriate time period. In some embodiments, compounds are tested at concentrations in the range of about 0.01 nM to about 100 mM, about 0.1 nM to about 500 µM, about 0.1 µM to about 20 µM, about 0.1 µM to about 10 µM, or about 0.1 µM to about 5 µM.

The compound screening assay can be used in a high through-put screen. High through-put screening is a process in which libraries of compounds are tested for a given activity. High through-put screening seeks to screen large numbers of compounds rapidly and in parallel. For example, using microtiter plates and automated assay equipment, a laboratory can perform as many as 100,000 assays per day in parallel.

The compound screening assays described herein can involve more than one measurement of the cell or reporter function (e.g., measurement of more than one parameter and/or measurement of one or more parameters at multiple points over the course of the assay). Multiple measurements can allow for following the biological activity over incubation time with the test compound. In one embodiment, the reporter function is measured at a plurality of times to allow monitoring of the effects of the test compound at different incubation times.

The screening assay can be followed by a subsequent assay to further identify whether the identified test compound has properties desirable for the intended use. For example, the screening assay can be followed by a second assay selected from the group consisting of measurement of any of: bioavailability, toxicity, or pharmacokinetics, but is not limited to these methods.

Kits

Another aspect of the technology described herein relates to kits for treating a lung disease or disorder, kits for screening a candidate agent and/or kits for differentiating a human stem cell to a human lung progenitor cell or for differentiating a human lung progenitor cell to a specific type or types of human lung cell(s). Described herein are kit components that can be included in one or more of the kits described herein.

In one embodiment, the kits described herein can include a human lung progenitor cell, as that term is used herein. In one embodiment, one or more signaling pathway agonists or antagonists that promote differentiation of a stem cell are included in the kit. In another embodiment, a component described herein such as one or more TGF-β receptor inhibitor(s), one or more BMP agonists, one or more FGF agonists, and instructions for converting a stem cell (e.g., embryonic stem cell, isolated pluripotent stem cell, anterior foregut endoderm cell, or definitive endoderm cell) to a human lung progenitor cell, e.g., using a method described herein.

Another aspect of the technology disclosed herein relates to kits to produce human lung progenitor cells according to the methods as disclosed herein. In some embodiments, the components described herein can be provided singularly or in any combination as a kit. The kit includes the components described herein, e.g., a composition(s) that includes a compound(s) described herein, e.g., a compound or cocktail of compounds or reagents for differentiating a human stem cell to a lung progenitor cell. Such kits can optionally include one or more agents that permit the detection of a lung progenitor cell marker or a lung cell marker or set thereof. In addition, the kit optionally comprises informational material.

In some embodiments, the compound in the kit can be provided in a watertight or gas tight container which in some embodiments is substantially free of other components of the kit. For example, a signaling pathway or differentiation pathway modulating compound can be supplied in more than one container, e.g., it can be supplied in a container having sufficient reagent for a predetermined number of differentiation reactions, e.g., 1, 2, 3 or greater. One or more compound as described herein can be provided in any form, e.g., liquid, dried or lyophilized form. It is preferred that the compound(s) described herein are substantially pure and/or sterile. When the one or more signaling pathway modulating compounds described herein is provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The informational material can be descriptive, instructional, marketing or other material that relates to the methods described herein and/or the use of a compound(s)

described herein for the methods described herein. The informational material of the kits is not limited in its form. In one embodiment, the informational material can include information about production of the compound, molecular weight of the compound, concentration, date of expiration, batch or production site information, and so forth. In one embodiment, the informational material relates to methods for using or administering the compound.

In one embodiment, the informational material can include instructions to administer a human lung progenitor cell as described herein in a suitable manner to effect treatment of a lung injury or a lung disease or disorder, e.g., in a suitable dose, dosage form, or mode of administration (e.g., a dose, dosage form, or mode of administration described herein). In another embodiment, the informational material can include instructions for differentiating a human stem cell to a human lung progenitor cell. Alternatively, the informational material can include instructions for screening a candidate agent for treating a lung disease or disorder.

In addition to a compound(s) described herein, the composition of the kit can include other ingredients, such as a solvent or buffer, a stabilizer, a preservative, and/or an additional agent, e.g., for differentiating stem cells (e.g., in vitro) or for treating a condition or disorder described herein. Alternatively, the other ingredients can be included in the kit, but in different compositions or containers than a cell or signaling pathway or differentiation pathway modulating compound described herein. In such embodiments, the kit can include instructions for admixing a compound(s) described herein and the other ingredients, or for using a compound(s) described herein together with the other ingredients, e.g., instructions on combining the two agents prior to use or administration.

The kit can include a component for the detection of a marker for human lung progenitor cells, ES cells iPS cells, thyroid lineage cells, neuronal lineage cells etc. In addition, the kit can include one or more antibodies that bind a cell marker, or primers for an RT-PCR or PCR reaction, e.g., a semi-quantitative or quantitative RT-PCR or PCR reaction. Such components can be used to assess the activation of lung cell-specific markers or the loss of ES cell, iPSC, thyroid lineage, or neuronal lineage markers. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The kit can also include one or more reagents for enhancing the efficiency of induced pluripotent stem cell production, such as an HDAC inhibitor (e.g., valproic acid) or a DNA methyltransferase inhibitor (e.g., 5azaC).

In one embodiment, the kit comprises a cell or tissue medium for definitive endoderm generation. In one embodiment, the medium comprises B27, Activin A and ZSTK474. An exemplary definitive endoderm generation medium comprises 2% B27, 20 ng/mL Activin A, and 0.2-0.5 µM ZSTK474.

The kit will typically be provided with its various elements included in one package, e.g., a fiber-based, e.g., a cardboard, or polymeric, e.g., a Styrofoam box. The enclosure can be configured so as to maintain a temperature differential between the interior and the exterior, e.g., it can provide insulating properties to keep the reagents at a preselected temperature for a preselected time.

The present invention may be as defined in any one of the following numbered paragraphs.

1. An isolated human Nkx2.1 positive, Sox2 positive proximal airway multipotent progenitor cell.
2. The isolated cell of paragraph 1, wherein the cell is Tuj1 negative and Pax8 negative.
3. The isolated cell of paragraph 1, wherein the cell is proliferative and differentiates into an airway basal stem cell, a ciliated cell, a Clara cell, a neuroendocrine cell, or a squamous epithelial cell under chosen differentiation conditions.
4. An isolated human Nkx2.1 positive, Sox9 positive, distal multipotent lung progenitor cell.
5. The isolated cell of paragraph 4, wherein the cell is FoxP2 positive and/or ID2 positive.
6. The isolated cell of paragraph 4, wherein the cell is proliferative and differentiates into any epithelial lung cell when placed under chosen differentiation conditions.
7. The isolated cell of paragraph 6, wherein the cell differentiates into an airway basal stem cell, a ciliated cell, a Clara cell, a mucin secreting goblet cell, a type I pneumocyte, a type II pneumocyte, a squamous epithelial cell, a bronchioalveolar stem cell, a bronchioalveolar duct junction stem cell, a migratory CK14+ cell, or a neuroendocrine cell when placed under chosen differentiation conditions.
8. An isolated human Nkx2.1 positive, p63 positive multipotent airway basal stem cell.
9. The isolated cell of paragraph 8, wherein the cell is proliferative and differentiates into a ciliated cell, a Clara cell, a mucin secreting goblet cell, or a basal cell when placed under chosen differentiation conditions.
10. The isolated cell of paragraph 8, wherein the multipotent airway basal stem cell does not express a Clara cell marker, a ciliated cell marker, a neuroendocrine cell marker, or a squamous cell marker.
11. The isolated cell of paragraph 8, wherein the cell is Sox2 positive.
12. The isolated cell of paragraph 8, wherein the cell is CK5 positive and/or NGFR positive.
13. The isolated cell of paragraph 1, 5, or 8, wherein the cell is a disease-specific cell.
14. A composition comprising an isolated human Nkx2.1 positive, Sox2 positive proximal airway multipotent progenitor cell and a scaffold.
15. The composition of paragraph 14, wherein the scaffold is implantable in a subject.
16. The composition of paragraph 14, wherein the cell is autologous to the subject into which the composition is being implanted.
17. The composition of paragraph 14, wherein the scaffold is biodegradable.
18. The composition of paragraph 14, wherein the scaffold comprises a natural fiber, a synthetic fiber, decellularized lung tissue, or a combination thereof.
19. The composition of paragraph 18, wherein the natural fiber is selected from the group consisting of collagen, fibrin, silk, thrombin, chitosan, chitin, alginic acid, hyaluronic acid, and gelatin.
20. The composition of paragraph 19, wherein the synthetic fiber is selected from the group consisting of: representative bio-degradable aliphatic polyesters such as polylactic acid (PLA), polyglycolic acid (PGA), poly(D,L-lactide-co-glycolide) (PLGA), poly(caprolactone), diol/diacid aliphatic polyester, polyester-amide/polyester-urethane, poly(valerolactone), poly(hydroxyl butyrate), polybutylene terephthalate (PBT), polyhydroxyhexanoate (PHH), polybutylene succinate (PBS), and poly(hydroxyl valerate).

21. The composition of paragraph 14, wherein the proximal airway multipotent progenitor cell is Tuj1 negative and/or Pax8 negative.

22. A composition comprising an isolated human Nkx2.1 positive, Sox9 positive, distal multipotent lung progenitor cell and a scaffold.

23. The composition of paragraph 22, wherein the multipotent lung progenitor cell is FoxP2 positive and/or ID2 positive.

24. The composition of paragraph 22, wherein the scaffold is implantable in a subject.

25. The composition of paragraph 22, wherein the cell is autologous to the subject into which the composition is being implanted.

26. The composition of paragraph 22, wherein the scaffold is biodegradable.

27. The composition of paragraph 22, wherein the scaffold comprises a natural fiber, a synthetic fiber, decellularized lung, or a combination thereof.

28. The composition of paragraph 27, wherein the natural fiber is selected from the group consisting of collagen, fibrin, silk, thrombin, chitosan, chitin, alginic acid, hyaluronic acid, and gelatin.

29. The composition of paragraph 28, wherein the synthetic fiber is selected from the group consisting of: representative bio-degradable aliphatic polyesters such as polylactic acid (PLA), polyglycolic acid (PGA), poly(D,L-lactide-co-glycolide) (PLGA), poly(caprolactone), diol/diacid aliphatic polyester, polyester-amide/polyester-urethane, poly(valerolactone), poly(hydroxyl butyrate), polybutylene terephthalate (PBT), polyhydroxyhexanoate (PHH), polybutylene succinate (PBS), and poly(hydroxyl valerate).

30. A composition comprising an isolated human Nkx2.1 positive, p63 positive multipotent airway basal stem cell and a scaffold.

31. The composition of paragraph 30, wherein the airway basal stem cell is CK5 positive and/or NGFR positive.

32. The composition of paragraph 30, wherein the scaffold is implantable in a subject.

33. The composition of paragraph 32, wherein the cell is autologous to the subject into which the composition is being implanted.

34. The composition of paragraph 30, wherein the scaffold is biodegradable.

35. The composition of paragraph 30, wherein the scaffold comprises a natural fiber, a synthetic fiber, decellularized lung tissue, or a combination thereof.

36. The composition of paragraph 35, wherein the natural fiber is selected from the group consisting of collagen, fibrin, silk, thrombin, chitosan, chitin, alginic acid, hyaluronic acid, and gelatin.

37. The composition of paragraph 36, wherein the synthetic fiber is selected from the group consisting of: representative bio-degradable aliphatic polyesters such as polylactic acid (PLA), polyglycolic acid (PGA), poly(D,L-lactide-co-glycolide) (PLGA), poly(caprolactone), diol/diacid aliphatic polyester, polyester-amide/polyester-urethane, poly(valerolactone), poly(hydroxyl butyrate), polybutylene terephthalate (PBT), polyhydroxyhexanoate (PHH), polybutylene succinate (PBS), and poly(hydroxyl valerate).

38. The composition of paragraph 14, 22 or 30, wherein the cell is a disease-specific cell.

39. A method of generating a human lung progenitor cell or population of human lung progenitor cells that is Nkx2.1 positive, Tuj1 negative and Pax8 negative, the method comprising contacting a human foregut endoderm cell with FGF2, WNT and BMP4, each for a time and at a concentration sufficient to permit differentiation of said human foregut endoderm cell to an Nkx2.1 positive, Tuj1 negative, Pax8 negative lung progenitor cell.

40. The method of paragraph 39, wherein the contacting step is performed for at least 2 days.

41. The method of paragraph 39, further comprising contacting the Nkx2.1 positive, Tuj1 negative, Pax8 negative lung progenitor cell with BMP7, FGF7, a WNT antagonist, and a MAPKK/ERK antagonist, each for a time and at a concentration sufficient to permit differentiation of the Nkx2.1 positive, Tuj1 negative, Pax8 negative lung progenitor cell to a Nkx2.1 positive, Sox2 positive proximal airway multipotent progenitor cell.

42. The method of paragraph 41, wherein the Wnt antagonist comprises IWR-1.

43. The method of paragraph 41, wherein the MAPKK/ERK antagonist comprises PD98059.

44. The method of paragraph 41, wherein the contacting step is performed for at least 4 days.

45. The method of paragraph 41, further comprising contacting the Nkx2.1 positive, Tuj1 negative, Pax8 negative lung progenitor cell with BMP7, FGF7, a WNT antagonist, and a MAPKK/ERK antagonist each for a time and at a concentration sufficient to permit differentiation of the Nkx2.1 positive, Tuj1 negative, Pax8 negative lung progenitor cell to an Nkx2.1 positive, Sox9 positive distal multipotent lung progenitor cell.

46. The method of paragraph 45, wherein the Wnt antagonist comprises IWR-1.

47. The method of paragraph 45, wherein the MAPKK/ERK antagonist comprises PD98059.

48. The method of paragraph 45, wherein the contacting step is performed for at least 4 days.

49. The method of paragraph 39, wherein the culture of foregut endoderm cells are derived from embryonic stem (ES) cells or induced pluripotent stem cells (iPSCs).

50. The method of paragraph 39, further comprising contacting a culture of Nkx2.1 positive, Tuj1 negative, Pax8 negative cells with B27, BMP7, FGF7, and a WNT antagonist, each for a time and at a concentration sufficient to permit differentiation of said Nkx2.1 positive, Tuj1 negative, Pax8 negative lung progenitor cell to an Nkx2.1 positive, p63 positive multipotent airway basal stem cell.

51. The method of paragraph 39, further comprising contacting the culture of Nkx2.1 positive, Tuj1 negative, Pax8 negative cells with Noggin.

52. The method of paragraph 50, wherein the contacting step is performed for at least 10 days.

53. A method for treating a lung disease or disorder, or lung injury in a subject, the method comprising: administering a composition comprising an isolated human lung progenitor cell and a pharmaceutically acceptable carrier to a subject having a lung disease or disorder, or lung injury.

54. The method of paragraph 53, wherein the isolated human lung progenitor cell is selected from the group consisting of: an Nkx2.1 positive, Sox2 positive proximal airway multipotent progenitor cell; an Nkx2.1 positive, Sox9 positive distal multipotent lung progenitor cell, an Nkx2.1 positive, p63 positive multipotent airway basal stem cell, or a differentiated cell thereof.

55. The method of paragraph 53, wherein the proximal airway multipotent progenitor cell is Tuj1 negative and/or Pax8 negative.

56. The method of paragraph 53, wherein the distal multipotent lung progenitor cell is FoxP2 and/or ID2 positive.
57. The method of paragraph 53, wherein the airway basal stem cell is CK5 positive and/or NGFR positive.
58. The method of paragraph 53, wherein the composition is administered to the lung.
59. The method of paragraph 53, wherein the isolated human lung progenitor cell is autologous to the subject to which the composition is being administered.
60. The method of paragraph 53, wherein the composition further comprises a scaffold.
61. The method of paragraph 60, wherein the scaffold is implantable in a subject.
62. The method of paragraph 60, wherein the scaffold is biodegradable.
63. The method of paragraph 60, wherein the scaffold comprises a natural fiber, a synthetic fiber, decellularized lung tissue, or a combination thereof.
64. The method of paragraph 60, wherein the scaffold comprises an agent that promotes differentiation of the isolated human lung progenitor cell.
65. The method of paragraph 60, wherein the composition is formulated for aerosol delivery.
66. A method of screening for an agent to treat a lung disease or disorder, the method comprising:
    (a) culturing a population of human disease-specific airway cells produced by in vitro differentiation of a human disease specific lung progenitor cell in the presence and absence of a candidate agent for treating a lung disease or disorder,
    (b) comparing the expression or activity of at least one marker that is upregulated in the disease or comparing the expression or activity of at least one marker that is downregulated in the disease in the presence and absence of the candidate agent,
    wherein a decrease in the expression or activity of at least one upregulated disease marker or an increase in the expression or activity of at least one downregulated disease marker identifies the candidate agent as a candidate for the treatment of the lung disease or disorder in a subject.
67. The method of paragraph 66, wherein the method further comprises steps before step (a) of differentiating a population of isolated human disease-specific lung progenitor cells to a culture of human disease-specific airway cells.
68. The method of paragraph 66, wherein the method further comprises steps before step (a) of differentiating a population of induced pluripotent stem cells derived from a subject having a lung disease or disorder to a population of isolated human disease-specific lung progenitor cells.
69. The method of paragraph 66, wherein the candidate agent comprises a small molecule, a protein, a polypeptide, an antibody or an antigen binding fragment thereof, or a nucleic acid.
70. The method of paragraph 66, wherein the human lung progenitor cell is selected from the group consisting of: a human Nkx2.1 positive, Sox2 positive proximal airway multipotent progenitor cell, a human Nkx2.1 positive, Sox9 positive distal multipotent lung progenitor cell, and a human Nkx2.1 positive, p63 positive multipotent airway basal stem cell.
71. The method of paragraph 70, wherein the human Nkx2.1 positive, Sox2 positive proximal airway multipotent progenitor cell, and the human Nkx2.1 positive, Sox9 positive distal multipotent lung progenitor cell are made by a method comprising contacting an Nkx2.1 positive, Tuj1 negative, Pax8 negative lung progenitor cell with BMP7, FGF7, a WNT antagonist, and a MAPKK/ERK antagonist each for a time and at a concentration sufficient to permit the Nkx2.1 positive, Tuj1 negative, Pax8 negative lung progenitor cell to differentiate to an Nkx2.1 positive, Sox9 positive proximal airway multipotent progenitor cell, or to an Nkx2.1 positive, Sox9 positive distal multipotent lung progenitor cell.
72. The method of paragraph 71, wherein the contacting step is performed for at least 4 days.
73. The method of paragraph 70, wherein the human Nkx2.1 positive, p63 positive multipotent airway basal stem cell is made by a method comprising contacting an Nkx2.1 positive, Tuj1 negative, Pax8 negative cell with B27, BMP7, FGF7, and a WNT antagonist, each for a time and at a concentration sufficient to permit differentiation of said Nkx2.1 positive, Tuj1 negative, Pax8 negative lung progenitor cell to an Nkx2.1 positive, p63 positive multipotent airway basal stem cell.
74. The method of paragraph 73, further comprising contacting the Nkx2.1 positive, Tuj1 negative, Pax8 negative cell with Noggin.
75. The method of paragraph 73, wherein the contacting step is performed for at least 10 days.
76. A method of screening for an agent to induce differentiation of a human lung progenitor cell, the method comprising:
    (a) culturing an Nkx2.1 positive, Tuj1 negative, Pax8 negative human lung progenitor cell in the presence and absence of a candidate differentiation agent,
    (b) comparing the expression or activity of at least one marker that is upregulated during differentiation of the lung progenitor cell to a more differentiated state or comparing the expression or activity of at least one marker that is downregulated during differentiation of the lung progenitor cell to a more differentiated state in the presence and absence of the candidate agent,
    wherein a decrease in the expression or activity of at least one upregulated differentiation marker or an increase in the expression or activity of at least one downregulated differentiation marker is indicative that the candidate agent can be used to induce differentiation of an isolated human lung progenitor cell in a subject.
77. The method of paragraph 76, wherein the method further comprises steps before step (a) of differentiating an embryonic stem cell or induced pluripotent stem cell to a human lung progenitor cell.
78. The method of paragraph 76, wherein the candidate agent comprises a small molecule, a protein, a polypeptide, an antibody, or a nucleic acid.
79. The method of paragraph 76, wherein the human lung progenitor cell is selected from the group consisting of: a human Nkx2.1 positive, Sox2 positive proximal airway multipotent progenitor cell, a human Nkx2.1 positive, Sox9 positive distal multipotent lung progenitor cell, and a human Nkx2.1 positive, p63 positive multipotent airway basal stem cell.
80. The method of paragraph 79, wherein the human Nkx2.1 positive, Sox2 positive proximal airway multipotent progenitor cell, and the human Nkx2.1 positive, Sox9 positive distal multipotent lung progenitor cell are made by a method comprising contacting an Nkx2.1 positive, Tuj1 negative, Pax8 negative human lung progenitor cell with BMP7, FGF7, a WNT antagonist, and a MAPKK/ERK antagonist each for a time and at a concentration sufficient to permit the Nkx2.1 positive, Tuj1 negative, Pax8 negative lung progenitor cell to differentiate to an Nkx2.1 positive, Sox9 positive proximal airway multipotent progenitor cell, or to an Nkx2.1 positive, Sox9 positive distal multipotent lung progenitor cell.

81. The method of paragraph 80, wherein the contacting step is performed for at least 4 days.

82. The method of paragraph 79, wherein the human Nkx2.1 positive, p63 positive multipotent airway basal stem cell is made by a method comprising contacting an Nkx2.1 positive, Tuj1 negative, Pax8 negative cell with B27, BMP7, FGF7, and a WNT antagonist, each for a time and at a concentration sufficient to permit differentiation of the Nkx2.1 positive, Tuj1 negative, Pax8 negative lung progenitor cell to an Nkx2.1 positive, p63 positive multipotent airway basal stem cell.

83. The method of paragraph 82, further comprising contacting the Nkx2.1 positive, Tuj1 negative, Pax8 negative cell with Noggin.

84. The method of paragraph 82, wherein the contacting step is performed for at least 10 days.

85. A kit for treating a lung disease or disorder, the kit comprising: a cell of paragraph 1, 5, or 9, a pharmaceutically acceptable carrier, and instructions for treating a lung disease or disorder.

86. The kit of paragraph 85, further comprising a scaffold.

87. A kit for screening a candidate agent, the kit comprising: a cell of paragraph 1, 5, or 8, one or more agents for detecting lung specific cell surface markers, and instructions therefore.

88. The kit of paragraph 87, further comprising a cell culture medium, a growth factor, and/or a differentiation agent.

89. A kit for differentiating a human stem cell to a human lung progenitor cell, the kit comprising:
(i) two or more of BMP4, FGF2, WNT, BMP7, FGF7, a WNT antagonist, a PI3 kinase inhibitor, Activin A, Noggin, B27, and retinoic acid, optionally provided in unit doses;
(ii) optionally, a cell culture medium;
(iii) one or more agents for detecting a lung cell-specific surface marker; and
(iii) instructions therefore.

90. A cell or tissue medium comprising: B27, Activin A, and ZSTK474.

91. The medium of paragraph 90, wherein the concentration of B27 is 1%-5%.

92. The medium of paragraph 91, wherein the concentration of B27 is 2%.

93. The medium of paragraph 90, wherein the concentration of Activin A is 10-40 ng/mL.

94. The medium of paragraph 93, wherein the concentration of Activin A is 20 ng/mL.

95. The medium of paragraph 90, wherein the concentration of ZSTK474 is 0.2-0.5 µM.

96. The medium of paragraph 90, wherein the medium comprises the components of RPMI medium.

97. A cell or tissue medium comprising: CHIR9902, PIK-75, Dorsomorphin, and FGF2.

99. The medium of paragraph 97, wherein the concentration of CHIR9902 is in the range of 0.1-1 µM.

100. The medium of paragraph 97, wherein the concentration of PIK-75 comprises 0.01-0.1 µM.

101. The medium of paragraph 97, wherein the concentration of dorsomorphin comprises 1-5 µM.

102. The medium of paragraph 97, wherein the concentration of FGF2 comprises 10-100 ng/mL.

103. The medium of paragraph 97, further comprising a drug selected from the group consisting of: GF-109203X, Ro31-8220, Pp242, PIK-75, ZSTK474, PMA, carvedilol, corticosterone, triclabendazole, benproperine phosphate, phenothiazine, and methotrexate.

104. A method of generating a human lung progenitor cell or population of human lung progenitor cells that is Nkx2.1 positive, Tuj1 negative, and Pax8 negative, the method comprising contacting a human foregut endoderm cell with a Wnt agonist, a PIK3 kinase inhibitor, a BMP antagonist, and a drug selected from the group consisting of GF-109203X, Ro31-8220, Pp242, PIK-75, ZSTK474, PMA, carvedilol, corticosterone, triclabendazole, benproperine phosphate, phenothiazine, and methotrexate, each for a time and at a concentration sufficient to permit differentiation of said human foregut endoderm cell to an Nkx2.1 positive, Tuj1 negative, Pax8 negative lung progenitor cell.

105. The method of paragraph 104, wherein the contacting step is performed for at least 2 days.

106. The method of paragraph 104, wherein the Wnt agonist comprises CHIR9902.

107. The method of paragraph 106, wherein the concentration of CHIR9902 is in the range of 0.1-1 µM.

108. The method of paragraph 104, wherein the PI3 kinase inhibitor comprises PIK-75.

109. The method of paragraph 108, wherein the concentration of PIK-75 comprises 0.01-0.1 µM.

110. The method of paragraph 104, wherein the BMP antagonist comprises Dorsomorphin.

111. The method of paragraph 110, wherein the concentration of dorsomorphin comprises 1-5 µM.

112. The method of paragraph 104, wherein the growth factor comprises FGF2.

113. The method of paragraph 112, wherein the concentration of FGF2 comprises 10-100 ng/mL.

114. A method for generating a definitive endoderm cell or population of definitive endoderm cells, the method comprising contacting an iPSC or ESC with B27, Activin A, and ZSTK474, each for a time and at a concentration sufficient to permit differentiation of the iPSC or ESC to a definitive endoderm cell.

115. The method of paragraph 114, wherein the generation of a definitive endoderm cell is determined by FOXA2/SOX17 co-staining or by FACS analysis with cKit/CXCR4 and/or cKit/EpCAM combination.

116. The method of paragraph 114, wherein the concentration of B27 is 1%-5%.

117. The method of paragraph 116, wherein the concentration of B27 is 2%.

118. The method of paragraph 114, wherein the concentration of Activin A is 10-40 ng/mL.

119. The method of paragraph 118, wherein the concentration of Activin A is 20 ng/mL.

120. The method of paragraph 114, wherein the concentration of ZSTK474 is 0.2-0.5 µM.

EXAMPLES

The discovery of embryonic stem cells (ES cells) and induced pluripotent stem cells (iPSCs) has resulted in an unprecedented opportunity to produce tissue-specific cell types that can be used in human disease modeling, drug screening, and patient-specific therapies. Although many iPSCs from patients with lung diseases are currently being produced, the major obstacle preventing the actual development of human lung disease models using these cells is the inability to convert them into lung progenitors and then subsequently into differentiated pulmonary epithelial cell types for therapeutic treatment or to study their characteristics in the laboratory. Several attempts to produce pulmonary epithelial cells from mouse and human ES cells have been made. In many cases, investigators have focused on the generation of type II pneumocytes (Van Vranken et al., 2005; Samadikuchaksaraei et al., 2006; Wang et al., 2007). Fewer studies have targeted the differentiation of airway epithelial cells from pluripotent stem cells despite the fact that airway diseases such as asthma, Cystic Fibrosis, bronchitis and bronchogenic carcinoma are, in aggregate, more prevalent than the diseases of the alveoli such as emphysema. Furthermore, when the lung primordium forms, the first two recognizable progenitors are the multipotent embryonic lung progenitors and the airway progenitors. The production of these two progenitors is expected, therefore, to permit the differentiation of each type of lung epithelial cell.

The large airway epithelium of the mouse and the majority of the human airway epithelium is comprised of four major cell types: basal stem cells abutting the basement membrane, secretory detoxifying Clara cells with P450 machinery primarily in the mouse, ciliated cells that propel mucous out of the respiratory tree, and goblet cells that respond to injury or inflammation and secrete the mucous. Prior attempts (Coraux et al., 2005; Van Haute et al., 2009) to generate functional pulmonary epithelium from ES cells were characterized by the stochastic production of limited numbers of cells and the generation of mixed cell populations that contain undifferentiated pluripotent stem cells that carry a significant risk of teratoma formation after transplantation. Others have utilized incompletely defined media to induce airway cell differentiation (such as the exposure of human ES cells to tumor cell extract; Roszell et al., 2009) or used genetically modified pluripotent stem cells that were selected based upon the presence of a drug resistance gene (Wang et al., 2007). Unfortunately, genetic modulation raises the possibility of the introduction of deleterious genetic mutations in the resulting cells.

Given the difficulty of obtaining adult human airway stem cells with which to model human lung disease, the studies described herein seek to generate normal and disease-specific lung epithelial cells from human normal and lung disease-specific iPSCs. This is particularly important because murine models of lung disease often do not phenocopy human lung disease. A prime example is the Cftr knockout mouse that does not display the Cystic Fibrosis disease-associated lung pathology observed in human patients (Snouwaert et al., 1992; Clarke et al., 1992; Guilbault et al., 2006). Furthermore, iPSC-derived epithelial cells will reflect the pre-pathologic state of lung cells in which multiple secondary changes, such as those associated with inflammation or infection, do not obscure the effects of the initial genetic abnormality in disease pathogenesis.

The overall strategy described herein employs a step-wise differentiation approach. Mechanisms that regulate mouse embryonic endoderm regionalization, lung specification and subsequent progenitor patterning and growth have been well studied (reviewed in Morrisey and Hogan, 2010). The onset of lung specification within the endoderm is accompanied by Nkx2.1 expression and the downregulation of Sox2 along the dorsal-ventral axis of the gut tube (Lazzaro et al., 1991; Minoo et al., 1999; Que et al., 2009). Nkx2.1 is the earliest marker of lung endoderm distinguishing it from the rest of the foregut endoderm. Later, Sox2 expression again increases in the area of the future trachea, bronchus and bronchioles while Sox9, FoxP2 and ID2 remain in the distal lung bud tip and are markers of a multipotent embryonic lung progenitor population (Perl et al., 2005; Shu et al., 2007; Rawlins et al., 2009). Then, Nkx2.1+Sox2+ airway progenitor cells located in embryonic trachea differentiate into p63+ airway basal stem cells (Que et al., 2009). The mouse large airway epithelium is highly reminiscent of the majority of human airway epithelium (Rock et al., 2010; Rock et al., 2009; Evans et al., 2001) and can, therefore, be used as a model to study human airway disease.

The inventors focused on producing Nkx2.1+ lung endoderm that is devoid of Nkx2.1+ thyroid endoderm and neural progenitors. A recent report using human ES cells demonstrated that a differentiation strategy based on mimicking mouse gut organogenesis led to the production of anterior foregut cells and Nkx2.1+ cells with efficiencies up to 30% (Green et al., 2011). However, these Nkx2.1+ cells were not demonstrated to be composed of purely lung progenitors. TUJ1 (a marker of neuronal tissue) and PAX8 (a marker of thyroid tissue) expression was not evaluated at the single cell level by co-antibody staining with an Nkx2.1 antibody. Development of a novel strategy to produce Nkx2.1+ progenitors that reflect only lung and not thyroid or brain differentiation is therefore needed, and the technique must be applicable to human disease-specific iPSCs in order for the technique to become widely relevant to the study of human lung disease.

Described herein is an efficient and consistent step-wise differentiation method to generate definitive endoderm (DE), foregut endoderm, early lung endoderm, multipotent Nkx2.1+ embryonic lung progenitor cells and airway progenitor cells beginning with mouse ES cells (FIG. 1) and subsequently with normal and lung disease-specific human iPSCs. The inventors show that a high dose of Activin, transient WNT activation and staged BMP4 inhibition converts ES cells into definitive endoderm with high efficiencies. Further inhibition of TGFβ alone is sufficient to anteriorize endoderm into Sox2+ foregut endoderm. These studies indicate that the anteriorization of the endoderm to foregut endoderm enhances the ultimate differentiation of Nkx2.1+ cells at later steps of the strategy. BMP4, FGF2 and WNT are each necessary for induction of the Nkx2.1+ immature lung progenitors. These early progenitors can mature into Nkx2.1+Sox2+ proximal progenitor cells and Nkx2.1+p63+ airway basal stem cells in vitro, and can differentiate into mature airway epithelium.

Example 1A: A Highly Efficient, Universally Applicable Protocol for Improving the Efficiency of Definitive Endoderm Production The endoderm is one of the three primary germ cell layers in the embryo. It forms the embryonic gut which in turn gives rise to the epithelia of the lungs and digestive organs. Therefore, the first essential step for directing human iPSC towards a lung lineage is to generate endoderm cells, preferably with high efficiency. For a variety of reasons, some cell lines do not generate definitive endoderm with high efficiency. For example, the current published protocol (Mou et al., 2012; RPMI+2% B27+100 ng/ml TGF-beta agonist Activin A+5 uM LY-294002 PI3K Inhibitor) is effective in several human iPSC and ESC lines with definitive endoderm efficiency higher than 90%. In some "difficult" or "resistant" cell lines, this same protocol generates definitive endoderm that varies between low efficiency (<30%) to medium efficiency (40-70%). The inventors screened multiple PI3K inhibitors including LY-294002, ZSTK474 (Zenyaku Kogyo Co.™), Wortmannin, PI828 (PIramed Ltd.™, Roche™), NVP-BKM120 (Novartis™), and PIK-75 (Drug Discovery Research, Astellas Pharma Inc.™), and determined that ZSTK474 is the most potent for definitive endoderm generation. In addition, the use of ZSTK474 permits the dose of the growth factor Activin A to be greatly decreased (e.g., from 100 ng/ml down to 20 ng/ml and in some cell lines down to 10 ng/ml Activin A). Therefore, this protocol is much more cost-effective than prior protocols. The PI3 kinase inhibitors noted above can also be obtained from commercial sources including, but not limited to, Promega™, Invivogen™, Sigma-Aldrich™, Cayman Chemicals™, Tocris™ and Cell Signaling Technologies™.

This protocol permits a remarkable 90% or greater, including 91%, 92%, 93%, 94%, 95%, 96%, 97%, and even as high as 98% or more, of human iPSC/ESC cells to be converted into definitive endoderm cell as determined by nuclear staining for the transcription factors Foxa2 and Sox17. Importantly, this protocol is very consistent from one experiment to another (i.e., reproducible). Furthermore, this protocol can be universally applied to multiple cell lines including several "difficult" cell lines that were determined to have low efficiency of definitive endoderm generation.

Protocol outline: Human ESC and iPSCs are grown with complete mTeSR1 medium on Geltrex™-coated plates (reduced growth factor (RGF) basement membrane extract (BME) purified from murine Engelbreth-Holm-Swarm tumor). The cells are fed every day and the differentiation is done at 65-80% confluence. For definitive endoderm differentiation, mTeSR1 was aspirated and the cells were rinsed with warm RPMI-1640 two times to remove the residual growth factors in mTeSR1. The medium was replaced with definitive endoderm differentiation medium (RPMI+2% B27+20 ng/ml Activin A+0.2-0.5 uM ZSTK474). The medium was changed daily over a total differentiation time of 4 days. The definitive endoderm efficiency was examined by FOXA2/SOX17 co-staining or by FACS analysis with cKit/CXCR4 and cKit/EpCAM combination.

Figure 13:
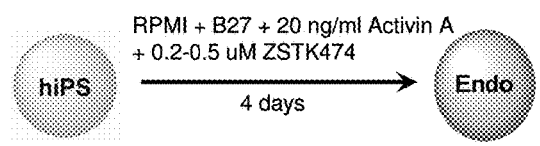
FIG. 13 is a schematic diagram depicting a variation of the protocol for producing definitive endoderm from human iPSC and ESC; the protocol permits production of definitive endoderm with high efficiency and consistency.

A schematic depicting the protocol for high efficiency definitive endoderm generation is shown herein in FIG. 13.

Figure 2A:
FIG. 2A and FIG. 2B show data indicating that anteriorization of endoderm to foregut endoderm promotes Nkx2.1+ cell differentiation.
Figure 2B:
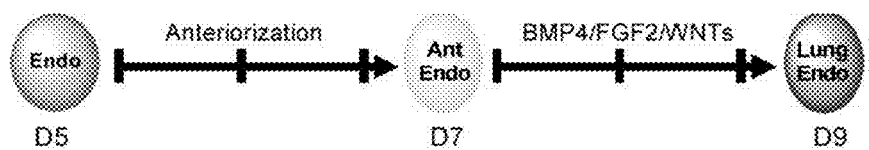
Figure 2B:
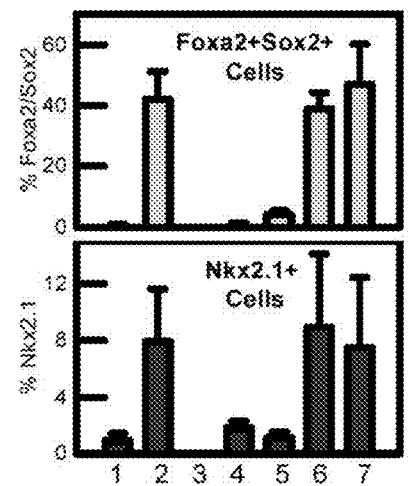
Figure 7:
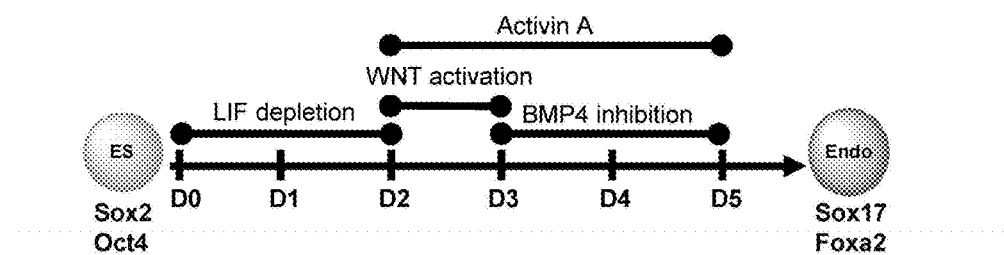
FIG. 7 is a schematic depicting a treatment strategy and time frame for generating definitive endoderm. Immunofluorescence of FOXA2 and SOX17 was performed at day 5 and indicates that >90% of cells were definitive endoderm generated from p2A mESCs and from V6.5 mESCs (data not shown).

Example 1B: Stage-Specific TGFβ Inhibition Regionalizes Naïve Endoderm to Anterior Foregut Endoderm and Facilitates the Differentiation of Nkx2.1+ Cells A recent report described a monolayer-based strategy using synergistic activation of Nodal and Wnt-β-catenin signaling as well as staged BMP4 inhibition to direct mouse ES cells towards an endoderm fate with high efficiency (Sherwood et al., 2011). This technology was adapted herein to generate definitive endoderm (DE) from mouse ES cells. FIG. 7 shows a schematic strategy and time frame to generate definitive endoderm. This protocol resulted in a remarkable 80%-90% of cells being converted into DE based on the dual expression of the endoderm transcription factors FoxA2 and Sox17 (data not shown). Next, it was asked if the newly generated DE cells have the competence to generate Nkx2.1+ cells. After exposing them for 2 days to serum-free medium containing BMP4, FGF2 and GSK3iXV (WNT agonist) (FIG. 2A), it was observed that less than 1% of the cells were Nkx2.1+ (data not shown). However, more than 60% of the cells were Cdx2+, indicating that the majority of the cells were specified to a hindgut fate (data not shown). Since the endoderm cells at this stage did not efficiently differentiate into Nkx2.1+ cells, it was tested whether an "anteriorization" step would facilitate lung fate specification. Snoeck and colleagues reported that Noggin (a BMP inhibitor) synergized with SB431542 (a TGFβ inhibitor) to suppress a posterior endoderm fate (Cdx2+) in favor of an anterior endoderm fate (Sox2+) (Green et al., 2011). Since the inventors had already incorporated BMP inhibition during DE generation (FIG. 7), the question whether continuous BMP inhibition is necessary for anteriorization or if TGFβ inhibition alone was sufficient for anterior patterning was explored. Endoderm was treated with combinations of Activin (a TGFβ agonist), A-83-01 (a TGFβ antagonist), BMP4, and Dorsomorphin (a BMP4 antagonist) for 2 days (FIG. 2B). The number of FoxA2+Sox2+ anterior endoderm cells was compared to the total number of FoxA2+ endoderm cells (FIG. 2B). The treated cells were further exposed to the BMP4/FGF2/WNT agonist cocktail for another 2 days to examine their competence to generate Nkx2.1+ cells (FIG. 2B). The results indicate that TGFβ inhibition itself was sufficient to increase FoxA2+Sox2+ anterior endoderm (40%-55%, compared to <0.1% in medium alone, FIG. 2B) and enhance the competence of endoderm cells to form Nkx2.1+ cells (~7%-13% as compared to <1% without regionalization, FIG. 2B). It was observed that continuous Activin treatment resulted in rare FoxA2+Sox2+ cells and few Nkx2.1+ cells (FIG. 2B), indicating that the optimal duration of Activin exposure plays a role in the efficiency of regionalization. It was also found that additional BMP4 inhibition was not required for the generation of FoxA2+Sox2+ cells and ultimately can result in slightly lower percentages of Nkx2.1+ cells (FIG. 2B). It was also observed that less neuroectodermal marker Tuj1 was present if BMP4 was present between days 5-7 (data not shown) in agreement with the finding that BMP4 suppresses neural commitment and promotes non-neural lineage differentiation from ESCs (Zhang et al., 2010). FGF and WNT signaling have been shown to maintain hindgut identity and actively repress foregut endoderm differentiation (Wells and Melton, 2000; Ameri et al., 2010). It was tested if their inhibition would enhance anteriorization together with a TGFβ inhibitor. Subsequent experiments revealed an FGF antagonist (PD173074) induced cell death, while a WNT antagonist (IWR-1) did not increase the FoxA2+Sox2+ population (data not shown).

Figure 8:
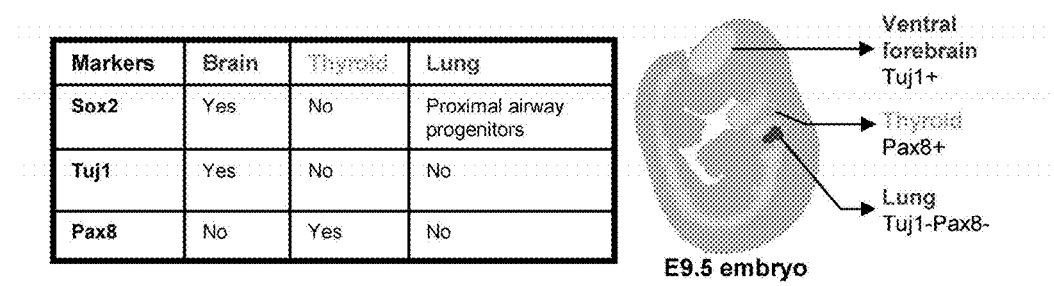
FIG. 8 is a table and a schematic that summarize immunofluorescence data for specific combinations of markers segregating Nkx2.1+ brain, thyroid and lung organ anlage in mouse embryos. Immunofluorescence imaging of Nkx2.1 and SOX2 was performed in ventral forebrain, thyroid, and lung at E8.75-E9 (data not shown). Immunofluorescence imaging was also performed for Nkx2.1, Tuj1, and Sox9 in ventral forebrain, as well as Nkx2.1, Pax8 and Sox9 in thyroid at E8.75-E9.

Example 2: Mouse ESC-Derived Nkx2.1+ Cells are Devoid of Neuronal and Thyroid Markers, are Proliferative, and Contain Distal Multipotent Lung Progenitors and Proximal Airway Progenitors Nkx2.1 is not a specific marker of the lung, and its expression is also found in the thyroid and ventral forebrain. Therefore, it was important to determine the identity of the Nkx2.1+ cells generated in the culture system used herein. Unfortunately, there are no reliable markers of the lung lineage at embryonic stage E9 that are not expressed in the brain or thyroid. Sp-C (Surfactant protein C), which is the most specific marker for lung epithelial progenitors, is not detected until E10-E11 (Wert et al., 1993). SOX9 and FOXP2 are indeed co-expressed with NKX2.1 in distal lung multipotent epithelial progenitor cells (data not shown) and are not found in brain or newly specified thyroid (data not shown), but their expression is not evident until after E11-E12. SOX2, on the other hand, is expressed in the E9 lung endoderm (data not shown) and later in airway epithelial progenitors (data not shown), but SOX2 can also be found in NKX2.1-expressing cells in ventral forebrain (FIG. 8 and data not shown). Thus, at the earliest stage of lung endoderm specification (E8.75-E9), none of these markers (SPC, SOX2, SOX9 and FOXP2) can be used to reliably and uniquely identify lung cells. In contrast, TUJ1 expression in Nkx2.1+ cells in ventral forebrain begins at E8.0 and continues to be present thereafter in ventral forebrain and not in thyroid or lung (FIG. 8 and data not shown), making Tuj1 expression a specific indicator of neuronal cell identity within the NKX2.1 domain. PAX8 expression is detected in the primordial thyroid at E8.75 at the time of thyroid specification (data not shown) but not in the lung or brain. Therefore, PAX8 can be used as a specific indicator of thyroid cell identity in the NKX2.1 domain (FIG. 8 and data not shown). In summary, the inventors conclude that at the early specification stage, Nkx2.1+/Tuj1−/Pax8− cells can be regarded as having a lung cell lineage. Accordingly, the ESC-derived Nkx2.1+ cells were interrogated for TUJ1 and PAX8 expression to exclude neuronal and thyroid identity (data not shown). As expected for any Nkx2.1+ cell in the embryo (thyroid, lung and ventral forebrain), all of the ex vivo differentiated Nkx2.1+ cells co-stained with Foxa2 (data not shown). A small subset of Tuj1+ cells were detected in the cultures, but these neuronal cells did not overlap with the Nkx2.1+ cells (data not shown). The inventors did not detect any Pax8+ cells in their culture (data not shown). Therefore, these data indicate that the Nkx2.1+ cells that are differentiated in vitro represent lung endoderm cells. These Nkx2.1+ cells are proliferative, with more than half expressing Ki67 (data not shown).

Data from immunofluorescence experiments indicate that ESC-derived Nkx2.1+ cells are devoid of neuronal and thyroid markers, are proliferative, and possess markers of proximal and distal lung endoderm. Immunofluorescence staining for FOXA2, TUJ1 and PAX8 was performed showing that Nkx2.1+ cells are positive for endodermal marker FOXA2, negative for neuroectodermal marker TUJ1, and negative for thyroid marker PAX8 (data not shown). Nkx2.1+ cells were proliferative as demonstrated by co-staining of Nkx2.1 with KI67 (data not shown). Immunofluorescence staining also indicated the presence of subpopulations of Nkx2.1+ cells that are positive for SOX2 (an airway progenitor marker) and FOXP2/SOX9 (multipotent lung progenitor marker) (data not shown).

In the mouse, Sox2 is rapidly downregulated in the foregut pre-lung endoderm just as Nkx2.1 expression initiates in this same pre-lung endoderm during the process of lung specification at E9 (data not shown). Thus, the very earliest of lung endoderm cells are Nkx2.1+ and Sox2-low cells. Soon thereafter, sustained high-level SOX2 expression is detected in the proximal airway epithelial progenitors of the future trachea, bronchus and bronchioles during the process of branching morphogenesis (data not shown). Airway progenitors are therefore Nkx2.1+Sox2+.

In contrast, SOX9 and FOXP2 are expressed exclusively in the distal tip multipotent lung progenitor cells (data not shown), making SOX9 and FOXP2 markers that uniquely identify a distinct population of multipotent embryonic lung progenitor cells within the NKX2.1 domain since they are not present in the proximal airway progenitors or the thyroid or brain as above. Therefore, the inventors checked if their ES cell-derived Nkx2.1+ cells at day 9 contained both proximal airway (Nkx2.1+Sox2+) and distal multipotent (Nkx2.1+Sox9+; or Nkx2.1+FoxP2+) progenitor cells. The Nkx2.1+ cells generated from 10 independent experiments were counted. The average proportion of airway progenitor cells (Nkx2.1+Sox2+) was 1.8%+/−0.8% out of the total Nkx2.1+ cells, while the proportions of distal multipotent progenitor cells, Nkx2.1+Sox9+ or Nkx2.1+FoxP2+, were 4.8%+/−2.5% and 6.6+/−3.1% out of total Nkx2.1+ cells, respectively. The remaining Nkx2.1+ cells (not thyroid or neural) are cells with minimal SOX2 expression and can reflect early pre-lung endoderm. Thus, the majority of Nkx2.1+ cells at day 9 likely represent an early lung endoderm that has not been specified to an airway progenitor or a distal tip multipotent lung progenitor population. Immunofluorescence indicates that the cells are enriched in Nkx2.1+Sox2+, Nkx2.1+Sox9+ and Nkx2.1+FoxP2+ cells (data not shown). In aggregate, these results imply that ESC-derived Nkx2.1+ cells at day 9 were immature, with most lacking proximal and distal progenitor cell markers, representing early lung endoderm cells. Although rare, the existence of Nkx2.1+Sox2+, Nkx2.1+Sox9+ and Nkx2.1+FoxP2+ cells indicated that the ES cell-derived Nkx2.1+ lung endoderm cells were differentiating into progenitor cells of the airway and multipotent lung progenitor cells that could later be differentiated into mature epithelial cells.

The expression of lung and other anterior cell fate lineage genes including FoxN1 (thymus), Pax8 (thyroid), and Pax9 and Tbx1 (pharyngeal pouch endoderm) was analyzed by real-time qPCR (FIG. S4A). As expected, the results showed that Sox2 was downregulated as pluripotent cells differentiated into definitive endoderm (DE). Later, Sox2 levels increased in accord with the expectation that anterior endoderm expresses Sox2. Nkx2.1, Sox9 and FoxP2 expression was minimal in ESCs, definitive endoderm and anteriorized endoderm, but was greatly increased (10-20 fold) after stimulation with the FGF2/WNT/BMP4 induction cocktail, consistent with previous results demonstrating these lung-specific marker combinations by antibody staining (data not shown). Similarly, FoxN1, Tbx1, Pax8, and Pax9 expression was low in ESCs, definitive endoderm and anteriorized endoderm. However, in growth factor-induced anterior foregut cells, a modest increase in Pax9 and Tbx1 expression was observed, whereas FoxN1 and Pax8 expression was still very minimal. Despite the increase in Pax9 and Tbx1 gene expression, the inventors did not detect any reproducible staining for these proteins by immunofluorescence (data not shown). All these results are consistent with the finding that a combination of FGF, BMP4, and WNT signaling predominantly drives the differentiation of lung-specific Nkx2.1+ progenitor cells from anterior endoderm.

Example 3A: BMP4, FGF and WNT Signaling are Each Necessary for NKX2.1 Induction In Vitro, Recapitulating Murine Lung Development It was tested if BMP4, FGF2, and WNT signaling are each required to specify lung endoderm from the anterior foregut in an in vitro mouse ESC differentiation system. To do this, anteriorized endoderm cells were exposed to combinations of BMP4, FGF2 and WNT agonists and antagonists (FIGS. 3A and B). It was found that BMP4 alone could induce NKX2.1 expression. In contrast, FGF2 or/and GSK3i without BMP4 was not sufficient for NKX2.1 induction, indicating that BMP4 signaling is required for lung specification (FIGS. 3B and C). Interestingly, in the presence of FGF and WNT antagonists, BMP4 could no longer induce Nkx2.1+ cells. This result implies an endogenous secretion of FGF and WNT ligands. It also suggests that FGF and WNT activation are needed for BMP4-dependent Nkx2.1 specification (FIGS. 3B and C). Despite presumptive endogenous FGF signaling, an added dose of FGF2 concentration upregulated Nkx2.1+ cells (FIGS. 3B and C). Compared to FGF2 signaling, exaggerated WNT activation was detrimental, with a decrease in Nkx2.1+ cells (FIGS. 4B and C) and an increase in hindgut Cdx2+ cells (data not shown).

Figure 4:
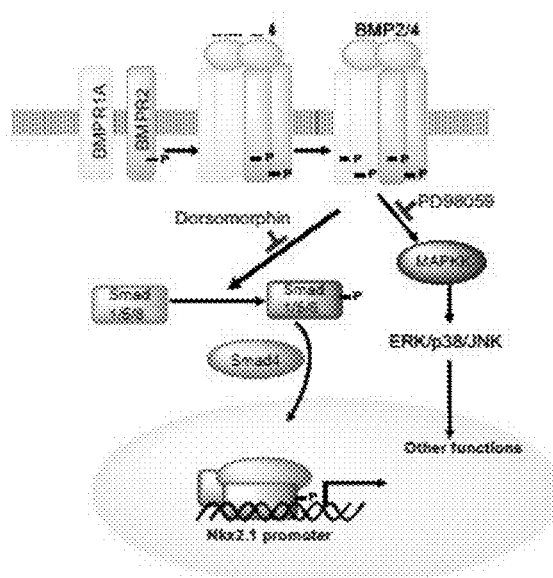
FIG. 4 shows that Smad-dependent BMP signaling is required for lung differentiation. NKX2.1 expression was induced with 20 ng/ml FGF2 and 5 nM GSK3iXV only (control) or with additional BMP4 (20 ng/ml), BMP2 (20 ng/ml), BMP7 (20 ng/ml), BMP4 (20 ng/ml)+10 µM Dorsomorphin, or BMP4 (20 ng/ml)+1 µM PD98059 (data not shown).

BMP2, 4 and 7 are by far the most studied members of the BMP family. Both BMP2 and BMP4 signal through the type I receptor (ALK3), whereas BMP7 binds to a separate type I receptor (ALK2) (reviewed by von Bubnoff and Cho, 2001; Chen et al., 2004; Sieber et al., 2009; Miyazono et al., 2010). The effects of BMP2 and BMP7 were compared to BMP4 on induction of Nkx2.1+ cells from the anterior endoderm. The results showed that BMP2 was less efficient than BMP4 at inducing Nkx2.1+ cells, while BMP7 (10 ng/ml) had no effect (data not shown). Even with an increased concentration (>100 ng/ml), BMP7 still failed to generate Nkx2.1+ cells (data not shown). This indicates that BMP7 signaling via the ALK2 receptor is not required for NKX2.1 induction. In canonical BMP2/4 signaling, BMP2/4 binds to BMP receptor I/II complex, leading to phosphorylation of Smad1/5/8, followed by formation of heteromeric complexes with Smad4. These complexes translocate to the nucleus and activate expression of target genes (von Bubnoff and Cho, 2001; Chen et al., 2004; Sieber et al., 2009; Miyazono et al., 2010). Besides Smad1/5/8-mediated transcription, BMP-induced receptor complexes can activate the mitogen-activated protein kinase (MAPK) pathway via ERK, JNK or p38 (Kozawa et al., 2002). Using Dorsomorphin (a pSmad1/5/8 inhibitor) and PD98059 (a MAPKK/ERK inhibitor), it was observed that Dorsomorphin completely abrogated generation of Nkx2.1+ cells, while PD98059 only partially decreased the Nkx2.1+ cell proportion (data not shown). Significant cell death was observed in the presence of PD98059, so the possibility that the decrease in Nkx2.1+ cells was due to apoptosis could not be excluded. In addition, Smad and MAPK-mediated pathways can be integrated (Aubin et al., 2004), and the decrease in Nkx2.1+ cells in the presence of PD98059 might also be due to a downregulation of Smad-dependent signaling. Overall, it was concluded that Smad-dependent BMP2/4 signaling cascade is necessary for NKX2.1 specification from foregut cells (FIG. 4).

Example 3B: Nkx2.1+ Differentiation to Generate Lung Progenitors

A high throughput chemical screen was used to identify compounds that can facilitate Nkx2.1+ lung progenitors and also identifies novel signaling pathways controlling human lung specification.

Figure 14A:
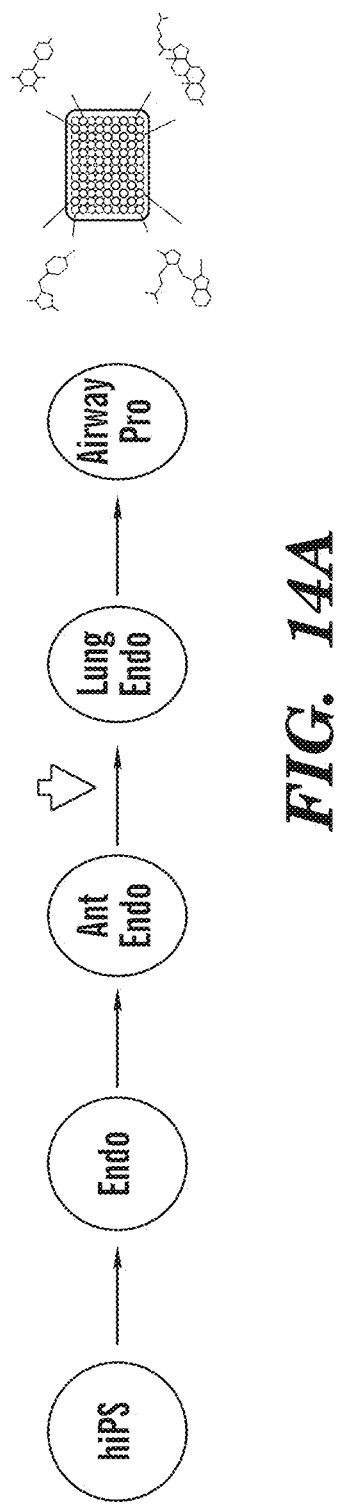

In order to increase the efficiency of Nkx2.1+ lung progenitor production, the inventors performed an unbiased high throughput chemical screening on a kinase pathway inhibitor library and an NIH clinical drug library to identify small molecule compounds and FDA-approved clinical drugs that can facilitate NKX2.1-positive lung progenitor differentiation. The platform for chemical screening is illustrated in FIG. 14A. The screening was performed at the step of conversion of Foxa2+Sox2+ anterior endoderm to Nkx2.1+ lung endoderm.

At least five molecules were identified from the Kinase Compound Set (240 compounds) and at least 6 drugs were identified from the NIH Clinical Collection (400 compounds) that produced statistically significant (more than 3 fold) increases in the percentage of Nkx2.1+ cells (FIG. 14B). These Nkx2.1+ cells have been further stained in separate experiments to exclude the expression of neuronal lineage marker Tuj1 and thyroid lineage marker Pax8. In addition, all positive candidates identified in the primary screen have been assessed for drug duration and dose effects to increase the formation of lung progenitors, and they have been evaluated for other effects including inducing cytotoxicity, and cellular proliferation by Ki67 staining. Since these compounds are annotated, the inventors found that there are multiple positive hits targeting the same pathway such as PI3K and PKC-related signaling pathways. Without wishing to be bound by theory, these data indicate that these biological pathways are actively involved in human lung organogenesis. It was also determined that BMP4 is dispensable for human lung progenitor differentiation from iPSCs, indicating a species difference in lung development in human and mouse. It was determined that inhibition of BMP4 generates lung progenitors with a high NKX2.1 expression level, while addition of BMP4 decreases NKX2.1 expression without affecting the total NKX2.1+ lung progenitor cell number.

In addition to positive hits, some compounds were found to decrease or even block NKX2.1+ cell production. Several of these negative compounds are MEK1/2 antagonists. Without wishing to be bound by theory, these data indicate that MEK1/2-related signaling pathways play important roles in human lung organogenesis and lung progenitor differentiation from iPSCs. For example, endoderm-specific deletion of MEK1/2 results in lung agenesis in mice (unpublished data). In the in vitro differentiation systems, the inventors found activation of MEK1/2 (such as by phorbol 12-myristate 13-acetate or PMA, and other MEK1/2 agonists) stimulates NKX2.1+ cell production.

Figure 12:
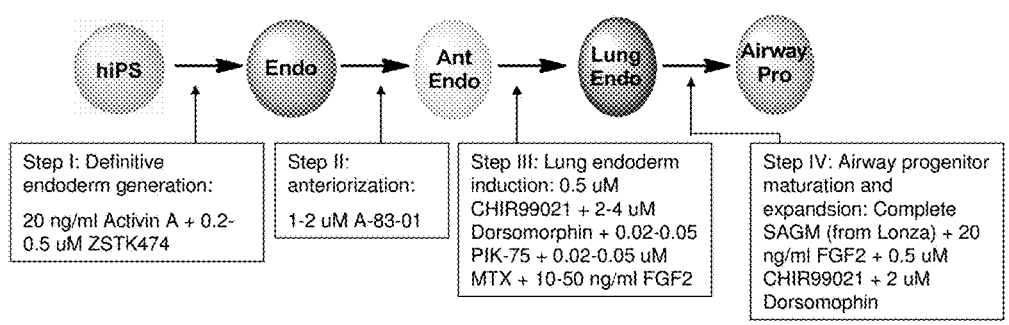
FIG. 12 is a schematic diagram depicting an exemplary step-wise airway progenitor differentiation protocol from iPSC to airway progenitors.

After studying the additive and synergistic effects of the positive hits, a robust and economically efficient new protocol was devised for the generation of a highly enriched population of Nkx2.1+ lung progenitors (up to 85%-90%) from multiple iPS cell lines in xeno-free conditions in order to keep the cells suitable for future clinical applications. This exemplary differentiation medium contains one Wnt agonist (e.g., 0.5 uM CHIR9902), one PI3 kinase inhibitor (e.g., 0.02-0.05 uM PIK-75), one clinically used drug (e.g., 0.02-0.05 uM methotrexate), one BMP antagonist (e.g., 2-4 uM Dorsomorphin) and a single growth factor (e.g., 10-50 ng/ml FGF2). FIG. 12 is the summary of the newly developed step-wise airway progenitor differentiation protocol from iPSC to airway progenitors. Many other protocols can be generated by one of skill in the art from this basic protocol (RPMI+2% B27+10-50 ng/ml FGF2+0.5 uM CHIR9902+ 2-4 uM Dorsomorphin) together with the compounds listed in FIG. 14.

Based on the current cost of media etc., the inventors calculate the cost of differentiation medium from iPSC to lung progenitors (step I to step III) is only 10% of the original one reported in Mou et al., 2012, but the protocol has enhanced efficiency of NKX2.1+ cell production.

In addition, the inventors have demonstrated that this approach is effective in multiple human iPS cells and ESC cells. Step IV allows the maturation of immature lung progenitors into the NKX2.1+SOX2+p63+CK5+ airway stem cells and can also be used to expand such populations to increased passages and/or to increase the cell quantity for e.g., functional assays, disease modeling and drug screening.

Figure 5A:
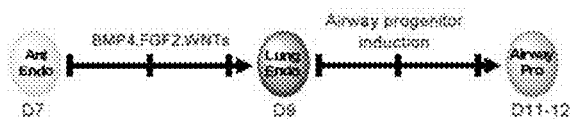
FIG. 5A and FIG. 5B show the generation of embryonic airway progenitors from multipotent lung endoderm cells.
Figure 5B:
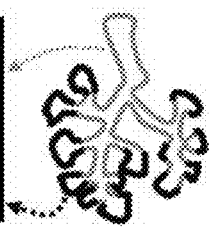

Example 4: The Combination of BMP7 and FGF7 Signaling, as Well as WNT and MAPKK/ERK Inhibition, Generates Proximal Airway Progenitors As demonstrated herein above, most ESC-derived Nkx2.1+ cells at day 9 were immature lung endoderm cells. Therefore, these cells were differentiated in order to produce more mature Nkx2.1+Sox2+ embryonic airway progenitors. The inventors selectively applied signaling factors to generate airway stalk progenitors from immature lung Nkx2.1+ cells (FIGS. 5A and B). The cells were switched at day 9 to a "proximal induction" medium prepared with RA-supplemented B27, BMP7, FGF7, IWR-1 (WNT antagonist), and Noggin (data not shown). After 2-3 days, an increase in Nkx2.1+Sox2+ airway progenitor cells was observed. The proportion was ~10% of the total number of Nkx2.1+ cells, as compared to 1%-2% before treatment. In separate experiments in which individual growth factors were removed, it was found that WNT antagonism had the most pronounced effect on Nkx2.1+Sox2+ cell production. Addition of Dorsomorphin (BMP antagonist) to replace Noggin at this stage had little effect on the number of Nkx2.1+Sox2+ cells. Interestingly, the small molecule PD98059 (a MAPKK/ERK inhibitor) enhanced generation of Nkx2.1+Sox2+ airway progenitor cells to up to 18% of the total number of Nkx2.1+ cells (data not shown). These data indicate that airway progenitors are formed after inhibition of a MAPKK/ERK-related pathway. Most notably, the inventors started to detect a small fraction of Nkx2.1+p63+ cells (about 1%-4% of the total number of Nkx2.1+ cells) at day 11-12 (FIG. 6D). An increase in the duration of culture in the "proximal induction" medium from 2 to 5 or more days resulted in higher proportions of Nkx2.1+Sox2+ and Nkx2.1+p63+ cells (data not shown). Although the production of Nkx2.1+Sox2+ and Nkx2.1+p63+ cells still needs to be optimized, these results demonstrate that ESC-derived Nkx2.1+ cells can be differentiated into proximal airway progenitors and conducting airway basal cells. An approach for isolating specific subpopulations of these cells, e.g., Nkx2.1+, Sox2+ cells or Nkx2.1+, Sox9+ cells or Nkx2.1+, p63+ cells is to transfect the cells with a reporter gene construct, e.g., a GFP reporter construct driven by Sox2, Sox9 or p63 promoter. Expression of GFP under these circumstances will identify the cell as permissive for expression of the subject factor. It is contemplated that these studies can be performed on cells at limiting dilution. For example, a population of anterior foregut endoderm cells can be induced to differentiate to Nkx2.1+, Tuj1−, Pax8−, multipotent lung progenitors as described herein, followed by treatment to differentiate to airway progenitors as also described. After appropriate time under inducing conditions, the population can be subjected to limiting dilution and plated at one cell per well in a microtiter dish. The isolated cells can be permitted to clonally expand in culture, and a portion of expanded cells can be tested, e.g., via immunofluorescence, for the expression or co-expression of the derived airway progenitor markers, e.g., Nkx2.1, Sox2, Sox9, p63 or even more distal differentiation markers, e.g., CCSP, FoxJ1, etc. In this manner isolated populations of the various progenitors can be prepared.

One of skill in the art will recognize that alternate methods of producing an isolated population of cells can also be employed with the methods described herein. In some embodiments, a chemical or combination of chemicals can be used to enhance the efficiency of cell differentiation in culture to increase the numbers of a desired cell type. Such enhanced efficiency of cell differentiation permits the production of an isolated population of the desired human lung progenitor cell type by e.g., positive selection for a desired cell phenotype or selective killing of a non-desired cell phenotype. Alternatively, the cells can be genetically modified such that they express GFP upon differentiation to a desired human lung cell progenitor phenotype, permitting the use of e.g., FACS sorting to isolate cells of a defined phenotype. In addition, one of skill in the art can generate antibodies (e.g., monoclonal antibodies) against a particular cell surface marker or combination of markers. Such an antibody or combination of antibodies can be used to purify a desired cell type from a population of cells.

Example 5: ESC-Derived Nkx2.1+ Cell Populations can Differentiate into Mature Airway Epithelium when Transplanted In Vivo Nkx2.1+ lung progenitor cells derived from pluripotent stem cells should possess the capacity to generate functional respiratory epithelium to be useful. Therefore, mouse ESC-derived Nkx2.1+ progenitors were tested for their capacity to form mature respiratory epithelium by subcutaneous engraftment (data not shown). The assay evaluated the ability of Nkx2.1+ cells to differentiate within a mixed cell population. 20,000-50,000 cells were suspended in 50% Matrigel and injected under the skin of immunodeficient mice. 20-30 days after injection, engrafted tissues were excised for examination. Differentiation of airway epithelium from mouse ESC-derived lung endoderm was observed upon subcutaneous engraftment. Immunofluorescence staining indicates that some Nkx2.1+ cells are positive for SOX2 (data not shown). Immunofluorescence staining further indicated differentiation of ESC-derived Nkx2.1+ cells into p63+ airway basal stem cells, CC10+ Clara cells, FoxJ1+ ciliated cells and Muc5ac+ goblet cells (data not shown).

It was observed that many epithelial spheres formed within grafts and that some of these spheres contained Nkx2.1-expressing cells. In some Nkx2.1+ spheres, markers of mature airway epithelial cells (data not shown) were detected, including Sox2+ proximal airway epithelial cells (data not shown), p63+ basal stem cells, CC10+ Clara cells, FoxJ1+ ciliated cells, and Muc5ac+ mucin-secreting cells (data not shown).

Triple immunofluorescence staining with confocal imaging demonstrated spheres that contain more than one marker of mature airway epithelium. Such mature airway epithelial markers have never been detected in ESC-derived teratomas. Previously published basal stem cell differentiation using a three-dimensional sphere-forming assay produced ciliated and basal cells but not Clara cells (Rock et al., 2009). The inventors did not detect any type I and type II pneumocyte markers such as PRO-SPC, PRP-SPA and AQUAPORIN5 despite having distal lung multipotent cells (Nkx2.1+Sox9+ and Nkx2.1+FoxP2+) in the initial cell mixture. Overall, it was concluded that ESC-derived Nkx2.1+ cell-containing populations are capable of airway epithelial cell differentiation.

Figure 6:
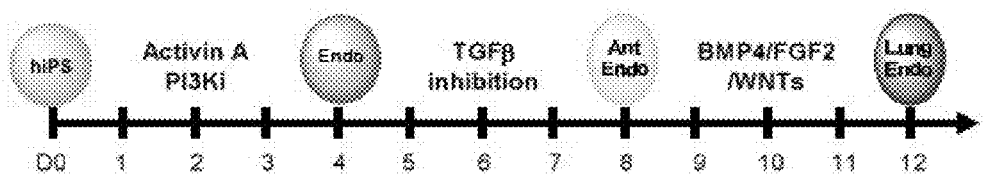
FIG. 6 is a schematic depicting an exemplary strategy and time line to generate Nkx2.1+ lung multipotent progenitors from human iPSCs. Data from the experiment indicate a step-wise differentiation of Nkx2.1+ lung progenitors from human iPSCs. A high yield of definitive endoderm from CF1 RiPS cells was obtained after treatment for 4 days in RPMI-1640 media in the presence of 2% B27 supplement, Activin A (100 ng/ml) and 5 µM PI3 Kinase inhibitor LY294002 with more than 90% of cells co-expressing transcription factors SOX17 and FOXA2 (data not shown). Anteriorization of endoderm into foregut endoderm cells was observed by detecting SOX2 expression in Foxa2+ cells derived from CF1 RiPS cells after 4 days of treatment with 500 nM A-83-01 (TGFβ antagonist) and 100 ng/ml Noggin (BMP4 antagonist) (data not shown). NKX2.1 staining was performed after anteriorization to foregut cells at D8 with serum-free medium containing 20 ng/ml BMP4, 20 ng/ml FGF2 and 5 nM GSK3iXV for 4 days (data not shown). Immunofluorescence showed co-staining of Nkx2.1-positive cells with SOX2, SOX9, TUJ1 and PAX8, thereby demonstrating a lack of thyroid and neuronal differentiation and the presence of multipotent distal tip progenitors and Nkx2.1+/Sox2+ airway progenitors (data not shown). In addition, confocal images following immunofluorescence staining indicates some Nkx2.1+ sphere contain basal cells positive for p63 (data not shown).

Example 6: An Efficient and Reproducible Step-Wise Approach to Generate NKX2.1+ Lung Cells from Human Cystic Fibrosis iPS Cells Next, it was examined whether a similar step-wise differentiation approach could be used to generate lung airway progenitors from Cystic Fibrosis (CF) disease-specific human iPSCs (FIG. 6). All differentiation steps were performed in xeno-free conditions. Furthermore, two of the CF iPSC lines were generated using modified RNAs (RiPS) rather than virally encoded reprogramming factors (Warren et al., 2010) and thus were genetically unmodified, another advantage for possible future clinical use. CF iPSCs were maintained on Geltrex-coated plates in complete mTeSR1 medium. High yields of definitive endoderm (DE) were obtained after treatment for 3-4 days in RPMI-1640 media in the presence of Activin (100 ng/ml) and PI3 kinase inhibitor LY294002 (5 μM). More than 85%-90% of cells co-expressed the transcription factors SOX17 and FOXA2 at day 4, demonstrating very efficient production of DE from a RiPS cell line that is compound heterozygous for CFTR mutant alleles Δ508 and G551D (data not shown). This protocol was also successfully applied to other human pluripotent cells including three Cystic Fibrosis iPSC lines homozygous for the Δ508 allele, a wild-type human BJ RiPS cell line (Warren et al., 2010), and the HUES-3 and HUES-9 human ESC lines (data not shown).

By using anteriorization conditions similar to Green et al., the induction of SOX2 expression in DE cells was obtained with efficiencies of up to 50%-60% after 4 days of treatment with A-83-01 (a TGFβ antagonist; data not shown). It was found that Noggin (a BMP4 antagonist) was actually not necessary for this anteriorization. Similar combinations of growth factors and agonists (BMP4, FGF2 and GSK3iXV) identified in the studies on mouse ES cells can be used to generate NKX2.1+ cells with efficiencies of 10%-30% (data not shown). These NKX2.1+ cells were negative for TUJ1 and PAX8 (data not shown), demonstrating that they were not of neural or thyroid identity. In addition, subpopulations of these NKX2.1+ cells were also positive for SOX2 and SOX9 (data not shown). These markers suggest the presence of both committed airway progenitors (NKX2.1+SOX2+ cells) and multipotent embryonic lung progenitors (NKX2.1+SOX9+ cells).

Figure 9A:
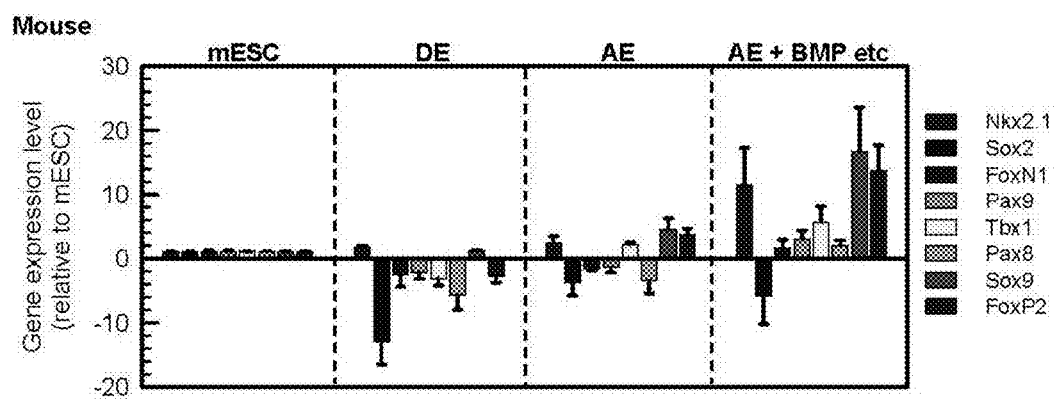
FIG. 9A and FIG. 9B are graphs depicting a gene expression analysis of ESC-derived anterior endoderm fates. Quantitative expression of Nkx2.1, Sox2, FoxN1, Pax9, Tbx1, Pax8, Sox9 and FoxP2 mRNA in mouse ESC or human iPSCs, corresponding definitive endoderm (DE) and anterior endoderm (AE) and AE after treatment with Nkx2.1-inductive growth factor cocktail. n=3 biological triplicate replicates, the expression level is normalized to the level of ESCs or iPSCs.
Figure 9B:
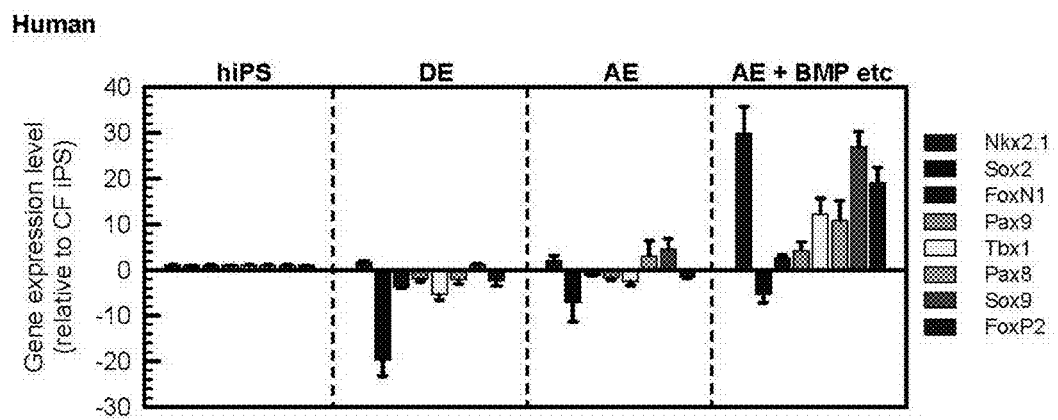
Figure 10:
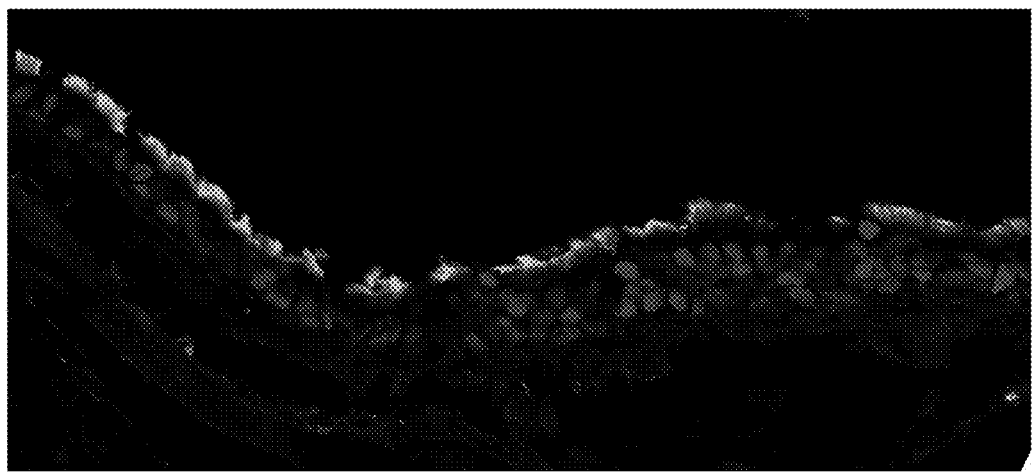
FIG. 10 is a micrograph depicting the presence of functional cilia on the surface of an airway cell differentiated from a human lung progenitor as described herein. The cilia were observed to beat in coordinated waves, indicating that the airway cell is functional.

The expression of various anterior cell fate genes were quantified by qPCR (FIG. 9) and similar gene expression patterns were observed as compared to the expression patterns observed during mouse ES cell differentiation. SOX2 was downregulated after differentiation into definitive endoderm and then increased as expected after anteriorization. A dramatic upregulation of NKX2.1, SOX9, and FOXP2 expression (20-30 fold) in anteriorized endoderm cells was observed after FGF2/BMP4/WNT induction. The expression of other anterior cell fate genes including PAX8 (thyroid endoderm), PAX9 (pharyngeal endoderm), and TBX1 (pharyngeal endoderm anterior to lung/esophagus) was only modestly upregulated without any expression of FOXN1 (thymus endoderm). In aggregate, the differentiation spectrum of the endoderm was remarkably similar in the mouse and human platforms.

Finally, human RiPS cell-derived NKX2.1+ mixed cell populations were subcutaneously engrafted (data not shown). Many spheres formed in engrafted tissues after 30 days under the skin of immunodeficient recipient mice. In NKX2.1+ spheres, some of the NKX2.1+ cells co-expressed p63, indicating that these NKX2.1+ cells had matured into airway basal stem cells (data not shown).

Example 7: Summary

Herein is reported a step-wise strategy to differentiate pluripotent stem cells into lung multipotent progenitors (Nkx2.1+Sox9+ and Nkx2.1+FoxP2+) and airway progenitors (Nkx2.1+Sox2+). The inventors show that mimicking the regionalization of the embryonic foregut enhanced the subsequent differentiation of Nkx2.1+ lung cells. This lends credence to the notion that the optimization of each discrete step during embryogenesis will result in an improvement in the efficiency of differentiation at each subsequent step. Some of these Nkx2.1+ lung endoderm cells were ultimately differentiated into multipotent embryonic lung progenitor cells and airway progenitor cells, a finding that has not been previously reported. Additionally, the committed Nkx2.1+ lung progenitor cells produced specific mature cell markers of the airway epithelium when engrafted. The inventors then adapted their strategy to produce disease-specific lung progenitor cells from human Cystic Fibrosis iPS cells and other human pluripotent stem cell lines, thus creating a new platform for dissecting human lung disease.

Additionally, ESC systems can be used as a discovery tool to investigate steps in lung development. It was also demonstrated that FGF signaling in addition to BMP and WNT signaling is required in the current culture system for NKX2.1 induction, an observation that has proven difficult to define in murine genetic systems due to the presence of multiple FGFs in the vicinity of the foregut lung anlage. Mechanistic dissection of the BMP4 signaling effect also revealed a novel observation that BMP4 signaling occurs through a Smad-dependent pathway and that pharmacologic Smad modulation enhances Nkx2.1+ lung cell differentiation. The inventors have also shown that the carefully timed staged antagonism or agonism of the same pathway is essential to drive optimal differentiation. The early addition of WNT signals that are later necessary for Nkx2.1+ lung cell induction at the endoderm stage, for example, regionalizes endoderm to a hindgut intestinal epithelium that is refractory to forming Nkx2.1+ cells (Spence et al., 2011; Cao et al., 2011; Sherwood et al., 2011). Thus not only combinations of signaling cascades but also their precise timing is essential to recapitulate in vivo differentiation. Accordingly the system described herein is a useful adjunctive platform for defining mechanisms of lung cell differentiation that were not previously described using mouse developmental genetics.

This work was the first to demonstrate the Nkx2.1+Sox2+ proximal airway progenitors as well as the Nkx2.1+p63+ double-positive airway stem cells that are derived from both human and mouse pluripotent stem cells. Zaret and colleagues have suggested that the anterior gut contains an epigenetic pattern that regulates the ability of gut endoderm to differentiate into a particular tissue despite the presence of the correct growth factors (Zaret et al., 2008). It will be of interest to investigate whether an endodermal pre-pattern based on epigenetic factors could be modulated to enhance lung progenitor cell specification.

The inventors have successfully differentiated the mixed cell populations into airway epithelium by engrafting them into an immunodeficient mouse subcutaneously. Indeed, it is possible that other cells within this mixed population are necessary to induce airway progenitors to form the respiratory spheres.

In summary, provided herein is a robust and generally applicable protocol for DE generation, endoderm anteriorization to foregut, and derivation of the earliest lung Nkx2.1+ endoderm as well as multipotent Nkx2.1+Sox9+ lung progenitors, Nkx2.1+Sox2+ embryonic airway progenitors, and Nkx2.1+p63+ airway stem cells from mouse ESCs. The strategy was adapted to generate disease-specific lung progenitor cells from human Cystic Fibrosis iPSCs, thus establishing a new platform for dissecting human lung disease. This allows for disease modeling, drug screening, genetic rescue of the mutant CFTR gene (using homologous recombination, zinc finger nucleases, or TAL effector nucleases) and autologous transplantation. Furthermore, this strategy can in principle be applied to any human genetically influenced lung disorder. Given the wealth of emerging data in the genetics of common human lung diseases, this platform will also serve as a springboard to test the biological significance of candidate genes in airway epithelium. Finally, the ability to generate a large number of lung epithelial cells can enable biochemical and proteomic experiments not previously possible due to the limited supply of human lung epithelial cells.

Example 8: Experimental Procedures

Mice and Human Cell Lines:

NOD-SCID IL2Rgamma null (NOD/SCIDIl2rg−/−) immunodeficient mice were purchased from Jackson Laboratory. Animal procedures were performed in accordance with Massachusetts General Hospital (MGH) and national guidelines and regulations and approved by the Institutional Animal Care and Use Committee (IACUC) for MGH. The use of human Cystic Fibrosis induced-pluripotent cell lines and embryonic cell lines (Hues-3 and Hues-9) were reviewed and approved by the Embryonic Stem Cell Research Oversight committee (ESCRO) and IRB at MGH.

Mouse Endoderm Anteriorization and Nkx2.1 Cell Differentiation:

Mouse definitive endoderm was generated as described herein. To anteriorize endoderm, on and after day 5, the cells were split and re-seeded on to the plates pre-coated with 804G-conditioned medium and fed with D0 medium+0.5-1 µM A8301 (CalBiochem, 616454) for 2 days. Then the media was rinsed with D0 medium 2 times and switched to D0 medium supplemented with 50 ng/ml BMP4, 100 ng/ml FGF2 (GIBCO, PHG0026), and 5-10 nM GSK3iXV for another 2-3 days. To generate Nkx2.1+Sox2+ proximal progenitor cells, the cells were rinsed with D0 medium 2 times and switched to D0 medium containing RA-supplemented B27, 50 ng/ml BMP7, 50 ng/ml FGF7, 100 nM IWR-1, and 1-2 µM PD98059 for 2 days or longer times.

Human iPSC Culture and Differentiation:

Human iPSCs were maintained on Geltrex-coated plates in complete mTeSR1 medium (Stemcell). High yields of definitive endoderm progenitors were obtained after treatment for 3-4 days in RPMI-1640 media in the presence of 2% B27 supplement minus vitamin A (GIBCO, 12587-010), Activin A (Peprotech, 100 ng/ml) and PI3 Kinase inhibitor LY294002 (5 µM). To generate foregut endoderm cells, definitive endoderm was treated for 4 days with RPMI-1640 medium containing 2% B27, 500 nM A-83-01 (TGFβ antagonist) with or without Noggin (BMP4 antagonist, 100 ng/ml) or Dorsomorphin (2-5 µM). After that, the cells were exposed for 4 days or longer time to RPMI-1640 medium containing 2% B27, 50 ng/ml BMP4, 100 ng/ml FGF2 and 5 nM GSK3iXV for Nkx2.1 induction from endoderm cells.

Immunofluorescence:

At each differentiation step, the cells were fixed with fresh paraformaldehyde (4%) for 15 min at room temperature, rinsed in PBS, washed with PBS+0.2% Triton X-100 and incubated with the primary antibodies at 4° C. overnight (>16 hrs) diluted in PBS+1% BSA. Following incubation, the cells were rinsed 4 times PBS+0.2% Triton X-100, and incubated with secondary antibodies at room temperature for 2 hours. The images were visualized using an Olympus IX71 inverted fluorescence microscope or a Nikon A1 Confocal Laser microscope. The primary antibodies used are summarized in the following table:

TABLE 1

Primary Antibody List

| Antibody | Source |
| --- | --- |
| SOX2 | R&D, goat polyclonal, AF2018 |
| SOX9 | R&D, goat polyclonal, AF3075 |
| SOX17 | R&D, goat polyclonal, AF1924 |
| FOXP2 | R&D, goat polyclonal, AF5647 |
| FOXA2 | Santa Cruz technology, goat polyclonal, sc-655 |
| TUJ1 | Sigma, mouse monoclonal, T8578 |

TABLE 1-continued

Primary Antibody List

| Antibody | Source |
| --- | --- |
| PAX6 | Developmental Studies Hybridoma Bank, mouse monoclonal |
| PAX8 | Abcam, mouse monoclonal, ab53490 |
| NKX2.1 | Abcam, rabbit polyclonal, ab76013 |
| P63 | Santa Cruz Technology, mouse monoclonal, sc-56188 |
| CDX2 | BioGenex, mouse monoclonal, CDX2-88 |
| KI67 | BD pharmaceutical, mouse monoclonal, 556003 |
| CCSP | From Dr. Barry Stripp, Duke University Medical Center, goat polyclonal |
| FOXJ1 | eBioscience, mouse monoclonal, 14-9965-82 |
| MUC5AC | Thermo Scientific, mouse monoclonal, 2013-05 |

The secondary antibodies were purchased from Invitrogen (AlexaFluor-549 and AlexaFluor-488). The quantification was performed by counting at least 5 random fields at 20× magnification and calculating the average and standard deviation.

Embryo Harvest, Section Cutting and Staining:

The embryos or lungs at desired embryonic stages were dissected out and fixed at 4° C. for 6 hours or overnight with fresh 4% PFA. Then tissues were rinsed with PBS for 3 min (5 min per time) and incubated in 30% sucrose in PBS at 4° C. overnight. The tissues were soaked in OCT for 1 hour and then frozen in OCT for cryosectioning at 7 µm thickness. The slides were stained with the primary and secondary antibodies as described above.

Differentiation of Mouse ESC and Human iPS-Derived Nkx2.1+ Lung Progenitors after Subcutaneous Engraftment:

$2-5 \times 10^5$ cells were suspended in 200 µl 1:1 mixture of Growth Factor Reduced Matrigel (BD Biosciences, 354230) Advanced DMEM and injected subcutaneously into NOD-SCID IL2Rgamma null mice. The tissues were harvested and examined after 20-30 days, fixed overnight in cold 4% paraformaldehyde, rinsed 2 times with PBS, soaked in 30% sucrose for 2-3 hours and then embedded in OCT, and sectioned at 7 µm. The slides were examined for airway epithelial cells based on NKX2.1 expression. The differentiation of ESC-derived Nkx2.1+ cells into basal stem cells was based on expression of P63 and CK5, goblets cells based on expression of MUC5AC, Clara cells based on expression of CCSP, and ciliated cells based on the expression of FOXJ1.

Exemplary Media for Differentiation

Step I: From Human ES Cells and iPS Cells to Definitive Endoderm

An exemplary RPMI-1640 based differentiation medium can contain 2% B-27 (retinoic acid free), 0.1% Albumax II, 1× Glutamax, 1× non-essential amino acids (NEAA), 5 uM LY294002 (PI3K inhibitor), and 100 ng/ml Activin A. In some embodiments, 5 µM LY294002 and/or 100 ng/mL Activin A are used. However, LY294002 can be used within a range of e.g., 2-10 uM and Activin A can be used within a range of e.g., 75-150 ng/ml. In some embodiments, the length of time for treatment for Step I is 4-5 days.

Step II: From Definitive Endoderm to Anterior Foregut Endoderm

An RPMI-1640 based differentiation medium for Step II can contain 2% B-27 (retinoic acid free), 0.1% Albumax II, 1× Glutamax, 1× non-essential amino acids (NEAA), 0.5-2 uM TGFb antagonist A8301, 100-500 nM WNT antagonist IWR-1. In some embodiments, the length of time for treatment is 2-4 days.

Step III: From Anterior Foregut Cells to Nkx2.1+ Cells

An exemplary RPMI-1640 based differentiation medium for Step III can contain 2% B-27 (supplement with RA), 0.1% Albumax II, 1× Glutamax, 1× non-essential amino acids (NEAA), 20-200 nM BMP4, 20-200 ng/ml FGF2, 5-50 nM GSK3iXV (or 100-1000 nM CHIR-99021 to replace GSK3iXV). In some embodiments, the length of time for treatment is about 4-6 days.

Step IV: from Nkx2.1 Early Lung Endoderm Cells to Nkx2.1+Sox2+ Proximal Airway and Nkx2.1+p63+ Airway Basal Stem Cells An exemplary RPMI-1640 based medium can contain 2% B-27 (supplement with RA), 0.1% Albumax II, 1× Glutamax, 1× non-essential amino acids (NEAA), 20-100 ng/ml BMP7, 20-100 ng/ml FGF7, 50-100 ng/ml IWR-1 (WNT antagonist) and 1-2 uM PD98059 (MAPKK/ERK antagonist). In some embodiments, the length of time for treatment is about 4-6 days.

A second exemplary medium for differentiation is depicted herein in FIG. 12.

REFERENCES CITED IN EXAMPLES

Ameri, J., Stahlberg, A., Pedersen, J., Johansson, J. K., Johannesson, M. M., Artner, I., and Semb, H. FGF2 specifies hESC-derived definitive endoderm into foregut/midgut cell lineages in a concentration-dependent manner. Stem cells (Dayton, Ohio) 28, 45-56.

Aubin, J., Davy, A., and Soriano, P. (2004). In vivo convergence of BMP and MAPK signaling pathways: impact of differential Smad1 phosphorylation on development and homeostasis. Genes & development 18, 1482-1494.

Bellusci, S., Henderson, R., Winnier, G., Oikawa, T., and Hogan, B. L. (1996). Evidence from normal expression and targeted misexpression that bone morphogenetic protein (Bmp-4) plays a role in mouse embryonic lung morphogenesis. Development (Cambridge, England) 122, 1693-1702.

Cao, L., Gibson, J. D., Miyamoto, S., Sail, V., Verma, R., Rosenberg, D. W., Nelson, C. E., and Giardina, C. Intestinal lineage commitment of embryonic stem cells. Differentiation; research in biological diversity 81, 1-10.

Chen, D., Zhao, M., and Mundy, G. R. (2004). Bone morphogenetic proteins. Growth factors (Chur, Switzerland) 22, 233-241.

Clarke, L. L., Grubb, B. R., Gabriel, S. E., Smithies, O., Koller, B. H., and Boucher, R. C. (1992). Defective epithelial chloride transport in a gene-targeted mouse model of cystic fibrosis. Science (New York, N.Y. 257, 1125-1128.

Coraux, C., Nawrocki-Raby, B., Hinnrasky, J., Kileztky, C., Gaillard, D., Dani, C., and Puchelle, E. (2005). Embryonic stem cells generate airway epithelial tissue. American journal of respiratory cell and molecular biology 32, 87-92.

Domyan, E. T., Ferretti, E., Throckmorton, K., Mishina, Y., Nicolis, S. K., and Sun, X. Signaling through BMP receptors promotes respiratory identity in the foregut via repression of Sox2. Development (Cambridge, England) 138, 971-981.

Evans, M. J., Van Winkle, L. S., Fanucchi, M. V., and Plopper, C. G. (2001). Cellular and molecular characteristics of basal cells in airway epithelium. Experimental lung research 27, 401-415.

Gontan, C., de Munck, A., Vermeij, M., Grosveld, F., Tibboel, D., and Rottier, R. (2008). Sox2 is important for two crucial processes in lung development: branching morphogenesis and epithelial cell differentiation. Developmental biology 317, 296-309.

Goss, A. M., Tian, Y., Tsukiyama, T., Cohen, E. D., Zhou, D., Lu, M. M., Yamaguchi, T. P., and Morrisey, E. E. (2009). Wnt2/2b and beta-catenin signaling are necessary and sufficient to specify lung progenitors in the foregut. Developmental cell 17, 290-298.

Green, M. D., Chen, A., Nostro, M. C., d'Souza, S. L., Schaniel, C., Lemischka, I. R., Gouon-Evans, V., Keller, G., and Snoeck, H. W. Generation of anterior foregut endoderm from human embryonic and induced pluripotent stem cells. Nature biotechnology 29, 267-272.

Guilbault, C., Saeed, Z., Downey, G. P., and Radzioch, D. (2007). Cystic fibrosis mouse models. American journal of respiratory cell and molecular biology 36, 1-7.

Kozawa, O., Hatakeyama, D., and Uematsu, T. (2002). Divergent regulation by p44/p42 MAP kinase and p38 MAP kinase of bone morphogenetic protein-4-stimulated osteocalcin synthesis in osteoblasts. Journal of cellular biochemistry 84, 583-589.

Lazzaro, D., Price, M., de Felice, M., and Di Lauro, R. (1991). The transcription factor TTF-1 is expressed at the onset of thyroid and lung morphogenesis and in restricted regions of the foetal brain. Development (Cambridge, England) 113, 1093-1104.

Lebeche, D., Malpel, S., and Cardoso, W. V. (1999). Fibroblast growth factor interactions in the developing lung. Mechanisms of development 86, 125-136.

Malpel, S., Mendelsohn, C., and Cardoso, W. V. (2000). Regulation of retinoic acid signaling during lung morphogenesis. Development (Cambridge, England) 127, 3057-3067.

Minoo, P., Su, G., Drum, H., Bringas, P., and Kimura, S. (1999). Defects in tracheoesophageal and lung morphogenesis in Nkx2.1(-/-) mouse embryos. Developmental biology 209, 60-71.

Miyazono, K., Kamiya, Y., and Morikawa, M. Bone morphogenetic protein receptors and signal transduction. Journal of biochemistry 147, 35-51.

Morrisey, E. E., and Hogan, B. L. Preparing for the first breath: genetic and cellular mechanisms in lung development. Developmental cell 18, 8-23.

Okubo, T., and Hogan, B. L. (2004). Hyperactive Wnt signaling changes the developmental potential of embryonic lung endoderm. Journal of biology 3, 11.

Perl, A. K., Kist, R., Shan, Z., Scherer, G., and Whitsett, J. A. (2005). Normal lung development and function after Sox9 inactivation in the respiratory epithelium. Genesis 41, 23-32.

Powell, P. P., Wang, C. C., Horinouchi, H., Shepherd, K., Jacobson, M., Lipson, M., and Jones, R. (1998). Differential expression of fibroblast growth factor receptors 1 to 4 and ligand genes in late fetal and early postnatal rat lung. American journal of respiratory cell and molecular biology 19, 563-572.

Que, J., Choi, M., Ziel, J. W., Klingensmith, J., and Hogan, B. L. (2006). Morphogenesis of the trachea and esophagus: current players and new roles for noggin and Bmps. Differentiation; research in biological diversity 74, 422-437.

Que, J., Luo, X., Schwartz, R. J., and Hogan, B. L. (2009). Multiple roles for Sox2 in the developing and adult mouse trachea. Development (Cambridge, England) 136, 1899-1907.

Rawlins, E. L., Clark, C. P., Xue, Y., and Hogan, B. L. (2009). The Id2+ distal tip lung epithelium contains individual multipotent embryonic progenitor cells. Development (Cambridge, England) 136, 3741-3745.

Rock, J. R., Onaitis, M. W., Rawlins, E. L., Lu, Y., Clark, C. P., Xue, Y., Randell, S. H., and Hogan, B. L. (2009). Basal cells as stem cells of the mouse trachea and human airway epithelium. Proceedings of the National Academy of Sciences of the United States of America 106, 12771-12775.

Rock, J. R., Randell, S. H., and Hogan, B. L. Airway basal stem cells: a perspective on their roles in epithelial homeostasis and remodeling. Disease models & mechanisms 3, 545-556.

Roszell, B., Mondrinos, M. J., Seaton, A., Simons, D. M., Koutzaki, S. H., Fong, G. H., Lelkes, P. I., and Finck, C. M. (2009). Efficient derivation of alveolar type II cells from embryonic stem cells for in vivo application. Tissue Eng Part A 15, 3351-3365.

Sakiyama, J., Yamagishi, A., and Kuroiwa, A. (2003). Tbx4-Fgf10 system controls lung bud formation during chicken embryonic development. Development (Cambridge, England) 130, 1225-1234.

Samadikuchaksaraei, A., Cohen, S., Isaac, K., Rippon, H. J., Polak, J. M., Bielby, R. C., and Bishop, A. E. (2006). Derivation of distal airway epithelium from human embryonic stem cells. Tissue engineering 12, 867-875.

Serls, A. E., Doherty, S., Parvatiyar, P., Wells, J. M., and Deutsch, G. H. (2005). Different thresholds of fibroblast growth factors pattern the ventral foregut into liver and lung. Development (Cambridge, England) 132, 35-47.

Sherwood, R., Maehr, R., Mazzoni, E. O, and Melton, D. A. (2011). Wnt Signaling Specifies and Patterns Intestinal Endoderm. Mechanisms of development In press.

Shu, W., Guttentag, S., Wang, Z., Andl, T., Ballard, P., Lu, M. M., Piccolo, S., Birchmeier, W., Whitsett, J. A., Millar, S. E., et al. (2005). Wnt/beta-catenin signaling acts upstream of N-myc, BMP4, and FGF signaling to regulate proximal-distal patterning in the lung. Developmental biology 283, 226-239.

Spence, J. R., Mayhew, C. N., Rankin, S. A., Kuhar, M. F., Vallance, J. E., Tolle, K., Hoskins, E. E., Kalinichenko, V. V., Wells, S. I., Zorn, A. M., et al. Directed differentiation of human pluripotent stem cells into intestinal tissue in vitro. Nature 470, 105-109.

Van Haute, L., De Block, G., Liebaers, I., Sermon, K., and De Rycke, M. (2009). Generation of lung epithelial-like tissue from human embryonic stem cells. Respiratory research 10, 105.

Van Vranken, B. E., Romanska, H. M., Polak, J. M., Rippon, H. J., Shannon, J. M., and Bishop, A. E. (2005). Coculture of embryonic stem cells with pulmonary mesenchyme: a microenvironment that promotes differentiation of pulmonary epithelium. Tissue engineering 11, 1177-1187.

von Bubnoff, A., and Cho, K. W. (2001). Intracellular BMP signaling regulation in vertebrates: pathway or network? Developmental biology 239, 1-14.

Wang, D., Haviland, D. L., Burns, A. R., Zsigmond, E., and Wetsel, R. A. (2007). A pure population of lung alveolar epithelial type II cells derived from human embryonic stem cells. Proceedings of the National Academy of Sciences of the United States of America 104, 4449-4454.

Warren, L., Manos, P. D., Ahfeldt, T., Loh, Y. H., Li, H., Lau, F., Ebina, W., Mandal, P. K., Smith, Z. D., Meissner, A., et al. Highly efficient reprogramming to pluripotency and directed differentiation of human cells with synthetic modified mRNA. Cell stem cell 7, 618-630.

Watanabe, K., Kamiya, D., Nishiyama, A., Katayama, T., Nozaki, S., Kawasaki, H., Watanabe, Y., Mizuseki, K., and Sasai, Y. (2005). Directed differentiation of telencephalic precursors from embryonic stem cells. Nature neuroscience 8, 288-296.

Weaver, M., Yingling, J. M., Dunn, N. R., Bellusci, S., and Hogan, B. L. (1999). Bmp signaling regulates proximal-distal differentiation of endoderm in mouse lung development. Development (Cambridge, England) 126, 4005-4015.

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Asp Gly Cys Glu Leu
1               5
```

Shu, W., Lu, M. M., Zhang, Y., Tucker, P. W., Zhou, D., and Morrisey, E. E. (2007). Foxp2 and Foxp1 cooperatively regulate lung and esophagus development. Development (Cambridge, England) 134, 1991-2000.

Sieber, C., Kopf, J., Hiepen, C., and Knaus, P. (2009). Recent advances in BMP receptor signaling. Cytokine & growth factor reviews 20, 343-355.

Snouwaert, J. N., Brigman, K. K., Latour, A. M., Malouf, N. N., Boucher, R. C., Smithies, O., and Koller, B. H. (1992). An animal model for cystic fibrosis made by gene targeting. Science (New York, N.Y. 257, 1083-1088.

The invention claimed is:

1. A method of generating a human lung progenitor cell or population of human lung progenitor cells that is Nkx2.1 positive, Tuj1 negative and Pax8 negative, the method comprising contacting a human foregut endoderm cell with FGF2, WNT and BMP4, each for a time sufficient and at a concentration sufficient to permit differentiation of said human foregut endoderm cell to an Nkx2.1 positive, Tuj1 negative, Pax8 negative lung progenitor cell.

2. The method of claim 1, wherein the contacting is performed for at least 2 days.

3. The method of claim 1, further comprising contacting the Nkx2.1 positive, Tuj1 negative, Pax8 negative lung progenitor cell with BMP7, FGF7, a WNT antagonist, and a MAPKK/ERK antagonist, each for a time sufficient and at a concentration sufficient to permit differentiation of the Nkx2.1 positive, Tuj1 negative, Pax8 negative lung progenitor cell to a Nkx2.1 positive, Sox2 positive proximal airway multipotent progenitor cell.

* * * * *